(12) United States Patent
Kirk et al.

(10) Patent No.: US 7,705,331 B1
(45) Date of Patent: Apr. 27, 2010

(54) METHODS AND SYSTEMS FOR PROVIDING ILLUMINATION OF A SPECIMEN FOR A PROCESS PERFORMED ON THE SPECIMEN

(75) Inventors: Greg Kirk, Pleasanton, CA (US); Rich Solarz, Danville, CA (US); Chris Kirk, Beaconsfield (GB); Gil Delgado, Livermore, CA (US); Anatoly Schemelinin, Pleasanton, CA (US); Jim Li, San Jose, CA (US); Qibiao Chen, Fremont, CA (US); Charles Nenghe Wang, Santa Clara, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 473 days.

(21) Appl. No.: 11/771,430

(22) Filed: Jun. 29, 2007

Related U.S. Application Data

(60) Provisional application No. 60/806,204, filed on Jun. 29, 2006.

(51) Int. Cl.
  *G21G 4/00* (2006.01)
(52) U.S. Cl. .................. 250/493.1; 250/306; 250/307
(58) Field of Classification Search .............. 250/493.1, 250/306, 307
  See application file for complete search history.

(56) References Cited

U.S. PATENT DOCUMENTS

| | | | |
|---|---|---|---|
| 5,301,203 A * | 4/1994 | Schlie et al. ................ 372/55 |
| 5,686,793 A | 11/1997 | Turner et al. | |
| 5,798,618 A | 8/1998 | van Os et al. | |
| 5,864,394 A | 1/1999 | Jordan, III et al. | |
| 6,157,141 A | 12/2000 | Lapatovich et al. | |
| 6,313,467 B1 | 11/2001 | Shafer et al. | |
| 6,507,031 B1 | 1/2003 | Jinbo et al. | |
| 6,563,577 B2 | 5/2003 | Oomori et al. | |
| 6,633,831 B2 | 10/2003 | Nikoonahad et al. | |
| 6,862,096 B2 | 3/2005 | Vaez-Iravani et al. | |
| 6,879,391 B1 | 4/2005 | Danko | |
| 2003/0228050 A1 | 12/2003 | Geshel et al. | |
| 2004/0036393 A1 | 2/2004 | Eastlund et al. | |
| 2004/0095575 A1 | 5/2004 | Woo et al. | |
| 2004/0201837 A1 | 10/2004 | Lange et al. | |
| 2004/0252879 A1 | 12/2004 | Tiemeyer et al. | |
| 2005/0052643 A1 | 3/2005 | Lange et al. | |
| 2005/0252752 A1 | 11/2005 | Fielden et al. | |
| 2005/0254050 A1 | 11/2005 | Fielden et al. | |
| 2008/0258085 A1 | 10/2008 | Bauer | |

OTHER PUBLICATIONS

U.S. Appl. No. 11/623,981, filed Jan. 17, 2007, Kirk et al.

Babucke et al., "On the energy balance in the core of electrode-stabilized high-pressure mercury discharges," J. Phys. D: Appl. Phys. 24. (1991) pp. 1316-1321.

(Continued)

*Primary Examiner*—Kiet T Nguyen
(74) *Attorney, Agent, or Firm*—Ann Marie Mewherter

(57) ABSTRACT

Methods and systems for providing illumination of a specimen for a process performed on the specimen are provided. One system configured to provide illumination of a specimen for a process performed on the specimen includes a laser configured to generate excitation light. The system also includes focusing optics configured to focus the excitation light to a plasma in an electrodeless lamp such that the plasma generates light. The system is also configured such that the light illuminates the specimen during the process.

116 Claims, 13 Drawing Sheets

OTHER PUBLICATIONS

Derra et al., "UHP lamp systems for projectino applications," J. Phys. D: Appl. Phys. 38 (2005) pp. 2995-3010.

Wilbers et al., "The VUV Emissivity of a high-pressure cascade argon arc from 125 to 200 nm," J. Quant. Spectrosc. Radiat. Transfer, vol. 46, No. 4, 1991, pp. 299-308.

Erskine et al., "Measuring Opacity of Shock Generated Argon Plasmas," J. Quant. Spectrosc. Radiat. Transfer, vol. 51, No. 1/2, 1994, pp. 97-100.

Smith, David, "Gas-Breakdown Dependence on Beam Size and Pulse Duration with 10.6-u Wavelength Radiation," Journal of Applied Physics, vol, 19, No. 10, Nov. 15, 1971, pp. 405-408.

Jeng et al., "Theoretical investigation of laser-sustained argon plasmas," J. Appl. Phys. vol. 60, No. 7, Oct. 1, 1986, pp. 2272-2279.

Kozlov et al., "Radiative losses by argon plasma and the emissive model of a continuous optical discharge," Sov. Phys-JETP, vol. 39, No. 3, Sep. 1974, pp. 463-468.

Cohn et al., "Magetic-Field-Dependent Breakdown of $CO_2$-Laser-Produced Plasma," Appl. Phys. Lett., vol. 20, No. 6, Mar. 15, 1972, pp. 225-227.

Franzen, "cw gas breakdown in argon using 10.6-um laser radiation," Appl. Phys. Lett., vol. 21, No. 2, Jul. 15, 1972, pp. 62-64.

Harilal et al., "Influence of ambient gas on the temperature and density of laser produced carbon plasma," Appl. Phys. Lett. 72 (2) Jan. 1, 1998, pp. 167-169.

D. L. Franzen, "Continuous laser-sustained plasmas," J. Appl. Phys. 44(4), pp. 1727-1732 (1972).

R. Wiehle et al. "Dynamics of strong-field above-threshold ionization of argon: Comparison between experiment and theory," The American Physical Society, 2003, pp. 063405-1-063405-7.

V. V. Kostin et al., "Emission from a Plasma Heated by Short Laser Pulses," Plasma Physics Reports, vol. 23, No. 2, 1997, pp. 102-109.

A. Takahashi et al., "$Ar_2$ excimer emission from a laser-heated plasma in a high-pressure argon gas," App. Phys. Lett., vol. 77, No. 25, Dec. 2000, pp. 4115-4117.

H. Tanaka et al., "Production of laser-heated plasma in high-pressure Ar gas and emission characteristics of vacuum ultraviolet radiation from $Ar_2$ excimers," ppl. Phys. B, 74, 2002, pp. 323-326.

A. Takahashi et al., Numerical Analysis of $Ar_2$ Excimer Production in Laser-Produced Plasmas, Jap. Journ. Appl. Phys., vol. 37, 1998, pp. L390-L393.

S. Schohl et al., "Absolute detection of metastable rare gas atoms by a cw laser photoionization method," Z. Phys. D—Atoms, Molecules and Clusters, 21(1), 1991, pp. 25-39.

Z. Szymanski et al., "Nonstationary laser-sustained plasma," J. Appl. Phys., 69(6), Mar. 1991, pp. 3480-3484.

Z. Szymanski et al., "Spectroscopic study of a supersonic jet of laser-heated argon plasma," J. Phys. D: App. Phys. 30, 1997, pp. 998-1006.

J. M. Girard et al. "Generating conditions of a laser-sustained argon plasma jet," J. Phys. D: App. Phys. 26, 1993, pp. 1382-1393.

A. B. Lewis et al., "Measurements of CW Photoionization for the use in stable high pressure tea laser discharge," 2nd Inter. Conf. on Plasma Science IEEE, May 1975, p. 45.

J. E. Daily et al., "Two-photonionization of the Ca 4s3d D2 level in an optical dipole trap," Phys. Rev. A, 71, 2005, pp. 043406-1-043406-5.

J. L. Emmett et al., "Direct Measurement of Xenon Flashtube Opacity," J. Appl. Phys., vol. 35, No. 9, Sep. 1964, pp. 2601-2604.

V. Malka et al., "Channel Formation in Long Laser Pulse Interaction with a Helium Gas Jet" Phys. Rev. Lett., vol. 79, No. 16, Oct. 1997, pp. 2979-2982.

K. Krushelnick et al. "Plasma Channel Formation and Guiding during High Intensity Short Pulse Laser Plasma Experiments," Phys. Rev. Lett., vol. 78, No. 21, May 1997, pp. 4047-4050.

S. P. Nikitin et al. "Guiding of intense femtosecond pulses in preformed plasma channels," Optics Letters, vol. 22, No. 23, Dec. 1997, pp. 1787-1789.

U.S. Appl. No. 60/974,030 (Bhaskar et al.) entitled Systems and Methods for Creating Persistent Data for a Wafer and for Using Persistent Data for Inspection-Related Functions filed Sep. 20, 2007.

U.S. Appl. No. 61/074,065 (Chen et al.) entitled Computer-Implemented Methods, Computer-Readable Media, and Systems for Determining One of More Characteristics of a Wafer filed Jun. 19, 2008.

U.S. Appl. No. 12/128,426 (Biellak et al.) entitled Systems and Methods for Determining Two or More Characteristics of a Wafer filed Jul. 24, 2008.

U.S. Appl. No. 12/179,260 (Reich et al.) entitled Computer-Implemented Methods for Inspecting and/or Classifying a Wafer filed Jul. 24, 2008.

International Search Report and Written Opinion for PCT/US08/075867 mailed Feb. 17, 2009.

\* cited by examiner

METHODS AND SYSTEMS FOR PROVIDING ILLUMINATION OF A SPECIMEN FOR A PROCESS PERFORMED ON THE SPECIMEN

PRIORITY CLAIM

This application claims priority to U.S. Provisional Application Ser. No. 60/806,204 entitled "Methods and Systems for Providing Illumination of a Specimen for Inspection," filed Jun. 29, 2006, which is incorporated by reference as if fully set forth herein.

BACKGROUND OF THE INVENTION

1. Field of the Invention

The present invention generally relates to methods and systems for providing illumination of a specimen for a process performed on the specimen. Certain embodiments relate to methods and systems for providing illumination of a specimen using an electrodeless lamp.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. When inspecting specular or quasi-specular surfaces such as semiconductor wafers, bright field (BF) and dark field (DF) modalities are used. In BF inspection systems, collection optics are positioned such that the collection optics capture a substantial portion of the light specularly reflected by the surface under inspection. In contrast, in DF inspection systems, the collection optics are positioned out of the path of the specularly reflected light such that the collection optics capture light scattered by objects on the surface being inspected such as microcircuit patterns or contaminants on the surfaces of wafers.

Many different light sources have been used in inspection systems. For example, electrode based, relatively high intensity discharge arc lamps are used in inspection systems. However, these light sources have a number of disadvantages, For instance, electrode based, relatively high intensity discharge arc lamps have brightness limits and power limits due to electrostatic constraints on current density from the electrodes, the limited emissivity of gases as black body emitters, the relatively rapid erosion of electrodes made from refractory materials due to the presence of relatively large current densities at the cathodes, and the inability to control dopants (which can lower the operating temperature of the refractory cathodes) for relatively long periods of time at the required emission current.

Many different light sources have also been developed for various other applications. For instance, some carbon dioxide laser produced plasma lamps have been developed though not disclosed for use in wafer or reticle inspection applications. Examples of such plasma lamps are described in Smith, Appl. Phys. Lett., 19(10), 405-408 (1971), Cohn et al., Appl. Phys. Lett., 20(6), 225-227 (1972), Franzen, Appl. Phys. Lett., 21(2), 62-64 (1972), and Harilal et al., Appl. Phys. Lett., 72(2), 167-169 (1998), which are incorporated by reference as if fully set forth herein.

Accordingly, it may be advantageous to develop electrodeless lamps for inspection applications, for example, by optimizing the operation of deep ultraviolet (DUV) electrodeless lamps for use in inspection applications such as semiconductor wafer inspection by optimizing the pressure, gas type, energy deposition, energy deposition profile, or some combination thereof of the lamp while at the same time eliminating the need for electrodes.

SUMMARY OF THE INVENTION

The following description of various embodiments of methods and systems is not to be construed in any way as limiting the subject matter of the appended claims.

One embodiment relates to a system configured to provide illumination of a specimen for a process performed on the specimen. The system includes a laser configured to generate excitation light. The system also includes focusing optics configured to focus the excitation light to a plasma in an electrodeless lamp such that the plasma generates light. The system is also configured such that the light illuminates the specimen during the process.

In one embodiment, the laser includes a continuous-wave (cw) laser. In another embodiment, the laser includes a diode laser, a diode laser stack, a fiber laser, a fiber coupled diode laser, a carbon dioxide laser, an acoustically modulated diode, or a diode pumped fiber laser. In one embodiment, a power of the laser is greater than about 100 W. In an additional embodiment, an optical average cw power of the excitation light is about 100 W to about 1000 W. In a further embodiment, the system includes an additional laser configured to generate additional excitation light. In one such embodiment, the focusing optics are configured to focus the additional excitation light to the plasma, and a sum of the power of the laser and the additional laser is in a range of about 100 W cw to about 1000 W cw.

In one embodiment, a wavelength of the excitation light is about 0.7 µm to about 1.5 µm. In another embodiment, a wavelength of the excitation light is less than about 10 µm.

In one embodiment, the focusing optics are configured to focus the excitation light to the lamp to initiate the plasma. In another embodiment, the system includes a pulsed light source, a radio frequency coil, a voltage source external to the lamp, or some combination thereof configured to initiate the plasma.

In one embodiment, the plasma has a geometry shaped to substantially match collection optics of a detection subsystem of a system configured to inspect the specimen. In another embodiment, an excitation volume of the electrodeless lamp is substantially matched to a field of view of collection optics of a detection subsystem of a system configured to inspect the specimen. In an additional embodiment, the plasma has a cylindrical shape substantially matched to image onto the specimen in the system.

In one embodiment, the focusing optics are configured to focus the excitation light to a cylindrical-shaped region within the electrodeless lamp. In one such embodiment, the cylindrical-shaped region has a diameter of about 0.5 mm to about 1 mm and a thickness of about 100 µm to about 200 µm. In another embodiment, the system includes at least one additional laser configured to generate additional excitation light. In one such embodiment, the focusing optics are configured to direct the excitation light and the additional excitation light to the plasma simultaneously such that the excitation light and the additional excitation light overlap within a cylindrical-shaped region within the electrodeless lamp, and the cylindrical-shaped region has a diameter of about 0.5 mm to about 1 mm and a thickness of about 100 µm to about 200 µm.

In one embodiment, the laser includes a frequency doubled laser, and a wavelength of the excitation light is about 0.4 µm to about 0.7 µm.

In one embodiment, the light generated by the plasma includes deep ultraviolet (DUV) light. In another embodiment, the light generated by the plasma includes broadband light. In a further embodiment, the light generated by the plasma has a single line spectra.

In one embodiment, the light generated by the plasma includes light in a spectral region from about 180 nm to about 450 nm. In another embodiment, the light generated by the plasma includes light in a spectral region from about 200 nm to about 450 nm. In an additional embodiment, the plasma is generated using a rare earth gas and a mercury gas, and the light generated by the plasma includes light in a spectral region from about 230 nm to about 480 nm. In one embodiment, the light generated by the plasma includes excimer radiation, and the electrodeless lamp includes about 1 atm or more of background rare gas and about 1 atm or less of a halide containing gas.

In one embodiment, the plasma has a diameter of about 0.5 mm to about 1 mm. In another embodiment, the light generated by the plasma has a diameter of about 100 µm to about 2 mm.

In one embodiment, the electrodeless lamp is at a pressure of above about 1 atm at a working temperature of the electrodeless lamp, and the light generated by the plasma includes light in a spectral region from about 200 nm to about 400 nm. In some embodiments, the light generated by the plasma has a brightness of about 10 W/mm$^2$-sr to about 50 W/mm$^2$-sr in a spectral region from about 200 nm to about 400 nm. In another embodiment, the light generated by the plasma has a brightness of about 2 W/mm$^2$-sr to about 50 W/mm$^2$-sr in an integral region of the electromagnetic spectrum from about 200 nm to about 400 nm. In a further embodiment, the light generated by the plasma has an average power of at least about 3 W within any band in a spectral region from about 200 nm to about 450 nm.

In one embodiment, a temperature of the plasma is about 10,000 K to about 30,000 K. In another embodiment, a temperature of the plasma is held substantially constant by the excitation light.

In some embodiments, the electrodeless lamp includes a fill gas, and the fill gas includes argon, krypton, xenon, fluorine, chlorine, chlorine dimers, fluorine dimers, a homogenous diatomic gas, nitrogen trifluoride, sulfur hexafluoride, nitric oxide, mercury, a halide containing gas, mercury halides, diatomic halides, halides, a rare gas, rare earths, transition metals, lanthanide metals, or some combination thereof.

In one embodiment, the electrodeless lamp includes a fill gas at a gas pressure such that an opacity of the plasma does not prohibit a majority of the light generated by the plasma from exiting the lamp. In another embodiment, the plasma does not produce an average plasma opacity over a plasma axis length of greater than about 1 e-folding from one end of the electrodeless lamp to another end of the electrodeless lamp. In an additional embodiment, the electrodeless lamp includes a fill gas, and an opacity of the fill gas at a working temperature and pressure of the electrodeless lamp is less than or equal to about 10% reabsorption of light emitted from a center of the lamp within a spectral region from about 200 nm to about 450 nm.

In one embodiment, a fill pressure of gases in the electrodeless lamp is about 4 atm or higher. In another embodiment, a fill pressure of the electrodeless lamp is about 5 atm to about 20 atm at room temperature. In a further embodiment, a gas pressure within the electrodeless lamp is about 1 atm to about 50 atm.

In one embodiment, the plasma includes one or more species that fluoresce in a region between about 180 nm and about 350 nm to a ground electronic state. In one such embodiment, the one or more species include mercury that emits resonance lines at 2537 Å, neutral barium that emits resonance lines at 2409 Å, neutral cobalt that emits resonance lines at 2402 Å, neutral magnesium that emits resonance lines at 2025 Å, neutral nickel that emits resonance lines at 2026 Å, neutral scandium that emits resonance lines at 2000 Å, neutral nickel terminating on a 879 cm$^{-1}$ electronic metastable state, or some combination thereof. In another such embodiment, atoms or molecules that form the one or more species are present in the electrodeless lamp prior to generation of the plasma in a quantity or quantities that limit the vapor pressure of the atoms or molecules in the electrodeless lamp such that substantially all of the atoms or molecules are vaporized before the lamp reaches operating temperature. In a further such embodiment, the one or more species include atoms formed by decomposition of feed molecules in the electrodeless lamp.

In some embodiments, the plasma includes one or more species that fluoresce in a region between about 180 nm and about 350 nm to electronic metastable states within about 0.5 eV of a ground electronic state. In some such embodiments, the one or more species include mercury that emits resonance lines at 2537 Å, neutral barium that emits resonance lines at 2409 Å, neutral cobalt that emits resonance lines at 2402 Å, neutral magnesium that emits resonance lines at 2025 Å, neutral nickel that emits resonance lines at 2026 Å, neutral scandium that emits resonance lines at 2000 Å, neutral nickel terminating on a 879 cm$^{-1}$ electronic metastable state, or some combination thereof. In another such embodiment, atoms or molecules that form the one or more species are present in the electrodeless lamp prior to generation of the plasma in a quantity or quantities that limit the vapor pressure of the atoms or molecules in the electrodeless lamp such that substantially all of the atoms or molecules are vaporized before the lamp reaches operating temperature. In a further such embodiment, the one or more species include atoms formed by decomposition of feed molecules in the electrodeless lamp.

In one embodiment, the electrodeless lamp includes one or more operating gases that have atomic transitions from electronically excited states to a ground electronic state of one or more corresponding neutral atoms or a state within about 1 eV to about 2 eV of the ground electronic state. In another embodiment, the electrodeless lamp includes feed molecules of which about 1% or greater are dissociated at an operating temperature proximate a center of the plasma. In one such embodiment, the feed molecules include iodine, chlorine, bromine, sulfur, nitrogen, oxygen, a diatomic gas, one or more homonuclear diatomic feed materials capable of recombining to form only their corresponding molecular species, one or more rare gases, or some combination thereof. In an additional embodiment, the electrodeless lamp includes feed molecules of which about 1% or greater are dissociated at an operating temperature of about 600 K to about 25,000 K.

In one embodiment, the electrodeless lamp includes diatomic hydrogen. In one such embodiment, the light generated by the plasma has a wavelength of about 121 nm. In another such embodiment, the light generated by the plasma has a wavelength of about 121 nm, about 937 nm, about 949 nm, about 972 nm, about 1025 nm, or some combination thereof.

In one embodiment, the electrodeless lamp includes a background rare gas and a gas containing a halide. In one such embodiment, a pressure of the background rare gas is at least about 1 atm, and a pressure of the gas containing the halide is less than or equal to about 1 atm.

In one embodiment, the electrodeless lamp includes one of an internal lens and a curved reflector. In another embodiment, the focusing optics include a lens configured to focus the excitation light to a spot size and radiance sufficient to sustain the plasma. In one such embodiment, the lens has a numerical aperture (NA) of at least about 0.3. In an additional embodiment, the focusing optics include a lens configured to focus the excitation light to the plasma such that the plasma has a predetermined shape. In one such embodiment, the lens has an NA of at least about 0.3.

In one embodiment, the system includes at least one heat source located proximate to the electrodeless lamp and configured to maintain atoms in the plasma in a vapor phase.

In one embodiment, the system includes an illumination subsystem configured to illuminate the specimen during the process with the light generated by the plasma. In one such embodiment, the illumination subsystem includes a condenser lens configured to collect the light generated by the plasma. In another such embodiment, the illumination subsystem includes an elliptical reflector configured to collect the light generated by the plasma, and the plasma is located at one focal point of the elliptical reflector.

In one embodiment, the specimen includes a wafer. In another embodiment, the specimen includes a patterned wafer. In an additional embodiment, the specimen includes a reticle.

In one embodiment, an NA of the focusing optics is selected such that a size of the plasma is reduced along a direction to which the excitation light is focused to the plasma by the focusing optics. In one embodiment, the laser includes a distributed light source. In an additional embodiment, the focusing optics include at least one optical element configured to focus the excitation light to the plasma and configured to collect the light generated by the plasma.

In one embodiment, the focusing optics are configured to focus the excitation light to the plasma in two substantially opposite directions simultaneously. In another embodiment, the focusing optics include at least one reflective optical element and at least one refractive optical element, and the at least one reflective optical element and the at least one refractive optical element are configured to focus the excitation light to the plasma simultaneously. In an additional embodiment, the focusing optics are configured to focus the excitation light to the plasma in two substantially perpendicular directions.

In one embodiment, the focusing optics are configured to focus the excitation light to the plasma at different directions simultaneously to substantially the same focal spot. In another embodiment, the focusing optics are configured to focus the excitation light to the plasma at different directions simultaneously to offset focal spots. In a further embodiment, the focusing optics are configured to collect the excitation light that is not absorbed by the plasma and to focus the collected excitation light to the plasma.

In one embodiment, the system includes a gas flow subsystem configured to direct a gas to the plasma such that the gas directed to the plasma affects a shape of the plasma. In another embodiment, the system includes a gas flow subsystem configured to direct a gas to the plasma such that the gas directed to the plasma increases isolation of the plasma. In an additional embodiment, the system includes a gas flow subsystem configured to direct a gas to the plasma at a direction substantially opposite to a direction at which the focusing optics focus the excitation light to the plasma. In a further embodiment, the system includes a gas flow subsystem configured to direct a gas to the plasma at a direction substantially perpendicular to a direction at which the focusing optics focus the excitation light to the plasma. In some embodiments, the system includes a gas flow subsystem configured to direct a gas to the plasma such that the gas increases propagation of the generated light through the plasma.

In one embodiment, the system includes a gas flow subsystem configured to direct a gas to the plasma through an aperture in an optical element of the focusing optics. In another embodiment, the system includes a gas flow subsystem configured to direct a gas to the plasma through a sonic or supersonic nozzle to reduce a volume of the plasma and to reduce absorption of the generated light by the gas.

In some embodiments, the system includes a gas flow subsystem configured to direct a gas to the plasma. In one such embodiment, the gas flow subsystem includes a cylindrical-shaped nozzle. In another such embodiment, the gas directed to the plasma increases uniformity of a density profile of the plasma. In an additional such embodiment, the gas directed to the plasma creates an interaction media having a density suitable for interactions between the excitation light and the plasma. In a further such embodiment, a pressure of the gas directed to the plasma is selected based on one or more predetermined characteristics of the plasma. In yet another such embodiment, the gas flow subsystem includes a nozzle through which the gas is directed to the plasma, and a diameter of the nozzle is selected based on one or more predetermined characteristics of the plasma.

In some embodiments, the system includes a gas flow subsystem configured to direct a gas jet to the plasma. In one such embodiment, the focusing optics are configured to direct the excitation light to one or more edges of the gas jet thereby affecting a shape of the gas jet.

In one embodiment, the system is configured to apply an external magnetic field to the plasma to alter one or more characteristics of the plasma. In another embodiment, the system includes a gas flow subsystem configured to direct one or more feed materials to the plasma after generation of the plasma. In an additional embodiment, the system includes a cleaning subsystem configured to remove photocontamination from one or more optical elements of the focusing optics, one or more optical elements of the system, or some combination thereof. In some embodiments, the plasma is generated from one or more feed materials that include a liquid.

In one embodiment, the system includes an illumination subsystem configured to illuminate the specimen during the process with the light generated by the plasma, and the illumination subsystem includes a reflective optical element configured to collect the light generated by the plasma and to direct the collected light to one or more refractive optical elements of the illumination subsystem. In another embodiment, the focusing optics include a reflective optical element configured to focus the excitation light to the plasma, and the excitation light includes an expanded laser beam.

In an additional embodiment, the focusing optics are configured to focus the excitation light to the plasma at different directions simultaneously. In a further embodiment, the system includes an illumination subsystem configured to illuminate the specimen during the process with the light generated by the plasma, and the illumination subsystem includes one or more refractive optical elements configured to focus the excitation light to the plasma. In some embodiments, the focusing optics include at least one optical element configured to focus the excitation light to the plasma and configured to collect the light generated by the plasma, and the at least one optical element includes a reflective optical element.

In one embodiment, the system includes an illumination subsystem configured to illuminate the specimen during the process with the light generated by the plasma. In one such embodiment, the illumination subsystem is configured to collect the light generated by the plasma across a solid angle of about 4π. In another such embodiment, the illumination subsystem is configured to direct the light to a pupil plane of the system such that the light has a substantially uniform intensity across the pupil plane.

In an additional such embodiment, the illumination subsystem includes a partial elliptical reflector and a half spherical reflector. In one such embodiment, the plasma is positioned at one focal point of the partial elliptical reflector, and the half spherical reflector is substantially centered to the plasma. In another such embodiment, the partial elliptical reflector and the half spherical reflector are configured to collect the light generated by the plasma, the half spherical reflector is configured to direct the light collected by the half spherical reflector to the partial elliptical reflector, and the partial elliptical reflector is configured to direct the light from the half spherical reflector and the light collected by the partial elliptical reflector to another optical element of the illumination subsystem.

Each of the embodiments of the system described above may be further configured as described herein. In addition, each of the embodiments of the system described above may be included in any of the other systems described herein and may be used in any of the methods described herein.

Another embodiment relates to a method for providing illumination of a specimen for a process performed on the specimen. The method includes focusing excitation light from a laser to an electrodeless lamp to generate a plasma in the electrodeless lamp such that the plasma generates light. The method also includes illuminating the specimen with the generated light during the process.

The embodiment of the method described above may include any other step(s) of any other method(s) described herein. In addition, the embodiment of the method described above may be performed by any of the systems described herein.

An additional embodiment relates to a method for determining one or more characteristics of a specimen. The method includes focusing excitation light from a laser to an electrodeless lamp to generate a plasma in the electrodeless lamp such that the plasma generates light. The method also includes illuminating the specimen with the generated light. In addition, the method includes generating output responsive to light from the specimen resulting from the illumination of the specimen. The method further includes determining the one or more characteristics of the specimen using the output.

The embodiment of the method described above may include any other step(s) of any other method(s) described herein. In addition, the embodiment of the method described above may be performed by any of the systems described herein.

A further embodiment relates to a system configured to determine one or more characteristics of a specimen. The system includes a laser configured to generate excitation light. The system also includes focusing optics configured to focus the excitation light to a plasma in an electrodeless lamp such that the plasma generates light. In addition, the system includes an illumination subsystem configured to illuminate the specimen with the light generated by the plasma. The system further includes a detection subsystem configured to generate output responsive to light from the specimen due to illumination of the specimen. The output can be used to determine the one or more characteristics of the specimen.

In one embodiment, the system is configured as a bright field inspection system. In another embodiment, the system is configured as a dark field inspection system. In an additional embodiment, the system is configured as a defect review system. In a further embodiment, the system is configured as a metrology system.

In one embodiment, the one or more characteristics include one or more dimensions of one or more patterned features formed on the specimen. In another embodiment, the one or more characteristics include a shape of one or more patterned features formed on the specimen.

In one embodiment, the specimen includes a wafer. In another embodiment, the specimen includes a patterned wafer. In an additional embodiment, the specimen includes a reticle.

Each of the embodiments of the system described above may be further configured as described herein. In addition, each of the embodiments of the system described above may be used in any of the methods described herein.

Yet another embodiment relates to a system configured to generate an image of a specimen. The system includes a laser configured to generate excitation light. The system also includes focusing optics configured to focus the excitation light to a plasma in an electrodeless lamp such that the plasma generates light. In addition, the system includes an illumination subsystem configured to illuminate the specimen with the light generated by the plasma. The system further includes a detection subsystem configured to generate output responsive to electrons emitted by the specimen due to illumination of the specimen with the light generated by the plasma. The output includes the image of the specimen.

In one embodiment, the light generated by the plasma includes DUV light. In another embodiment, the specimen includes a surface formed of a semiconductive material. In an additional embodiment, the light generated by the plasma includes broadband light such that the system can image a selectable set of work functions of the specimen.

Each of the embodiments of the system described above may be further configured as described herein. In addition, each of the embodiments of the system described above may be used in any of the methods described herein.

Still another embodiment relates to a system configured to perform a lithography process on a specimen. The system includes a laser configured to generate excitation light. The system also includes focusing optics configured to focus the excitation light to a plasma in an electrodeless lamp such that the plasma generates light. In addition, the system includes an illumination subsystem configured to image the light generated by the plasma onto the specimen in a predetermined pattern such that the predetermined pattern can be transferred to the specimen.

In one embodiment, the light generated by the plasma includes i-line light. Each of the embodiments of the system described above may be further configured as described herein. In addition, each of the embodiments of the system described above may be used in any of the methods described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
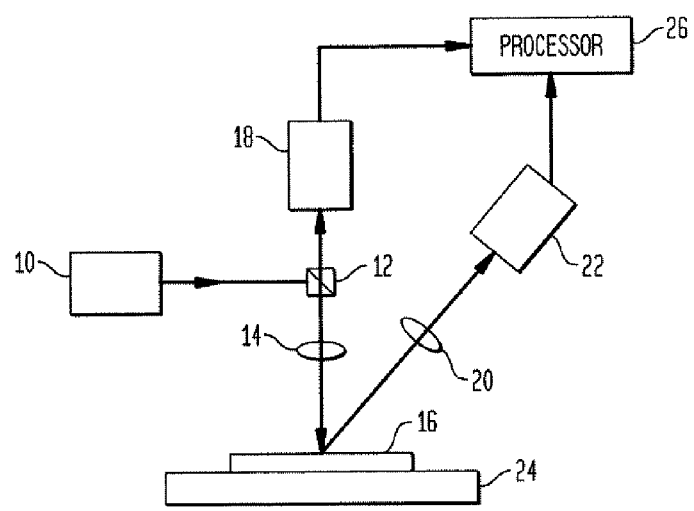
FIG. 1 is a schematic diagram illustrating a side view of one embodiment of a system configured to determine one or more characteristics of a specimen.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "specimen" generally refers to a wafer, a photomask, or a reticle. However, it is to be understood that the methods and systems described herein may be used for providing illumination of any other specimen known in the art and/or determining one or more characteristics (e.g., by inspection, defect review, metrology, imaging, etc.) of any other specimen known in the art.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, a semiconductive material, and a conductive material. Many different types of such layers are known in the art, and the term wafer as used herein is intended to encompass a wafer including all types of such layers.

One or more layers formed on a wafer may be patterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

The terms "reticle" and "photomask" are used interchangeably herein. A reticle generally includes a transparent substrate such as glass, borosilicate glass, and fused silica having opaque regions formed thereon. The opaque regions may be replaced by regions etched into the transparent substrate.

Many different types of reticles are known in the art, and the term reticle as used herein is intended to encompass all types of reticles.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

FIG. 1 illustrates one embodiment of a system configured to determine one or more characteristics of a specimen. For example, the system shown in FIG. 1 is configured to inspect a specimen. In some embodiments, the system is configured as a bright field (BF) inspection system. In this manner, the system may be configured for BF inspection of the specimen. In addition, or alternatively, the system may be configured as a dark field (DF) inspection system. As such, the system may be configured for DF inspection of the specimen. For example, the system shown in FIG. 1 may include a BF channel and a DF channel. However, the inspection system may include a BF channel or a DF channel. The BF channel and the DF channel are configured to generate inspection output and/or other output for the specimen.

It is noted that FIG. 1 is provided herein to generally illustrate one embodiment of a configuration for the system. Obviously, the system configuration described herein may be altered to optimize the performance of the system as is normally performed when designing a commercial inspection or other measurement system. In addition, the systems described herein may be implemented using an existing inspection or other measurement system (e.g., by adding one or more light sources described herein to an existing inspection system or replacing one or more light sources of an existing inspection system with one or more light sources described herein). Alternatively, the system described herein may be designed "from scratch" to provide a completely new system.

The system shown in FIG. 1 includes light source 10 (i.e., an illumination source). Light source 10 may be configured according to any of the embodiments described herein. In particular, light source 10 is an electrodeless lamp configured to generate light. More specifically, the electrodeless lamp includes a plasma (not shown in FIG. 1) that generates light. In addition, as described further herein, the system includes a laser (not shown in FIG. 1) configured to generate excitation light and focusing optics (not shown in FIG. 1) configured to focus the excitation light to the plasma in the electrodeless lamp such that the plasma generates light. The laser, the focusing optics, the plasma, and the electrodeless lamp may be further configured according to any of the embodiments described herein.

The system may also include two or more light sources (not shown). The two or more light sources may be configured similarly or differently. For example, the light sources may be configured to generate light having different characteristics (e.g., wavelength, polarization, etc.) that can be directed to a specimen at the same or different angles of incidence and at the same or different time. The two or more light sources may be configured according to any of the embodiments described herein. In addition, one of the light sources may be configured according to any of the embodiments described herein, and another light source included in the system may include any other light source known in the art (e.g., a laser).

The system also includes an illumination subsystem configured to illuminate the specimen with the light generated by the plasma. For example, the illumination subsystem may include one or more optical elements configured to direct the light to the specimen. In one such example, the one or more optical elements may include beam splitter 12 and objective 14. Beam splitter 12 is configured to direct light from light source 10 to objective 14. Objective 14 is configured to focus the light from beam splitter 12 onto specimen 16 at a substantially normal angle of incidence. However, the system may be configured to direct the light to the specimen at any suitable angle of incidence. Beam splitter 12 may include any appropriate optical component known in the art. Objective 14 may include any appropriate refractive optical component known in the art. In addition, although objective 14 is shown in FIG. 1 as a single refractive optical component, objective 14 may include one or more refractive optical components and/or one or more reflective optical components.

In one embodiment, the specimen includes a wafer. In another embodiment, the specimen includes a patterned wafer. In an additional embodiment, the specimen includes a reticle. Therefore, the system may be configured for inspection of a wafer, a patterned wafer, and a reticle. The specimen may be further configured as described herein.

The system also includes a detection subsystem configured to generate output responsive to light from the specimen due to illumination of the specimen. The detection subsystem may include multiple, independent detection channels. Each detection channel is configured to collect light scattered or reflected from the specimen under test over a unique set of collection angles. In addition, although embodiments are described further herein as including a BF channel and a DF channel, the detection subsystem may include any combination of one or more detection channels (e.g., one BF channel and/or one or more DF channels). Moreover, the detection subsystem may include a number of detection channels, and output generated by all of the detection channels or fewer than all of the detection channels may be used by a processor as described further herein. The output generated by a particular combination of detection channels that is used by a processor as described further herein may be selected based on, for example, characteristics of the specimen, characteristics of the defects of interest, and characteristics of the system.

In the embodiment shown in FIG. 1, light reflected from specimen 16 is collected by objective 14 and passes through beam splitter 12 to detector 18. Detector 18 may include any appropriate detector known in the art. Detector 18 is configured to generate output for specimen 16. In addition, detector 18 may include an imaging detector. Therefore, the output generated by detector 18 may include image data. As shown in FIG. 1, objective 14 is configured to collect light specularly reflected from the specimen, and detector 18 is configured to detect light specularly reflected from the specimen. Therefore, objective 14 and detector 18 form the BF channel of the system. As such, the BF channel of the system is configured to generate output for the specimen. In addition, the BF channel of the system may be configured to generate output that includes image data.

Light scattered from specimen 16 is collected by objective 20, which directs the collected light to detector 22. Objective 20 may include any appropriate refractive optical component known in the art. In addition, although objective 20 is shown in FIG. 1 as a single refractive optical component, objective 20 may include one or more refractive optical components and/or one or more reflective optical components. Objective 20 may be configured to collect light scattered from the specimen at any suitable scattering angles. The scattering angles at which objective 20 is configured to collect light scattered from the specimen may be determined based on one or more characteristics (e.g., of patterned features (not shown) or defects of interest (not shown)) of the specimen.

Detector 22 may include any appropriate detector known in the art. Detector 22 is configured to generate output for specimen 16. In addition, detector 22 may include an imaging detector. Therefore, the output generated by detector 22 may include image data. As shown in FIG. 1, objective 20 is configured to collect light scattered from the specimen, and detector 22 is configured to detect light scattered from the specimen. Therefore, objective 20 and detector 22 form the DF channel of the system. As such, the DF channel of the system is configured to generate output for the specimen. In addition, the DF channel of the system may be configured to generate output that includes image data.

In some embodiments, the BF channel and the DF channel are configured to generate the output in the deep ultraviolet (DUV) spectrum. For example, as described further herein, light source 10 may be configured to generate light in the DUV spectrum. In addition, detectors 18 and 22 may be configured to detect light reflected and scattered, respectively, in the DUV spectrum. However, the BF and DF channels may also or alternatively be configured to generate the output in any other suitable spectrum (e.g., DUV, ultraviolet (UV), visible, vacuum ultraviolet (VUV), or some combination thereof), which may vary depending on, for example, the spectral region in which light source 10 generates light.

During generation of the output by the BF and DF channels of the system, specimen 16 may be disposed on stage 24. Stage 24 may include any appropriate mechanical and/or robotic assembly known in the art (e.g., a scanning stage configured to support the specimen under test).

The system may also include processor 26. Processor 26 may be coupled to detectors 18 and 22 such that the processor can receive output from detectors 18 and 22. Processor 26 may be coupled to the detectors in any suitable manner known in the art (e.g., via a transmission medium (not shown) that may include "wired" and/or "wireless" portions, via electronic components (not shown) interposed between each of the detectors and the processor, etc.).

The output generated by the detection subsystem (e g., output generated by detectors 18 and/or 22) can be used to determine one or more characteristics of specimen 16. For example, processor 26 may be configured to use the output generated by the detection subsystem to detect defects on the specimen (thereby determining one or more characteristics of the specimen such as whether or not defects are present on the specimen, number of defects on the specimen, locations of defects on the specimen, etc.). The processor may be configured to detect the defects on the specimen and to determine one or more characteristics of the specimen using the output and any appropriate method and/or algorithm known in the art. The processor may also be configured to perform any other step(s) of any other method(s) described herein.

Processor 26 may take various forms, including a personal computer system, mainframe computer system, workstation, image computer, parallel processor, or any other device known in the art. In general, the term "computer system" may be broadly defined to encompass any device having one or more processors, which executes instructions from a memory medium.

The system shown in FIG. 1 may also include any other suitable components (not shown) known in the art. Furthermore, light sources described herein can be used in a commercially available inspection system such as the 2360, 2365, 2371, 23xx, and 28xx systems that are available from KLA-Tencor, San Jose, Calif. In addition, the electrodeless lamp embodiments described herein may be used in any other appropriate system, some examples of which are illustrated in U.S. Pat. No. 5,864,394 to Jordan III et al., U.S. Pat. No. 6,313,467 to Shafer et al., U.S. Pat. No. 6,633,831 to Nikoonahad et al., U.S. Pat. No. 6,862,096 to Vaez-Iravani et al., and U.S. Pat. No. 6,879,391 to Danko, which are incorporated by reference as if fully set forth herein.

Furthermore, the system shown in FIG. 1 may be configured and used as a defect review system (i.e., as a system configured to "revisit" defects detected on the specimen to determine additional information about the defects such as defect type). For example, the defect review system may be configured to perform defect review of a specimen by generating a relatively high magnification image of the defects detected on the specimen (e.g., by using the BF channel described above to acquire such an image) such that additional information about the defects can be determined (e.g., by the processor described above) using the relatively high magnification image. Therefore, the one or more characteristics of the specimen determined by the system may include one or more characteristics of defects detected on the specimen. The one or more characteristics of the defects may be determined using any method and/or algorithm known in the art.

Moreover, the system shown in FIG. 1 may be configured and used as a metrology system (i.e., as a system configured to measure one or more characteristics of one or more patterned features formed on the specimen). In one such embodiment, the one or more characteristics include one or more dimensions of one or more patterned features formed on the specimen. In another embodiment, the one or more characteristics include a shape of one or more patterned features formed on the specimen. The metrology system may be configured to determine these and any other characteristics of the specimens described herein by performing any other measurements known in the art such as optical critical dimension (OCD) measurements.

The embodiments of the system shown in FIG. 1 may be further configured as described herein. In addition, the system may be configured to perform any step(s) of any of the method embodiments described herein. The embodiments of the system shown in FIG. 1 have all of the advantages of other embodiments described herein.

FIG. 1 also illustrates a system configured to provide illumination of a specimen for a process performed on the specimen. The system includes an electrodeless lamp (e.g., light source 10) configured to generate light. The system is further configured such that the light illuminates specimen 16 during the process. For instance, as described above, the system may include an illumination subsystem, which as described above, may include beam splitter 12 and objective 14 that are configured to direct light from light source 10 onto the specimen during the process such that the light illuminates the specimen during the process. In addition, the electrodeless lamp may be configured to direct the light onto the specimen during the process. Furthermore, the system may include any other suitable optical component(s) known in the art configured to direct the light from the electrodeless lamp to the specimen during the process. This system may be further configured as described herein.

The embodiments described herein are generally configured to use one or more electrodeless lamps for patterned wafer inspection, other specimen inspection (unpatterned wafer inspection, reticle inspection), or metrology. In particular, one embodiment of a method for providing illumination of a specimen for inspection includes illuminating the specimen during the inspection with light generated by an electrodeless lamp. This method may include any other step(s) of any other method(s) described herein. The steps of the method may be performed as described herein. The electrodeless lamp used in the method may be configured according to any of the embodiments described herein. In addition, the method may be performed by any of the system embodiments described herein. Furthermore, the embodiment of the method described above has all of the advantages of other embodiments described herein.

In one embodiment, the electrodeless lamp has an emissivity of greater than about 0.1. In another embodiment, the light generated by the electrodeless lamp includes DUV light, UV light, visible light, or some combination thereof. In an additional embodiment, the light generated by the electrodeless lamp includes broadband light. In some embodiments, the light generated by the electrodeless lamp includes light in a band from about 180 nm to about 450 nm. In a further embodiment, the light generated by the electrodeless lamp includes light in a spectral region from about 200 nm to about 450 nm. In yet another embodiment, the electrodeless lamp includes a plasma from which collected radiation between about 200 nm and about 450 nm is greater than about 3 W.

The electrodeless lamp includes an electrodeless produced plasma. In particular, in one embodiment, the electrodeless lamp includes a plasma excited without introducing electrodes or a heat sensitive material near a region of the plasma. Electrodeless produced plasmas can be advantageously used to provide relatively high brightness radiation in the DUV region. In addition, electrodeless produced plasmas can be used to provide substantially high brightness radiation in the DUV, UV, and visible regions, or some combination thereof. This broadband spectral brightness has value for flexible, sensitive wafer inspection today and in the near future. The performance of the electrodeless lamps described herein can be optimized for microelectronics inspection applications in a number of ways. For example, optimizing the operation of DUV electrodeless lamps for use as sources in inspection applications such as semiconductor wafer inspection may include optimizing the pressure, gas type, energy deposition, energy deposition profile, or some combination thereof of the lamp while at the same time eliminating the need for electrodes.

The targeted properties of the plasma-based electrodeless light source may include an energy pumped plasma from a gas or gas mixture, emissivity (hence pressure) of at least about 0.1 (although the emissivity may be about 0.05, about 0.1, about 0.2, etc.), partial pressure in a range of about 1 atm to about 40 atm or at least 1 atm, a plasma range limited to a relatively small volume between about 0.1 mm to about 2 mm (e.g., about 0.5 mm) in any direction to conservatively manage input, an etendue that substantially matches an illumination etendue, a managed heat, temperature of the plasma between about 9,000 K and 20,000 K, a plasma excited in a way that does not introduce electrodes or other heat sensitive materials near the plasma region, and an entire light source assembly configured to allow relatively efficient transmission of light in the wavelength band of about 180 nm to about 450 nm and with sufficient etendue to substantially match the illumination requirements of the inspection system. In one embodiment, therefore, the electrodeless lamp is configured to have an etendue that substantially matches illumination requirements of the system. In addition, the shortest wavelength of light emitted by the lamp embodiments described herein may vary depending on the housing of the lamp embodiments. For example, if the lamp housing is formed of a material that is relatively transparent at wavelengths of about 150 nm and above, the lamp may be configured for inspection applications at wavelengths of about 150 nm and above. Therefore, the electrodeless lamps described herein may be used to provide light in the VUV wavelength range in addition to or instead of light in other wavelength ranges described herein.

Briefly, some advantages of using an electrodeless lamp as a relatively high brightness source include: a) elimination of electrodes in the lamp provides a lamp that does not degrade in time; b) the elimination of electrodes allows the lamp to be designed so that substantially all of the excitation energy can be deposited in the region of the lamp in which energy is collected by an illumination subsystem or lamp optics; c) the geometry of the plasma can be shaped to substantially match that of the collection optics; d) a cylindrical geometry can be generated which, when observed axially, can produce a lamp brightness in excess of that available from a spherically symmetric source; e) higher brightnesses can be achieved compared to electrode produced plasmas due to 1) the ability to concentrate an excitation source in the region of interest thereby not having to contend with repelling electrons in the excitation region and 2) the ability to achieve substantially higher excitation power densities and hence temperatures; f) ohmic losses in the lamp (e.g., unused ohmic losses in the electrodes of currently used lamps) are substantially eliminated making for a higher efficiency lamp; and g) the elimination of electrodes eliminates a relatively large source of short term and long range degradation and, importantly, variability and noise in lamp output and spectrum.

In one embodiment, the electrodeless lamp includes a plasma generated using a single gas. In a different embodiment, the electrodeless lamp includes a plasma generated using a combination of gases. In another embodiment, the electrodeless lamp is filled with a gas that includes argon (Ar), krypton (Kr), xenon (Xe), fluorine (F), F dimers, chlorine (Cl), Cl dimers, mercury (Hg), nitrogen trifluoride ($NF_3$), sulfur hexafluoride ($SF_6$), a rare gas, a rare earth gas, a transition metal gas, a lanthanide metal gas, a halide containing gas, a Hg halide gas, or some combination thereof.

In one example, nontraditional fill gases may be used in an electrodeless lamp for DUV inspection applications in which the wavelengths of interest are roughly in the spectral region from about 200 nm to about 450 nm. In addition to commonly used gases such as Ar, Kr, Xe, and Hg, gases such as Cl dimers, F dimers, rare earths, transition metals, and lanthanide metals are capable of providing substantially favorable working media in this wavelength range. These materials may be introduced to the lamp in the form of molecular species with relatively high vapor pressures. Example of appropriate gases also include, but are not limited to, Hg halides, $NF_3$, $SF_6$, diatomic halogens such as diatomic chlorine ($Cl_2$), and a host of other combination gases. These gases will only be present as atomic constituents within the relatively high temperature plasma, and their emission can be optimized in the wavelength range of about 200 nm to about 450 nm, for example, by varying the plasma temperature. Feed material (fill materials at room temperature), which are atomic already or which are diatomic gases of a single atomic species, furthermore, will not be consumed in the apparatus.

In one embodiment, the light generated by the electrodeless lamp includes excimer radiation. In one such embodiment, the electrodeless lamp includes about 1 bar or more of background rare gas and about 1 bar or less of a halide containing gas. For example, gas mixtures of Ar and F, in the case of relatively high background pressure or partial pressure (1 bar roughly or more) of Ar, will advantageously give rise to excimer emission (emission of F on a background of Ar) in a relatively copious quantity. In addition, unlike excimer laser light sources, the excimer emission of the lamp embodiments described herein is incoherent emission. Furthermore, unlike excimer laser light sources that produce narrowband light, the lamp embodiments described herein produce broadband light. Therefore, mixtures of Ar or Kr, for example, with diatomic halide species are particularly attractive feed materials.

Ideal gases for use in embodiments described herein may have relatively high absorption of light at a wavelength of about 1 µm in the plasma state, relatively high emissivity at wavelengths from about 250 nm to about 400 nm, relatively low emissivity outside of wavelengths from about 250 nm to about 400 nm, ignite relatively easily, and do not substantially attack the glass or other materials of the lamps and do not leak out of the glass or other materials of the lamp.

The plasma temperature in the region of highest brightness can be readily controlled and held substantially constant using excitation source pumped plasmas. It may also be desirable to optimize the brightness and average power of the lamp without exceeding a blackbody temperature that would produce substantial amounts of "out of band" DUV radiation above the bandgap for absorption of common UV transparent materials such as fused silica, magnesium fluoride ($MgF_2$), and similar materials. For example, while temperatures as high as about 50,000 K can be achieved in discharges (e.g., radio frequency (RF) excited discharges and light produced discharges at relatively high pump powers and tight focus), it is important to recognize that above about 20,000 K the amount of blackbody radiation produced above the bandgap of the containing envelope of the lamp, whether the envelope is formed of fused silica, $MgF_2$, lithium fluoride (LiF), or other UV transparent materials, is sufficiently high such that the envelope will absorb the radiation and fracture or melt. Nearly three orders of magnitude more radiation within absorbing regions of fused silica is produced in a temperature range of about 25,000 K to about 50,000 K than the 10,000 K plasma range. Accordingly, exciting the plasma to temperatures between about 10,000 K and about 20,000 K is easily achieved and maintained in a properly designed electrodeless pumped plasma.

Configuring the focus of the excitation source or excitation sources used to sustain the plasma action appropriately is advantageous. In particular, inspection systems most efficiently collect and deliver light to the specimen plane using certain plasma shapes and sizes. For BF inspection systems used beyond the year 2005, shrinking pixel sizes and increased imaging computer inspection speeds will demand that plasmas roughly 1 mm in diameter are provided. In one embodiment, the electrodeless lamp includes a cylindrically shaped plasma substantially matched to image onto the specimen in the system. For example, "hockey puck" geometries in which the thickness of the puck is substantially matched to the depth of focus in the system and the puck diameter is roughly about 1 mm or a couple of hundred of µm are preferred. Therefore, relatively high numerical aperture (NA) short focal length delivery from one or more excitation sources are expected to best approach this geometry.

Light generated by a plasma that has a generally ellipsoidal shape may be directed to one or more reflectors or other optical components of the illumination subsystem that direct only some cylindrical section of the light generated by the plasma to the specimen. This cylindrical section of the light may be directed or reflected in some nearly parallel way to a mirror, condenser, homogenizer, or some combination thereof. The illumination optics used in the system for the lamp embodiments described herein may be selected such that about π sr from an about 4π sr plasma is directed to the specimen. In this manner, the entire cross-section of light generated by the plasma may not be directed to the specimen.

In another embodiment, an excitation volume of the electrodeless lamp is substantially matched to a field of view of collection optics of a system configured to inspect the specimen. In one embodiment, the electrodeless lamp includes a plasma region having a volume of about 0.1 mm to about 2 mm in any direction. In an additional embodiment, the electrodeless lamp includes a plasma having a geometry shaped to substantially match collection optics of a system configured to inspect the specimen. In this manner, the plasma excitation may be shaped such that the excitation volume of the plasma is substantially matched to the collection optics field of view appropriate for inspection such as wafer and/or reticle inspection.

The field of view on the wafer may have a shape such as a rectangular, square, or circular shape. In addition, the field of view on the wafer may be about 1000 pixels to about 8000 pixels wide. The size of the pixels may be about 50 nm to about 300 nm depending on the inspection application and inspection system configuration. The NA may be up to about 0.9. In addition, higher brightness is desirable as the etendue decreases.

In some embodiments, the light from the lamp may not be directed to the specimen across all of the solid angles encompassed by the NA. Instead, the light from the lamp may be directed to the specimen across a "ring" within the NA that subtends a solid angle of about 10 degrees to about 15 degrees, which may vary depending on the NA of the illumination subsystem of the inspection system.

In one embodiment, a system described herein includes one or more electrodeless lamps at pressures above about 0.5 atm (at their working temperatures) that are configured to produce light for inspection (e.g., wafer inspection). In some embodiments, the lamp(s) produce light in the region of wavelengths between about 200 nm and about 400 nm. For example, in one embodiment, the electrodeless lamp is at a pressure of above about 1 atm at a working temperature of the electrodeless lamp, and the light generated by the electrodeless lamp includes light in a spectral region from about 200 nm to about 400 nm.

In another embodiment, the light generated by the electrodeless lamp has a spectral brightness exceeding about 2 $W/mm^2$-sr in an integral region of an electromagnetic spectrum from about 200 nm to about 400 nm. In this manner, the system may include one or more electrodeless lamps as light source(s), and the one or more electrodeless lamps may have spectral brightness exceeding about 2 $W/mm^2$-sr in the integral region of the electromagnetic spectrum from about 200 nm to about 400 nm. In addition, the one or more electrodeless lamps may have spectral brightness of about 10 $W/mm^2$-sr to about 40 $W/mm^2$-sr. In a further embodiment, the electrodeless lamp(s) are configured to generate in excess of about 3 W of average power within any band contained within the region between about 200 nm and about 450 nm. In this manner, in some embodiments, light generated by the electrodeless lamp has an average power in excess of about 3 W within any band in a region between about 200 nm and about 450 nm. Therefore, the electrodeless lamps described herein may be configured to generate broadband light that can be used for broadband inspection of a specimen. In addition, the electrodeless lamps are configured to generate incoherent light.

In one embodiment, the electrodeless lamp includes a plasma driven by an oscillatory magnetic field. In another embodiment, the electrodeless lamp includes a plasma driven by an oscillatory electric field. In this manner, the excitation source may include an electromagnetic excitation source. For example, the electromagnetic excitation source may be an RF source that can generate about a 1 GHz to many GHz electric field. In another example, the electromagnetic excitation source may be a microwave cavity that is configured to generate electric and magnetic fields. The electromagnetic excitation source may function as a relatively high power amplifier that is focused to a relatively small region proximate the plasma. In a different embodiment, the excitation source includes an electron source. For example, the electron source may be an electron gun. Electrodeless lamps that include plasmas driven by an oscillatory magnetic or electric field may be further configured as described herein.

In some embodiments, the system includes an excitation source for the excitation of the plasma(s) in the electrodeless lamp(s) in cylindrical geometries such that the plasma axis length does not produce an average plasma opacity over this region of greater than one e-folding from "end-cap" to "end-cap." In this manner, the electrodeless lamp may include a plasma having a plasma axis length, and the plasma does not produce an average plasma opacity over the plasma axis length of greater than about 1 e-folding from one end cap to another end cap of the electrodeless lamp.

In another embodiment, the system is configured to use excitation from one or more excitation sources to form disc or hockey puck shaped plasmas that are relatively well matched to image onto the wafer plane in inspection systems. In a further embodiment, the electrodeless lamp includes a plasma having a diameter of between about 100 µm and about 2 mm. In an additional embodiment, the system is configured to use one or more excitation sources to ignite a plasma in the electrodeless lamp, and the power of the excitation source(s) is in excess of about 100 W.

In some embodiments, the system is configured to use one or more "igniter" electrodes in conjunction with the overall electrodeless produced plasma. These one or more electrodes may be used to reduce the intensity of the excitation source that initiates the plasma. In a further embodiment, the electrodeless lamp includes an electrodeless produced plasma in which the collected radiation between about 200 nm and about 450 nm is more than about 3 W.

In an additional embodiment, one or more materials are introduced to the lamp(s). The one or more materials may include fill gases such as Ar, Kr, Xe, F, Cl, $NF_3$, $SF_6$, any other rare gas or halide containing gas, or some combination thereof. In another embodiment, the electrodeless produced plasma is configured to produce excimer radiation by using about 1 bar or more of background rare gas along with a similar or lower fill pressure (i.e., the initial or cold pressure) of halide containing gas. In one embodiment, the electrodeless lamp has a partial pressure in a range of about 1 atm to about 40 atm. In another embodiment, a fill pressure of gases in the electrodeless lamp is about 4 atm or higher. In some embodiments, the lamp is configured for fill pressures of gases to as much as about 10 atm or about 10 bar. In another embodiment, the lamp is configured for fill pressures of gases to as much as about 4 atm to about 10 atm or bar or higher. Higher fill pressures may be advantageous to increase the excitation of the plasma, which may increase the average power that can be achieved by the plasma. In other words, using higher fill pressures may advantageously increase the ratio of absorbed power to radiated power of the plasma. In one embodiment, the electrodeless lamp includes a plasma generated using a rare earth gas and a Hg gas. In one such embodiment, the light generated by the electrodeless lamp is in a spectral region from about 230 nm to about 480 nm. The electrodeless lamp may include an electrodeless produced plasma that includes a combination of rare earth (e.g., Xe, Ar, etc.) and Hg gases to optimize spectral brightness in the wavelength region of about 230 nm to about 480 nm. For example, the electrodeless produced plasma may include about 1 atm fill of Ar, about 4 atm or higher fill of Ar, about 1 atm fill of Xe, about 4 atm or higher fill of Xe, a combination of Hg and Xe, and about 1 atm fill of Xe with $Cl_2$.

In some embodiments, a fill gas in the electrodeless lamp has an opacity at a working temperature and pressure of the electrodeless lamp that does not exceed about 10% reabsorption of about 200 nm to about 450 nm radiation emitted from a center of the electrodeless lamp. In this manner, the opacity of fill gases used in the electrodeless lamp at the working temperature and pressure of the lamp does not exceed about 10% reabsorption of about 200 nm to about 450 nm radiation emitted from the center of the lamp.

In another embodiment, a temperature of the plasma in the electrodeless lamp is between about 10,000 K and about 30,000 K for any of the fill gases described herein. In one embodiment, therefore, the electrodeless lamp includes a plasma at a temperature of about 10,000 K to about 30,000 K. However, in a different embodiment, the electrodeless lamp includes a plasma at a temperature of about 9,000 K to about 20,000 K.

In one embodiment, the electrodeless lamp is substantially flat on one side and has a substantially hemispherical shape. For example, the electrodeless lamp may be substantially flat on one side (e.g., such that the lamp has a shape approximately similar to a hemisphere) to reduce the distance between the entrance of the excitation source to the working medium and its focal point. This concept and related bulb design concepts may be employed to optimize the shape of the plasma to the collector of the inspection system. In one embodiment, therefore, the electrodeless lamp includes a bulb configured to optimize a shape of a plasma within the bulb to a collector of a system configured to inspect the specimen.

In one embodiment, the electrodeless lamp includes a bulb in which a focusing element is disposed such that the electrodeless lamp is further configured for substantially high NA focus. For example, in some embodiments, the electrodeless lamp includes a bulb with an internal lens or curved reflector to achieve relatively high NA focus. In addition, the plasma source may be positioned at approximately the center of a spherical reflector that will redirect some light generated by the plasma back into the plasma thereby causing further heating of the plasma. While the plasma may be relatively optically thin (and not substantially absorptive), if the Q of the cavity is relatively high (e.g., not much loss in the reflector or in the quartz bulb) then there are chances for photons to be absorbed in the plasma. For example, the plasma will radiate over almost $4\pi$ sr, but about $\pi$ sr of the light may be collected. Therefore, the uncollected light may be used to reheat the plasma and drive up the temperature and brightness. The spherical reflector may have holes formed therethrough to allow for the collection of the light, but these holes may not reduce the Q much for photons that are bouncing back and forth across the spherical reflector away from the collection optics until they get absorbed by the plasma. To optimize this effect, the absorption at the reflector (1-R) may be small compared to the absorption at the plasma. As such, the reflector may have a substantially high R at the wavelengths at which the plasma radiates. The bulb wall absorption losses are also preferably relatively low for this to work well as high absorption at the bulb wall would reduce the overall cavity Q. This effect may combat the effect of the plasma burning away from the focal point of the excitation source. Pumping with reflected light over a substantially large NA would tend to counteract this effect.

There are additional ways to excite a relatively high pressure, spatially limited plasma. For example, an RF electrical amplifier may be configured to drive a tuned inductor (e.g., a Helmholtz coil) or capacitor to create substantially large oscillatory magnetic and electric fields, respectively. A critical field strength will cause ionization and the resulting oscillatory electrons will drive plasma temperature in the same way that electrons drive discharge arc or inductive loop based plasma sources.

Figure 2:
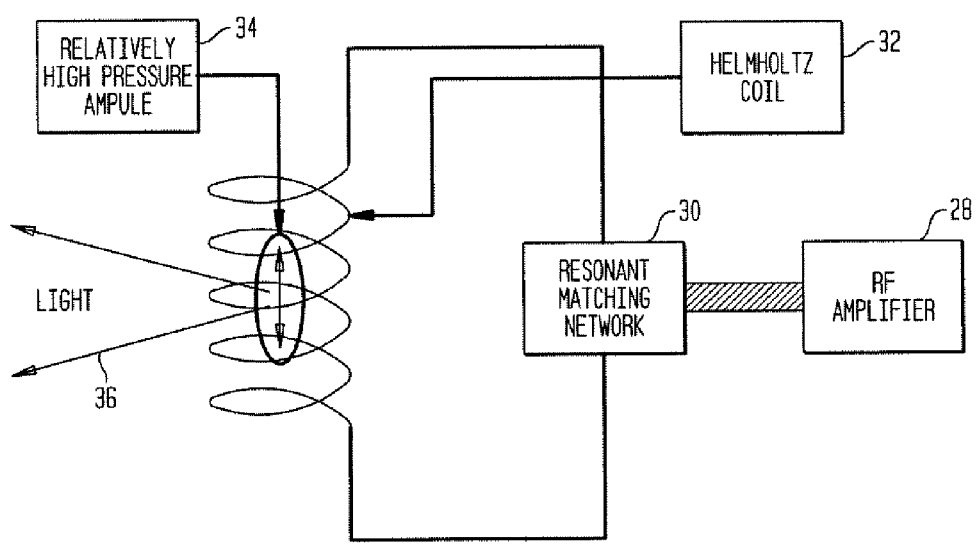
FIGS. 2 and 3 are schematic diagrams illustrating a side view of various embodiments an electrodeless lamp.
Figure 3:
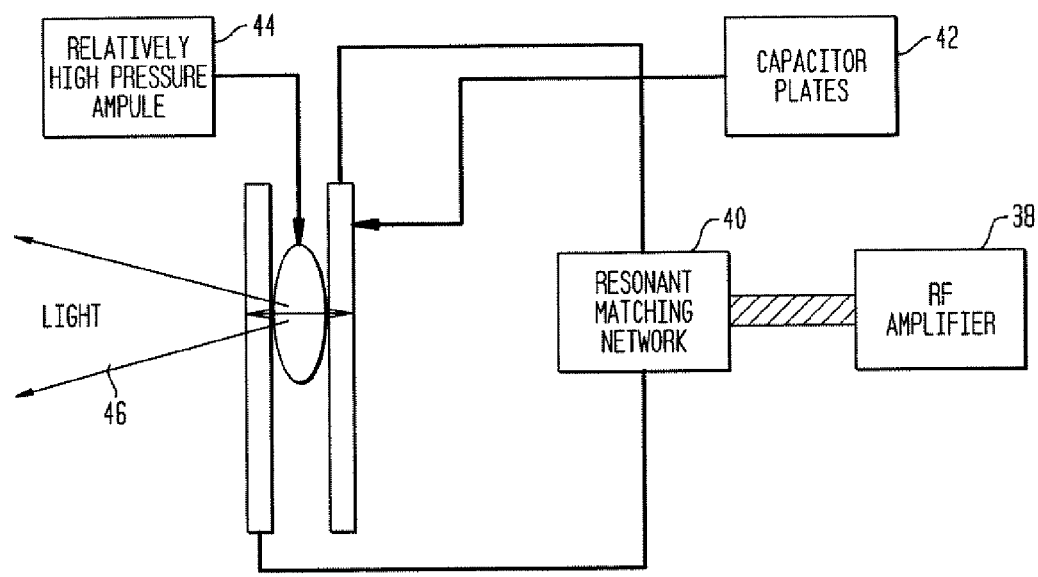

FIGS. 2 and 3 illustrate various embodiments of an electrodeless lamp. In particular, FIG. 2 illustrates one method for delivering excitation power to a contained relatively small, relatively high pressure plasma. In this embodiment, a relatively high power amplifier is used to create focus to a relatively small region. As shown in FIG. 2, this embodiment of an electrodeless lamp includes RF amplifier 28 coupled to resonant matching network 30. The RF amplifier and the resonant matching network may include any suitable components known in the art. The resonant matching network may be configured to operate at about 50 ohms. The resonant matching network is coupled to Helmholtz coil 32 to create a relatively high strength oscillatory magnetic field. The Helmholtz coil may include any suitable Helmholtz coil known in the art.

Relatively high pressure ampule 34 (having dimensions of about 1 mm by about 2 mm and having a roughly ellipsoidal shape) contains the plasma gas mixture. The ampule may have any other suitable configuration. The plasma gas mixture may include any of the gas mixtures described herein. As further shown in FIG. 2, light 36 is output from the ampule, which may include DUV light UV light, visible light, or some combination thereof. The embodiment of the electrodeless lamp shown in FIG. 2 may be further configured as described herein. The embodiment of the electrodeless lamp shown in FIG. 2 may be included in any of the systems described herein. In addition, the embodiment of the electrodeless lamp shown in FIG. 2 has all of the advantages of other embodiments described herein.

FIG. 3 illustrates another method for delivering excitation power to a contained relatively small, relatively high pressure plasma. As shown in FIG. 3, this embodiment of an electrodeless lamp includes RF amplifier 38 coupled to resonant matching network 40. The RF amplifier and the resonant matching network may include any suitable components known in the art. The resonant matching network may be configured to operate at approximately 50 ohms. The resonant matching network is coupled to capacitor plates 42 that are configured to create a relatively high strength oscillatory electric field. In this manner, electromagnetic sources may be used to drive RF to a many GHz resonant electric field. In a similar manner (not shown), electromagnetic sources may be used to drive microwave cavities with electric and magnetic fields. The capacitor plates may have any suitable configuration known in the art.

Relatively high pressure ampule 44 (having dimensions of about 1 mm by about 2 mm and having a roughly ellipsoidal shape) contains the plasma gas mixture. The ampule may have any other suitable configuration. The plasma gas mixture may include any of the gas mixtures described herein. As further shown in FIG. 3, light 46 is output from the ampule, which may include DUV light, UV light, visible light, or some combination thereof. The embodiment of the electrodeless lamp shown in FIG. 3 may be further configured as described herein. The embodiment of the electrodeless lamp shown in FIG. 3 may be included in any of the systems described herein. In addition, the embodiment of the electrodeless lamp shown in FIG. 3 has all of the advantages of other embodiments described herein.

The configuration of the electrodeless lamps described herein may be further selected based on Babucke et al., J. Phys. D, App. Phys. 24 1316 (1991), Derra et al., J. Phys. D, App. Phys., 38 2995, A. T. M. Wilburs and D. C. Schram, S. Quant. Spec. and Radiat. Transfer, 46 299-308 (1991), and D. Erskine et al., J. Quant. Spec. and Radiat. Transfer, 51(12), 97-100 (1994), which are incorporated by reference as if fully set forth herein.

The following description generally relates to electrodeless lamps configured as laser sustained plasma (LSP) lamps or LSP light sources (LSPLSs) that may be optimally configured for wafer inspection and other applications described herein. The terms "electrodeless lamp," "LSP lamp," "LSP light source" and "LSPLS" are used interchangeably herein.

Substantially high brightness and substantially high average power lamps are highly desired as sources that can provide DUV radiation for illumination and inspection of semiconductor wafers and other specimens described herein. As semiconductor transistor dimensions continue to shrink with CDs approaching several tens of nanometers, wavelengths well below about 300 nm are essential for the resolution of defects. Relatively large bandwidth lamps are attractive for such applications due to their ability to reduce color variations (e.g., reflectivity differences due to thin film stack thickness variation) and optimize contrast by selecting desirable bands for various material types within the lamp spectrum. Selecting spectral bands for different materials types can be performed as described in commonly assigned U.S. patent application Ser. No. 10/410,126 by Lange et al., filed Apr. 4, 2003, published as U.S. Patent Application Publication No. 2004/0201837 on Oct. 14, 2004, and commonly assigned U.S. patent application Ser. No. 10/933,873 to Lange et al., filed Sep. 3, 2003, published as U.S. Patent Application Publication No. 2005/0052643 on Mar. 10, 2005, all of which are incorporated by reference as if fully set forth herein. However, brightness far exceeding that of 1 kW commercial lamps (about 1 $W/mm^2$-sr to about 5 $W/mm^2$-sr for wavelengths from about 230 nm to about 370 nm) is greatly desired to provide the brightest possible illumination within the field of view of the optical inspection microscope. Illumination with a source sufficiently bright to saturate the inspection system sensor generally provides the highest sensitivity to defects. In addition, extremely high brightness DUV sources allow the reduction of inspection time (and thereby increased throughput) by effecting saturation of the sensor on the smallest timescales possible (subject to limits for preventing wafer and microscope damage).

However, electrically driven lamps have brightness and average power limits due to the inability of such lamps to contain the energy deposition from electrodes within a relatively small volume due to electron-electron repulsion, the limited emissivity of gases as black body emitters, the rapid erosion of electrodes made from refractory materials due to the presence of relatively large current densities at the cathodes, and the inability to contain dopants for relatively long periods of time within refractory cathodes in order to lower the operating temperature of the cathodes at the required emission current.

At the same time, additional methods of exciting gases to energies and energy densities capable of substantially high brightness DUV emission are available. In particular, laser excitation of relatively high pressure atomic and molecular vapor can provide substantially intense DUV light. Indeed, lithography tool manufacturers have for nearly 15 years been pursuing the development of a so-called extreme UV (EUV) light source in which laser produced (or discharge produced) plasmas are used to pump highly ionized atoms to a degree such that they efficiently provide radiation at a wavelength of 13 nm. Sources obtained by direct pulsed laser excitation are substantially expensive however; too expensive for wafer inspection tools. Fortunately, it has been known for over 30 years that continuous-wave (cw) sustained laser plasmas can provide substantially efficient production of DUV radiation for applications including those discussed herein (see, for example, D. L. Franzen, J. Appl. Phys. 44(4), 1727-1732 (1972) and D. L. Franzen, Appl. Phys. Lett., 21, 62-64 (1972), which are incorporated by reference as if fully set forth herein).

The embodiments described herein may be configured to optimize the operation of DUV lamps and the delivery of their DUV radiation to optical objectives for their use as sources in semiconductor wafer inspection applications and other applications described herein. Such optimization may be achieved by optimizing the pressure, gas type, energy deposition, energy deposition profile, or some combination thereof of the lamp to efficiently couple light generated by the lamp to a standard wafer inspection objective with a time delay integration (TDI) sensor or any other suitable sensor known in the art, which is used to measure the reflected or scattered radiation from the illuminated wafer plane.

Prior to describing the embodiments further, it is noted that a substantial body of literature exists which supports the design of LSPs for applications described herein and subsequent design and optimization for such applications. A great number of authors (see, for example, R. Wiehle, B. Witzel, H. Helm, and E. Cormier, Phys. Rev. A, 67, 063405 (2003) and V. V. Kostin, R. B. Borisov, I. V. Degtyarev, and V. E. Fortov, Phyzika Plasmy 23 (2), 102-109, 1997, both of which are incorporated by reference as if fully set forth herein) have noted that extremely intense fields (e.g., about multi-gigawatt/$cm^2$ laser radiance) are required to initiate breakdown (plasma formation) in a standing or flowing bulk gas composed of primarily ground electronic state species. However, a great many authors have measured the cross section for ionization of highly excited, often metastable, electronic states of neutral atoms and molecules (see, for example, A. Takahashi, T. Okada, T. Hiyama, M. Maeda, K. Uchino, R. Nohdomi, and H. Mizoguchi, App. Phys. Lett., 77(25), 4115-4117 (2000), H. Tanaka, A. Takahashi, T. Okada, M. Maerda, K. Uchino, T. Nishisaka, A. Sumitani, and H. Mizoguchi, Appl. Phys. B, 74, 323-326 (2002), A. Takahashi and T. Okada, Jap. Journ. Appl. Phys., 37, Part 2, No. 4A, L390-L393, (1998), D. L. Franzen, J. Appl. Phys. 44(4), 1727-1732 (1972), D. L. Franzen, Appl. Phys. Lett., 21, 62-64 (1972), and S. Schohl, D. Klar, T. Kraft, H. A. J. Meijer, M-W. Ruf, U. Schmitz, S. J. Smith, and H. Hotop, Zeit. fur Physik D, Atoms, Molecules and Clusters, 21(1) 25-39 (1991), all of which are incorporated by reference as if fully set forth herein) and have found that lower fluences can be used to sustain plasmas that have been initiated by other means. These fluences are more likely in the range of about 1 MW/$cm^2$ and therefore can be formed using currently available low cost cw lasers of various types. Applications investigated have included LSPs for excimer laser radiation production (see, for example, A. Takahashi and T. Okada, Jap. Journ. Appl. Phys., 37, Part 2, No. 4A, L390-L393, (1998), A. Takahashi, T. Okada, T. Hiyama, M. Maeda, K. Uchino, R. Nohdomi, and H. Mizoguchi, App. Phys. Lett., 77(25), 4115-4117 (2000), and H. Tanaka, A. Takahashi, T. Okada, M. Maerda, K. Uchino, T. Nishisaka, A. Sumitani, and H. Mizoguchi, Appl. Phys. B, 74, 323-326 (2002), all of which are incorporated by reference as if fully set forth herein), supersonic plasma jets for propulsion applications (see, for example, Z. Szymanski and S. Filipkowski, J. Appl. Phys., 69(6), 3480-3484 (1990), Z. Szymanski, Z. Peradzynski, J. Kurzyna, J. Hoffman, M. Dudeck, M. ee Graaf, and V. Lago, J. Phys. D: App. Phys. 30, 998-1006 (1997), and J. M. Girard, A. Lebehot, and R. Compargue, J. Phys. D: App. Phys. 26, 1382-1393 (1993), all of which are incorporated by reference as if fully set forth herein), the production of electron sources (see, for example, A. B. Lewis, D. F. Grosjean, and P. Bletzinger, 2nd Inter. Conf on Plasma Science IEEE, p. 45 (1975), which is incorporated by reference as if fully set forth herein), and the detection of metastable atoms (see, for example, J. E. Daily, R. Gommers, E. A. Cummings, D. S. Durfee, and S. D. Bergeson, Phys. Rev. A, 71, 043406 (2005), which is incorporated by reference as if fully set forth herein) to name just a few.

In one embodiment, the systems described herein are configured for patterned wafer inspection. For example, in one embodiment, the light generated by the plasma has a brightness of about 10 W/$mm^2$-sr to about 50 W/$mm^2$-sr in a spectral region from about 200 nm to about 400 nm. In this manner, light driven produced plasmas can be used to provide substantially high brightness radiation in the DUV region (about 10 W/$mm^2$-sr to about 50 W/$mm^2$-sr). This spectral brightness is important for wafer inspection systems on the market today and in the near future. In addition, the performance of these electrodeless lamps can be optimized for the application of microelectronics inspection in a number of ways.

Briefly, some advantages of using light driven or light produced plasmas as relatively high brightness sources are: a) the elimination of electrodes provides for a lamp that does not degrade in time; b) the elimination of electrodes allows for the lamp to be designed so that substantially all of the excitation energy can be deposited in the region of the lamp in which energy is collected by the illumination subsystem or lamp optics; c) the geometry of the plasma can be shaped to substantially match that of the collection optics; d) a cylindrical geometry can be generated which, when observed axially, can produce a lamp brightness in excess of that available from a spherically symmetric source; e) higher brightnesses can be achieved compared to electrode produced plasmas due to 1) the ability to concentrate photons in the region of interest thereby not having to contend with repelling electrons in the excitation region and 2) the ability to achieve substantially higher excitation power densities and hence temperatures; f) ohmic losses in the lamp (e.g., unused ohmic losses in the electrodes of currently used lamps) are substantially eliminated making for a higher efficiency lamp; and g) the elimination of electrodes eliminates a relatively large source of short term and long range degradation and, importantly, variability and noise in lamp output and spectrum.

In one embodiment, the electrodeless lamp includes a fill gas, and the fill gas includes Ar, Kr, Xe, F, Cl, Cl dimers, F dimers, a homogenous diatomic gas, $NF_3$, $SF_6$, nitric oxide (NO), Hg, a halide containing gas, Hg halides, diatomic halides, halides, a rare gas, rare earths, transition metals, lanthanide metals, or some combination thereof. For example, in one embodiment, the electrodeless lamp includes a plasma generated using a single gas. In a different embodiment, the electrodeless lamp includes a plasma generated using a combination of gases. In another embodiment, the electrodeless lamp is filled with a gas that includes Ar, Kr, Xe, F, F dimers, Cl, Cl dimers, Hg, $NF_3$, $SF_6$, a rare gas, a rare earth gas, a transition metal gas, a lanthanide metal gas, a halide containing gas, a Hg halide gas, or some combination thereof. In this manner, fill gases that can be used for the LSP lamps described herein include Ar, Kr, Xe, F, Cl, $NF_3$, $SF_6$, NO, or any other rare gas or halide containing gas, alone or in some combination thereof.

In one example, nontraditional fill gases may be used in LSP lamps for DUV inspection applications in which the wavelengths of interest are roughly in the spectral region from about 200 nm to about 450 nm. In addition to commonly used gases such as Ar, Kr, Xe, and Hg, gases such as Cl dimers, F dimers, rare earths, transition metals, and lanthanide metals are capable of providing substantially favorable working media in this wavelength range. These materials may be introduced to the lamp in the form of molecular species with relatively high vapor pressures. Examples of appropriate gases also include, but are not limited to, Hg halides, $NF_3$, $SF_6$, diatomic halogens such as $Cl_2$, NO, and a host of other combination gases. These gases will only be present as atomic constituents within the relatively high temperature plasmas, and their emission can be optimized in the wavelength range of about 200 nm to about 450 nm, for example, by varying the plasma temperature. Feed materials (fill materials at approximately room temperature), which are atomic already or which are diatomic gases of a single atomic species, furthermore, will not be consumed in the apparatus.

In one embodiment, the light generated by the plasma includes excimer radiation. In one such embodiment, the electrodeless lamp includes about 1 atm or more of background rare gas and about 1 atm or less of a halide containing gas. For example, gas mixtures of Ar and F, in the case of relatively high background pressure or partial pressure (1 bar roughly or more) of Ar, will advantageously give rise to excimer emission (emission of F on a background of Ar) in a relatively copious quantity. In addition, unlike excimer laser light sources, the excimer emission of the embodiments described herein is incoherent emission. Furthermore, unlike excimer laser light sources that produce narrowband light, the embodiments described herein can produce broadband light. Therefore, mixtures of Ar or Kr, for example, with diatomic halide species are particularly attractive feed materials.

Ideal gases for use in embodiments described herein may have relatively high absorption in the plasma state, relatively high emissivity at wavelengths from about 250 nm to about 400 nm, relatively low emissivity outside of wavelengths from about 250 nm to about 400 nm, ignite relatively easily, and do not substantially attack the glass or other materials of the lamp and do not leak out of the glass or other materials of the lamp.

In one embodiment, a temperature of the plasma is held substantially constant by the excitation light. For example, the plasma temperature in the region of highest brightness can be readily controlled and held substantially constant using light driven pumped plasmas. It may also be desirable to optimize the brightness and average power of the lamp without exceeding a blackbody temperature that would produce substantial amounts of "out of band" DUV radiation above the bandgap for absorption of common UV transparent materials such as fused silica, $MgF_2$, and similar materials. For example, while temperatures as high as about 50,000 K can be achieved in discharges (e.g., RF excited discharges and light driven produced discharges at relatively high pump powers and relatively tight focus), it is important to note that above about 20,000 K the amount of blackbody radiation produced above the bandgap of the containing envelope of the lamp, whether the envelope is formed of fused silica, $MgF_2$, LiF, or other UV transparent material, is sufficiently high such that the envelope will absorb the radiation and fracture or melt.

Nearly three orders of magnitude more radiation within absorbing regions of fused silica is produced in a temperature range of about 25,000 K to about 50,000 K than the 10,000 K plasma range. Accordingly, exciting the plasma to temperatures between about 10,000 K and about 20,000 K is easily achieved and maintained in a properly designed light driven pumped plasma. In this manner, the brightness of the lamp and its average power can also be optimized without exceeding a blackbody temperature that would produce substantial amounts of DUV radiation above the bandgap for absorption of common UV transparent materials such as fused silica, $MF_2$, and similar materials, which are preferably used to construct the objective for the inspection system.

A major advantage of LSP lamps is that lasers can deposit the energy of photons in substantially small regions of a relatively high pressure bulb as opposed to the far more diffuse energy deposition of an electrically excited plasma. One result of this extreme concentration of energy is the substantially larger temperature gradients in the lamp from the core of the plasma to the lamp wall. Additionally, substantially higher temperatures are obtainable with LSPs due to the concentration of energy and the elimination of waste heat terms such as ohmic losses and minimization of convective and conductive cooling.

In this manner, the LSP lamps described herein may be configured as relatively high temperature gradient LSP lamps. In particular, the lamps described herein may be operated in a manner that permits relatively intense radiation to be obtained at DUV and even VUV wavelengths that cannot be obtained from electrically sustained lamps. This intense radiation is extremely important and is even new physics and occurs via totally unexpected behavior in these lamps. The embodiments described herein have applications to sub-200 nm optical inspection systems and can even be used to provide 121 nm light and could serve as light sources for the next ten years. A 121 nm light source configured as described herein may be used with an all-reflective objective. Such light sources are advantageous in that e-beam inspection systems would not have to be relied upon for future generations of inspection tools.

The temperature gradient in the LSP lamp is so large that radiation that is normally trapped and completely self-reversed (absent) in electrically driven plasmas is present in abundance in the LSP lamp. For example, it is estimated that several watts of average power can be achieved at about 185 nm and at about 121 nm. Any strong line of an atomic spectrum that terminates upon the ground or low lying (within about a volt) of the ground state can be counted on for relatively strong emission and use in inspection. Such relatively strong emission may also have significant implications for lithography beyond 193 nm immersion lithography.

As a result, strong emission from such plasmas may be obtained on substantially strong atomic transitions that terminate at the ground state or on low (populated) metastable states of the neutral atom (or ion) in the lamp. Whereas the substantially strong resonance line of Hg at 2537 Å is totally missing in electrically driven plasma lamps, this resonance line can be the source of substantially strong emission in laser driven plasmas. This substantially strong resonance line appears to be due to the substantially large Doppler broadening of the atoms in the core of the lamp followed by rapidly diminishing Doppler linewidths in the regions immediately outside of the plasma. As a result, resonance radiation lines are not trapped (although self reversed) and form the basis for substantially high spectral brightness in laser sustained lamps. Therefore, species that once were thought to be of no value in lamps for the production of, for example, UV light can now be used to generate copious amounts of convenient and useful DUV radiation for wafer inspection and other applications described herein.

Example(s) of species of interest include Ba I (neutral barium where I means a neutral atom), which emits resonance lines at 2409 Å, cobalt (Co) I which emits resonance lines at 2402 Å, magnesium (Mg) I which emits resonance lines at 2025 Å, nickel (Ni) I which emits resonance lines at 2026 Å, scandium (Sc) I which emits resonance lines at 2000 Å, Ni I (terminating on the 879 cm-1 electronic metastable state), and numerous other species in the periodic table. Many of these atoms can be readily vaporized at convenient temperatures in a lamp and used in the applications described herein.

In one embodiment, therefore, the plasma includes one or more species that fluoresce (e.g., normally fluoresce strongly) in a region between about 180 nm and about 350 nm to a ground electronic state. In another embodiment, the plasma includes species that fluoresce (e.g., normally fluoresce strongly) in a region between about 180 nm to about 350 nm to electronic metastable states within about 0.5 ev of a ground electronic state. Therefore, such a plasma may be substantially populated by such species at temperatures between room temperature and about 2000° C. In an additional embodiment, an LSP lamp described herein is configured to contain one or more such species. For example, in some such embodiments, the one or more species include Hg that emits resonance lines at 2537 Å, Ba I that emits resonance lines at 2409 Å, Co I that emits resonance lines at 2402 Å, Mg I that emits resonance lines at 2025 Å, Ni I that emits resonance lines at 2026 Å, Sc I that emits resonance lines at 2000 Å, Ni I terminating on a 879 cm-1 electronic metastable state, or some combination thereof.

In one embodiment, the system includes at least one heat source located proximate to the electrodeless lamp and configured to maintain atoms in the plasma in the vapor phase. In this manner, one or more heat sources (e.g., electrical heaters) may be disposed proximate to the LSP lamp (e.g., around the LSP lamp) to keep the atoms in the vapor phase in the LSP lamp. In another embodiment, temperature gradients are optimized via highly focused laser pumping (e.g., by the focusing optics described herein) to optimize the spectral brightness of emission from the types of feed material described herein.

In some embodiments, atoms or molecules that form the one or more species described above are present in the electrodeless lamp prior to generation of the plasma in a quantity or quantities that limit the vapor pressure of the atoms or molecules in the electrodeless lamp such that substantially all of the atoms or molecules are vaporized before the lamp reaches operating temperature. For example, such atoms (or molecules) may be added to the LSP lamp in quantities (from about 1 mg to about 1 g) that limit their vapor pressure in the lamp at relatively high temperatures (e.g., such that substantially all of the material is vaporized before the lamp operating temperature is reached).

In some embodiments, the one or more species described above include atoms formed by decomposition of feed molecules in the electrodeless lamp. For example, feed molecules that decompose to form atoms at relatively high temperatures and that fluoresce in a manner as described above may be added to the LSP lamp.

In one embodiment, the electrodeless lamp includes one or more operating gases that have atomic transitions from electronically excited states to a ground electronic state of one or more corresponding neutral atoms or a state within about 1 eV to about 2 eV of the ground electronic state. In this manner, the LSP lamps described herein may be configured for use with operating gases that have relatively strong atomic transitions from the electronically excited states to the ground electronic state or any state lying within about 1 (or 2) eV of the ground electronic state of the neutral atom.

In one embodiment, the electrodeless lamp includes feed molecules of which about 1% or greater are dissociated at an operating temperature proximate a center of the plasma. In one such embodiment, the feed molecules include iodine ($I_2$), chlorine ($Cl_2$), bromine ($Br_2$), sulfur ($S_2$), nitrogen ($N_2$), oxygen ($O_2$), a diatomic gas, one or more homonuclear diatomic feed materials capable of recombining to form only their corresponding molecular species, one or more rare gases, or some combination thereof. In another embodiment, the electrodeless lamp includes feed molecules of which about 1% or greater are dissociated at an operating temperature of about 600 K to about 25,000 K. In this manner, the lamp may be configured for use with feed molecules that are largely (e.g., about 1% or greater) dissociated at the operating temperature of the center of the plasma (greater than about 600 K and to as high as about 25,000 K). Examples of such feed molecules are $I_2$, $Cl_2$, $Br_2$, $S_2$, $N_2$, $O_2$, and other diatomic species. In an additional embodiment, the feed molecules include homonuclear diatomic feed materials that can only recombine to form their initial molecular species.

In some embodiments, the species described herein are used by themselves, as mixtures with other diatomics, or in the presence of or without rare gases in the mixture.

In one embodiment, the electrodeless lamp includes diatomic hydrogen ($H_2$). In one such embodiment, the light generated by the plasma has a wavelength of about 121 nm. In another such embodiment, the light generated by the plasma has a wavelength of about 121 nm, about 937 nm, about 949 nm, about 972 nm, about 1025 nm, or some combination thereof. In this manner, $H_2$ may be used in the LSP lamp to generate radiation at a wavelength of about 121 nm and/or radiation at a wavelength of about 1025 nm, about 972 nm, about 949 nm, and/or about 937 nm. In another embodiment, Hg atoms are used to generate radiation at a wavelength of about 253.7 nm and/or about 185 nm.

In some embodiments, atomic or molecular species are used in natural isotopic abundance in the lamps described herein. In another embodiment, atomic or molecular species are used in the lamps described herein that are isotopically enriched to arbitrary purity such that greater than about 90% of the radiation is emitted within a spectral bandwidth consistent with imaging using a purely refractive objective. In this manner, the plasmas described herein may be configured to generate narrowband light and/or monochromatic light.

In some embodiments, the LSP lamps described herein are at least partially constructed of glasses or windows that are transparent (e.g., more than about 50% transparent) at the operating wavelength of interest. Operating envelope materials may include fused silica, $CaF_2$, or other amorphous or crystalline materials. In a further embodiment, these lamps are used in a system configured to operate at one or more VUV wavelengths that is purged of substantially all species in the atmosphere that absorb at the operating wavelength of interest. Examples of systems configured for operation in the VUV regime are illustrated in commonly assigned U.S. patent application Ser. No. 10/845,958 by Fielden et al. filed May 14, 2004 published as U.S. Patent Application Publication No. 2005/0252752 on Nov. 17, 2005, and commonly assigned U.S. patent application Ser. No. 10/846,053 by Fielden et al. filed May 14, 2004 published as U.S. Patent Application Publication No. 2005/0254050 on Nov. 17, 2005, all of which are incorporated by reference as if fully set forth herein. The LSP lamps described herein may be used in any of the systems described in these patent applications. In addition, the systems described herein may be further configured as described in these patent applications.

In an additional embodiment, F, Cl, Br, and I lamps are operated at their resonance wavelengths. Note, the resonance wavelength of Cl is about 138 nm, and the resonance wavelength of F is about 125 nm. Therefore, the lamps described herein may be configured to generate light at VUV wavelengths such as 125 nm and 138 nm. In another embodiment, the lamps described herein are used with any filter(s) configured to selectively discriminate against particular fine structure or hyperfine structure emission in natural isotopic abundance or isotopically purified lamps.

In one embodiment, the plasma has a diameter of about 0.5 mm to about 1 mm. The diameter and/or the shape of the plasma can be controlled by focusing optics that focus excitation light to the plasma (possibly in combination with another subsystem such as a gas flow subsystem) as described further herein. For example, in one embodiment, the focusing optics are configured to focus the excitation light to a cylindrical-shaped region within the electrodeless lamp. In one such embodiment, the cylindrical-shaped region has a diameter of about 0.5 mm to about 1 mm and a thickness of about 100 μm to about 200 μm.

Configuring the focus of the excitation light (e.g., from the light driver or drivers) used to sustain the plasma action appropriately is advantageous. Namely, inspection systems most efficiently collect and deliver to the specimen plane certain plasma shapes and sizes. For BF inspection systems used beyond the year 2005, the shrinking pixel sizes and increased imaging computer inspection speeds will demand that plasmas about 0.5 mm to about 1.0 mm in diameter are provided. "Hockey puck" three-dimensional (3D) shaped geometries in which the thickness of the puck is substantially matched to the depth of focus of the inspection system and in which the puck diameter is about 0.5 mm to about 1.0 mm or so are preferred. Therefore, relatively high NA short focal length beam delivery from one or more light drivers is expected to best approach this geometry. In addition, the shape of the plasma can be altered and/or controlled as described further herein (e.g., by the focusing optics possibly in combination with one or more elements of the system such as a gas flow subsystem) to match or substantially match one or more parameters and/or elements of a system such as an inspection system, a defect review system, a metrology system, an imaging system, a lithography system, etc. For example, in one embodiment, the plasma has a geometry shaped to substantially match collection optics of a detection subsystem of a system configured to inspect the specimen. In another embodiment, the plasma has a cylindrical shape substantially matched to image onto the specimen in the system. Such plasma shapes may be created, altered, and/or controlled as described further herein.

In order to deposit substantially all of the radiation from the laser sustaining source into the plasma in a volume defined by a "hockey puck," which has a thickness of about 100 μm to about 200 μm and a diameter of about 1 mm, the relatively high pressure gas in the lamp preferably absorbs substantially all of the pump excitation light within such a volume. In another embodiment, the electrodeless lamp includes a fill gas, and an opacity of the fill gas at a working temperature and pressure of the electrodeless lamp is less than or equal to about 10% reabsorption of light emitted from a center of the lamp within a spectral region from about 200 nm to about 450 nm. In another embodiment, the electrodeless lamp includes a fill gas at a gas pressure such that an opacity of the plasma does not prohibit a majority of the light generated by the plasma from exiting the lamp. For example, the gas type(s) and the gas pressure(s) are preferably selected such that the resulting plasma opacity (see, for example, J. L. Emmett and A. L. Schawlow, and E. H. Weinberg, J. Appl. Phys., 35(9), 2601-2604 (1964) and D. Erskine, B. Roznyal, and M. Ross, J. Quant. Spec. and Radiat. Transfer, 51(12), 97-100 (1994), which are incorporated by reference as if fully set forth herein) does not prohibit the majority of selected radiation (about 200 nm to about 300 nm, or about 200 nm to about 400 nm) from escaping the lamp and reaching the specimen plane through the objective. These two conditions, plasma opacity of emitted radiation and plasma absorption of pump radiation, can be used to determine the pressure of optimum fill for a LSP lamp. For example, pressures between about 5 atm and about 20 atm (at approximately room temperature) will generally fulfill these objectives. Therefore, in one embodiment, a fill pressure of the electrodeless lamp is about 5 atm to about 20 atm at room temperature.

In one embodiment, a wavelength of the excitation light is less than about 10 μm. For example, in order for the light generation process to be efficient, the light used to drive the plasma is preferably optimally coupled to the lamp with as much of the light absorbed in the working region as possible. Relatively intense light fields may preferably be used since the absorption process is primarily multiphoton ionization followed by subsequent plasma absorption. Therefore, relatively good light source focus is desirable. In addition, since multiphoton ionization is a peak power process, (kw/cm$^2$) generally scales as n, where the power of n is generally the number of photons from the light source used to reach the state of ionization sought from the electronic state of the neutral used as a feed. Therefore, as an example, n will equal 10 if one uses about 1 ev photons, the ionization potential of the atom used in the working medium is about 10 ev, and the ground electronic state is the atom of interest. Should an excited state of the atom at, say, about 8 ev, of excitation exist in the working region, two such photons are required. The above processes thus depend upon the power of n=10 and 2, respectively. Therefore, from the above description, it can be seen that relatively short wavelength sources may be desirable, certainly no longer than essentially about 10 μm in wavelength (see, for example, D. L. Franzen, J. Appl. Phys. 44(4), 1727-1732 (1972) and D. L. Franzen, Appl. Phys. Lett., 21 62-64 (1972), which are incorporated by reference as if fully set forth herein) in order to achieve efficient ionization. The above description also illustrates the importance of considerable numbers of metastable, highly excited, near ionization continuum states being present within the plasma in order to effectively couple to the radiation field at moderate fluences.

The design of an optimum LSP light source for applications such as wafer inspection begins with the knowledge that: a) the field of view of broadband catadioptric objectives configured for use with radiation between about 200 nm to about 300 nm or about 200 nm to about 400 nm is on the order of about 1 mm; b) the shape of the LSP is preferably homogenized and configured to best fit a sensor footprint at the wafer plane in which sensor two-dimensional (2D) pixel counts and magnifications are those that will be used for near future semiconductor wafers (e.g., pixel counts on the order of about 2000 by about 2000 and pixel sizes of about 50 nm on a side (yielding substantially the same 1 mm field of view as the objective)); and c) efficient collection of the light is best achieved by either a partial elliptical reflector or a condenser lens that delivers the collected radiation to a homogenizer with a "realistic" NA.

Figure 4:
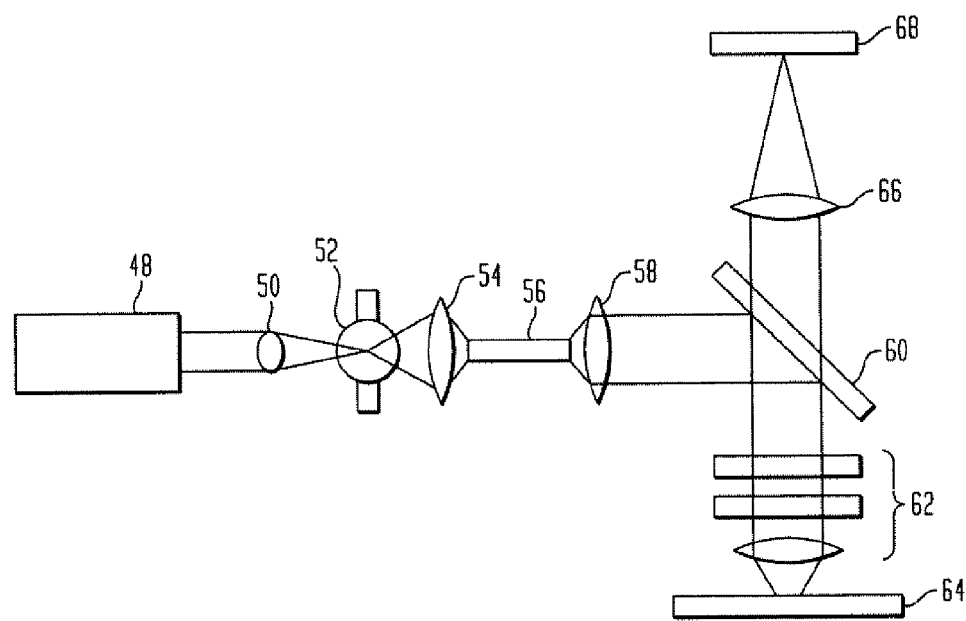
FIG. 4 is a schematic diagram illustrating a side view of an embodiment of a system configured to determine one or more characteristics of a specimen.

FIG. 4 illustrates one embodiment of a system configured to provide illumination of a specimen for a process performed on the specimen. The process may include any of the processes described further herein Such as an inspection process, a defect review process, a metrology process, an imaging process (e.g., imaging by photo emission electron microscopy (PEEM), a lithography process, etc.). In this manner, in some embodiments, the LSP lamp is configured for use in wafer inspection. FIG. 4 also illustrates one embodiment of a system (e.g., an inspection system) configured to determine one or more characteristics of a specimen that includes an LSP lamp configured as described herein.

As shown in FIG. 4, the system includes laser 48 configured to generate excitation light. Laser 48 may include any of the lasers described herein. The laser is configured to direct the excitation light (or "pump" light) to focusing optics 50. Focusing optics 50 may include a set of focusing or beam conditioning optics. Focusing optics 50 may include any suitable such optics. In addition, although focusing optics 50 are shown in FIG. 4 as including one refractive optical element, focusing optics 50 may include one or more refractive optical elements and/or one or more reflective optical elements. Focusing optics 50 may be further configured as described herein. As shown in FIG. 4, focusing optics 50 are configured to focus the excitation light generated by laser 48 to a plasma (not shown in FIG. 4) in electrodeless lamp 52 (e.g., a relatively high pressure LSP light source) such that the plasma generates light. The plasma and the electrodeless lamp may be configured according to any of the embodiments described herein.

The system shown in FIG. 4 is also configured such that the light generated by the plasma illuminates the specimen during the process. For example, the system includes an illumination subsystem configured to illuminate the specimen during the process with the light generated by the plasma. For example, light generated by the plasma that exits electrodeless lamp 52 is collected by optics 54 of the illumination subsystem, which may include "reasonable" NA collection optics 54 (e.g., optics having an NA sufficient to image a substantial portion of the light onto an entrance of homogenizer 56). Optics 54 may include any suitable such optics. In addition, although optics 54 are shown in FIG. 4 as including one refractive optical element, optics 54 may include one or more refractive optical elements and/or one or more refractive optical elements. Optics 54 may be further configured as described herein.

The illumination subsystem may also include homogenizer 56. Light from optics 54 is directed to homogenizer 56 as shown in FIG. 4. Homogenizer 56 may include any suitable homogenizer such as a light pipe. Light exiting homogenizer 56 is directed to collection optics 58 of the illumination subsystem, which are configured to collect light that exits homogenizer 56. Optics 58 may include any suitable such optics. In addition, although optics 58 are shown in FIG. 4 as including one refractive optical element, optics 58 may include one or more refractive optical elements and/or one or more reflective optical elements. Optics 58 may be further configured as described herein.

As shown in FIG. 4, optics 58 are configured to direct light from homogenizer 56 to beam splitter 60 of the illumination subsystem. Beam splitter 60 may include any suitable optical element such as a 50-50 beam splitter. The illumination subsystem may also include objective 62 such as an inspection microscope objective, which as shown in FIG. 4 may include a number of refractive optical elements. The refractive optical elements included in the objective may have any suitable configuration. Objective 62 may also include one or more refractive optical elements and/or one or more reflective optical elements. Objective 62 is configured to focus light from beam splitter 60 to specimen 64, which may include any of the specimens described herein. For example, specimen 64 may include a wafer, a patterned wafer, or a reticle.

The system shown in FIG. 4 also includes a detection subsystem configured to generate output responsive to light from the specimen due to illumination of the specimen. The output can be used to determine the one or more characteristics of the specimen. For example, the detection subsystem may include objective 62, beam splitter 60, imaging or focusing optics 66, and detector or sensor 68. Light from the specimen (e.g., reflected light, scattered light, diffracted light, or some combination thereof) is collected by objective 62 and passes through beam splitter 60. Light from the specimen that passes through beam splitter 60 is focused by imaging or focusing optics 66 onto detector or sensor 68. Optics 66 may include any suitable such optics. In addition, although optics 66 are shown in FIG. 4 as including one refractive optical element, optics 66 may include one or more refractive optical elements and/or one or more reflective optical elements. Optics 66 may be further configured as described herein. Detector 68 may include any of the detectors described herein such as a TDI detector or any other suitable detector or sensor known in the art.

The embodiment of the system shown in FIG. 4 may be further configured as described herein. For example, the system shown in FIG. 4 may include a processor such as that shown in FIG. 1 that is configured to use the output generated by the detection subsystem of the system shown in FIG. 4 (e.g., output generated by detector 68) to determine the one or more characteristics of the specimen. The one or more characteristics may include any of the characteristics of the specimen described herein.

In one embodiment, laser 48 is a cw laser. In addition, laser 48 is preferably a cw laser since it is preferable that electrons be present at all times within the electrodeless lamp to maintain a relatively high density of excited atomic electronic states within the plasma for a relatively low pump threshold and for relatively good coupling of the excitation (or pump) light to the plasma. In another embodiment, the laser includes a diode laser, a diode laser stack, a fiber laser, a fiber coupled diode laser, a carbon dioxide ($CO_2$) laser, an acoustically modulated diode (i.e., an AM modulated diode), or a diode pumped fiber laser. For example, laser 48 may preferably be one of the following types of light sources: a) fiber coupled laser diodes with fiber apertures from about 100 µm to about 200 µm, b) a $CO_2$ laser; or c) a diode pumped fiber laser.

In one embodiment, focusing optics 50 include a lens configured to focus the excitation light to a spot size and radiance sufficient to sustain the plasma. In one such embodiment, the lens has an NA of at least about 0.3. For example, focusing optics 50 preferably includes a relatively large NA lens in order to bring the radiation from pump source a), b), or c) described above or any other lasers described herein to a spot size and radiance sufficient to sustain the plasma. In some embodiments, the focusing optics are configured to focus the excitation light to the lamp to initiate the plasma. In another embodiment, the system includes a pulsed light source, an RF coil, a voltage source external to the lamp, or some combination thereof to initiate the plasma. For example, the plasma may be initiated by the laser or, if one chooses, by either an RF coil or an initial gas breakdown of the electrons by an externally applied voltage and current as in a conventional lamp. The pulsed light source, the RF coil, and the voltage source may include any suitable such components known in the art.

In one embodiment, a power of the laser is greater than about 100 W. In another embodiment, an optical average cw power of the excitation light is about 100 W to about 1000 W.

For example, in order to achieve the desired average power and brightness, the laser, whether the laser is a), b), or c) described above or any other laser described herein is preferably from about 100 W to about 1000 W of optical average cw power. In another embodiment, the system includes an additional laser configured to generate additional excitation light. In one such embodiment, the focusing optics are configured to focus the additional excitation light to the plasma, and a sum of the power of the laser and the additional laser is in a range of about 100 W cw to about 1000 W cw. For example, the excitation light may be delivered from either one or more light sources, and the sum of the power of the light sources may fall in the range from about 100 W cw to about 1000 W cw.

In an additional embodiment, the system includes at least one additional laser configured to generate additional excitation light. In one such embodiment, the focusing optics are configured to focus the excitation light and the additional excitation light to the plasma simultaneously such that the excitation light and the additional excitation light overlap within a cylindrical-shaped region within the electrodeless lamp. In one such embodiment, the cylindrical-shaped region has a diameter of about 0.5 mm to about 1 mm and a thickness of about 100 µm to about 200 µm. In this manner, if multiple sources are used, the beams are preferably overlapped within their focus such that the LSP is obtained primarily within a "hockey puck" 3D space of about 1 mm diameter and about 200 µm thickness within the electrodeless lamp, Such 3D hockey puck space can be achieved within the electrodeless lamp by arranging focusing optics 50 such that the laser beams only reach a diameter of about 200 µm or less when they are within about 1 mm of each other or less (e.g., overlapping).

In one embodiment, a gas pressure within the electrodeless lamp is about 1 atm to about 50 atm. For example, the pressure of the gas within the lamp is preferably greater than about 1 atm and no more than about 50 atm such that the gas has an emissivity of as near to unity as possible and such that the radiation within the LSP lamp is not reabsorbed by relatively hot gas outside of the "hockey puck" laser excited region.

In one embodiment, the illumination subsystem of the system shown in FIG. 4 includes a condenser lens configured to collect the light generated by the plasma. In another embodiment, the illumination subsystem of the system shown in FIG. 4 includes an elliptical reflector configured to collect the light generated by the plasma, and the plasma is located at one focal point of the elliptical reflector. For example, collection optics 54 are preferably configured to collect as much light generated by the plasma as possible and may include, for example, a condenser lens or an ellipse (e.g., an elliptical reflective collector) with tile plasma located at one focus of the ellipse. The diameter of the homogenizer and the NA of collection optics 58 will define the footprint of the LSP at the specimen plane since objective 62 will normally have a substantially high NA (e.g., an NA on the order of about 0.7 to about 0.95). The ratio of the NA of the collection optics and the NA of the objective, therefore, determines the ratio of the ellipse physical dimension to the footprint of the plasma light source at the specimen plane, the ratio being $NA_{collector}/NA_{objective}$.

In one embodiment, the light generated by the plasma includes DUV light. In another embodiment, the light generated by the plasma includes broadband light. In an additional embodiment, the light generated by the plasma has a single line spectra. In some embodiments, the light generated by the plasma includes light in a spectral region from about 180 nm to about 450 nm. In additional embodiments, the light generated by the plasma includes light in a spectral region from about 200 nm to about 450 nm. As described above, the light that is generated by the plasma can be controlled and/or selected by selecting the feed material(s) used to generate the plasma.

The embodiments described herein may, therefore, be used in a number of applications. For example, besides wafer inspection and defect review, a relatively bright broadband lamp configured as described herein can be used in the following applications. In particular, the lamps described herein may be used for reticle inspection and defect review using broadband light or single line spectra from particular atomic species such as any of the atomic species described herein. In addition, the lamps may be used for broadband optical metrology such as spectral CD measurement systems that use broadband reflectivity to determine array shapes and sizes (e.g., shapes and sizes of an array of patterned features).

In another example, the lamps described herein may be used for electron imaging in which electrons are generated by DUV light exposure of a semiconductor surface creating pho-electrons known as PEEM. In addition, by providing relatively intense broadband light down to substantially short wavelengths, an LSPLS described herein may be used to image a selectable set of work functions. For example, one embodiment of a system configured to generate an image of a specimen includes a laser configured to generate excitation light. The system also includes focusing optics configured to focus the excitation light to a plasma in an electrodeless lamp such that the plasma generates light. In addition, the system includes an illumination subsystem configured to illuminate the specimen with the light generated by the plasma. The system further includes a detection subsystem configured to generate output responsive to electrons emitted by the specimen due to illumination of the specimen with the light generated by the plasma. The output includes the image of the specimen.

Such a system may be configured as shown in FIG. 4. For example, the laser included in such a system may include laser 48 shown in FIG. 4. Laser 48 may be configured to generate excitation light as described herein. In this embodiment of the system, the laser may include any of the lasers described herein. In addition, the focusing optics included in such a system may include focusing optics 50 shown in FIG. 4. The focusing optics included in such a system may be configured to focus the excitation light to a plasma in an electrodeless lamp (e.g., electrodeless lamp 52) such that the plasma generates light as described further herein. The plasma and the electrodeless lamp included in such a system may be configured as described further herein. In addition, in a system configured for PEEM, the light generated by the plasma may include DUV light. The plasma may generate DUV light as described further herein. In one embodiment, the specimen imaged by such a system may include a surface formed of a semiconductive material. The semiconductive material may include any semiconductive material that will emit electrons in response to illumination with DUV light. In this manner, the system may be used for electron imaging in which electrons are generated by DUV light exposure of a semiconductor surface creating PEEM that are then detected.

In another embodiment, the light generated by the plasma includes broadband light such that the system can image a selectable set of work functions of the specimen. A plasma configured to generate broadband light may be configured as described further herein. Therefore, the plasma may be configured to provide relatively intense broadband light down to substantially short wavelengths such that the system can be used to image a selectable set of work functions.

Furthermore, the illumination subsystem included in such a system may be configured as shown in FIG. 4. For example, the illumination subsystem may include optics 54, homogenizer 56, collection optics 58, beam splitter 60, and objective 62 configured to illuminate specimen 64 with the light generated by the plasma. The detection subsystem of the imaging system may also be configured as shown in FIG. 4. For example, the detection subsystem may include objective 62, beam splitter 60, imaging or focusing optics 66, and detector 68, and the detection subsystem may be configured to generate output responsive to electrons emitted by specimen 64 due to illumination of specimen 64 with the light generated by the plasma. However, unlike the systems described above, in systems configured to generate an image of the specimen using electrons emitted by the specimen, the elements of the detection subsystem may be configured to collect, focus, and detect electrons emitted by the specimen instead of light from the specimen and may include any such elements known in the art.

In yet another example, the lamps described herein may be used in lithography systems configured to employ i-line radiation that are still in use and sold in the semiconductor industry. While existing electrical discharge light sources are larger in size (many mm's) and require higher electrical power (about 5 kW), the makers of these lithography systems (or "litho steppers") desire higher brightness and longer lifetimes. Even if an LSPLS described herein uses about 1 kW to about 3 kW of IR pump power (i.e., IR laser power), the LSPLS would still have value if the lamp lasted longer and produced more i-line light within the required volume thereby allowing higher stepper throughputs.

For example, another embodiment relates to a system configured to perform a lithography process. This system includes a laser configured to generate excitation light. The system also includes focusing optics configured to focus the excitation light to a plasma in an electrodeless lamp such that the plasma generates light. In addition, the system includes an illumination subsystem configured to image the light generated by the plasma onto the specimen in a predetermined pattern such that the predetermined pattern can be transferred to the specimen.

Such a system can be configured as shown in FIG. 4. For example, a system configured to perform a lithography process may include laser 48 configured to generate excitation light. The laser may include any of the lasers described herein, and the excitation light may include any of the excitation light described herein. Such a system may also include focusing optics 50 configured to focus the excitation light to a plasma in electrodeless lamp 52 such that the plasma generates light. In one such embodiment, the light generated by the plasma includes i-line light. The plasma and the electrodeless lamp may be further configured as described herein. A system configured to perform the lithography process may also include an illumination subsystem, which may include optics 54, homogenizer 56, collection optics 58, beam splitter 60, and objective 62 configured to illuminate specimen 64 with the light generated by the plasma. In a different embodiment, the illumination subsystem may include optics 54 configured to collect the light generated by the plasma and objective 62 configured to image the light onto specimen 64. In this manner, the lithography system may or may not include homogenizer 56, collection optics 58, and beam splitter 60. Specimen 64 may, in this embodiment, include a wafer or another substrate having a layer of resist formed thereon. The resist may be any resist that is suitable for i-line lithography.

In addition, during a lithography process, a reticle (not shown) may be positioned in the path of the light between optics 54 and objective 62 such that the light passes through the reticle in a predetermined pattern such that the predetermined pattern can be imaged onto the specimen. In this manner, a predetermined pattern can be transferred from the reticle to the specimen. The predetermined pattern transferred to the specimen may be approximately the same as the predetermined pattern formed on the reticle (e.g., allowing for effects of the reticle on the light and effects of the resist on the image projected onto the specimen) or approximately the inverse of the predetermined pattern formed on the reticle (e.g., allowing again for effects of the reticle on the light and effects of the resist on the image projected onto the specimen). In other words, the lithography system described herein may be used to transfer a predetermined pattern to a positive resist and/or a negative resist.

In one embodiment, the electrodeless lamp is at a pressure of above about 1 atm at a working temperature of the electrodeless lamp, and the light generated by the plasma includes light in a spectral region from about 200 nm to about 400 nm. In this manner, the LSP lamps described herein may be used at pressures above about 1 atm (at their working temperature) for the production of light for applications such as wafer inspection in the spectral region between about 200 nm to about 400 nm (see, for example, G. Babucke, G. Hartel, and H-G Kloss, J. Phys. D, App. Phys, 24, 1316-1321, (1991), which is incorporated by reference as if fully set forth herein) with brightness from about 10 W/mm$^2$-sr to about 50 W/mm$^2$-sr. In another embodiment, the light generated by the plasma has a brightness of about 2 W/mm$^2$-sr to about 50 W/mm$^2$-sr in an integral region of the electromagnetic spectrum from about 200 nm to about 400 nm. In this manner, the electrodeless lamps described herein can be used as sources with spectral brightness in the range from about 2 W/mm$^2$-sr to about 50 W/mm$^2$-sr in the integral region of the electromagnetic spectrum from about 200 nm to about 400 nm. In a further embodiment, the light generated by the plasma has an average power of at least about 3 W within any band in a spectral region from about 200 nm to about 450 nm. In this manner, the LSP lamps described herein may be configured to generate in excess of about 3 W of average power within any band contained within the wavelength region between about 200 nm and about 450 nm.

In one embodiment, the plasma does not produce an average plasma opacity over a plasma axis length of greater than about 1 e-folding from one end of the electrodeless lamp to another end of the electrodeless lamp. For example, in some embodiments, one or more relatively high brightness cw lasers or light drivers are configured for excitation of these plasmas in roughly cylindrical geometries in which the plasma axis length does not produce an average plasma opacity over this region of greater than about one e-folding from "end-cap" to "end-cap." In another embodiment, a wavelength of the excitation light is about 0.7 µm to about 1.5 µm. For example, one or more diode light drivers, one or more diode light driver stacks, one or more fiber light drivers, one or more fiber coupled diode light drivers, one or more other sources of low cost light driven technology, or some combination thereof at wavelengths between about 0.7 µm and about 1.5 µm may be configured to excite the light driven electrodeless produced plasma. In an additional embodiment, one or more $CO_2$ lasers are configured to excite the light driven electrodeless produced plasma.

In one embodiment, the electrodeless lamp includes a background rare gas and a gas containing a halide. In one such embodiment, a pressure of the background rare gas is at least about 1 atm, and a pressure of the gas containing the halide is less than or equal to about 1 atm. For example, in some embodiments, the light driven produced plasma of the LSP lamps described herein is configured to produce excimer radiation by using about 1 atm or more of background rare gas along with a similar or lower fill pressure of halide containing gas. In another embodiment, a fill pressure of gases in the electrodeless lamp is about 4 atm or higher. In this manner, the LSP lamps described herein may be configured to use fill pressures of gases to as much as about 4 atm (or bar) to about 10 atm (or bar) or higher (see, for example G. Babucke, G. Hartel, and H-G Kloss, J. Phys. D, App. Phys, 24, 1316-1321, (1991), which is incorporated by reference as if fully set forth herein). In a further embodiment, the electrodeless lamp includes a fill gas, and an opacity of the fill gas at a working temperature and pressure of the electrodeless lamp is less than or equal to about 10% reabsorption of light emitted from a center of the lamp within a spectral region from about 200 nm to about 450 nm. For example, the LSP lamps described herein may be configured to use one or more fill gases selected such that the opacity of the one or more fill gases at the working temperature and pressure of the lamps does not exceed about 10% reabsorption of about 200 nm to about 450 nm radiation emitted from the center of the lamp (see, for example, D. Erskine, B. Roznyal, and M. Ross, J. Quant. Spec. and Radiat. Transfer, 51(12), 97-100 (1994), which is incorporated by reference as if fully set forth herein).

In one embodiment, the focusing optics include a lens configured to focus the excitation light to the plasma such that the plasma has a predetermined shape. In one such embodiment, the lens has an NA of at least about 0.3. In some embodiments, an excitation volume of the electrodeless lamp is substantially matched to a field of view of collection optics of a detection subsystem of a system configured to inspect the specimen. In this manner, the plasma excitation in the LSP lamps described herein may be shaped by one or more beams delivered through a substantially fast lens (e.g., a lens having an NA greater than about 0.3) to substantially match the excitation volume to the collection optics field of view appropriate for applications such as wafer and reticle inspection. In a farther embodiment, excitation radiation for the LSP lamps described herein is provided by one or more light drivers to form approximately disc or hockey puck shaped plasmas that are substantially matched to image onto the specimen plane in inspection systems. In some such embodiments, the plasma has a diameter of between about 100 µm and about 2 mm. In addition, the plasma size may affect and/or control the size of the light beam generated by the plasma. For example, in one embodiment, the light generated by the plasma has a diameter of about 100 µm to about 2 mm. In an additional embodiment, light drivers of any wavelength are used to ignite the plasma in the LSP lamps described herein with a light driven power in excess of about 100 W. In another embodiment, light driver radiation in which the light source medium is a diode pumped fiber of moderate M-squared is used for the LSP lamps described herein. In yet another embodiment, light drivers of the LSP lamps described herein are configured for use at wavelengths of about 1 µm or wavelengths between about 700 nm and about 1.3 µm.

In one embodiment, the plasma is generated using a rare earth gas and a mercury gas. In one such embodiment, the light generated by the plasma includes light in a spectral region from about 230 nm to about 480 nm. For example, the LSP lamps described herein include electrodeless or light driven produced plasmas that contain a combination of rare earth (Xe, Ar, . . . ) and Hg gases selected to optimize spectral brightness in the wavelength region of about 230 nm to about 480 nm. In another embodiment, the LSP lamps described herein are substantially flat on one side of the LSP lamps such that the LSP lamps have a shape that is generally hemispherical to reduce, and even limit, the distance between the entrance of the light driver to the working medium and its focal point. In a further embodiment, such a configuration of the LSP lamps and other related bulb design concepts are employed to optimize the shape of the plasma to the collector for the inspection system.

In one embodiment, a temperature of the plasma is about 10,000 K to about 30,000 K. For example, plasma temperatures of the LSP lamps described herein may be between about 10,000 K to about 30,000 K for any of the fill gases described herein.

In another embodiment, specially designed "ignitor" electrodes are used in conjunction with the overall light driven produced plasma bulb. In one such embodiment, the specially designed ignitor electrodes are used with excitation light driver(s) that do not have high enough intensity to initiate the plasma action. In some embodiments, the laser includes a frequency doubled laser, and a wavelength of the excitation light is about 0.4 µm to about 0.7 µm. For example, frequency doubled light drivers in the mid- and near-IR region of the visible spectrum (about 0.4 µm to about 0.7 µm) may be used for excitation of the plasma in the LSP lamps described herein.

In one embodiment, the electrodeless lamp includes an internal lens or a curved reflector. For example, the LSP lamps described herein may include an internal lens or curved reflector to achieve substantially high NA focus. In an additional embodiment, the LSP lamps described herein include an electrodeless or light driven produced plasma in which radiation collected from the plasma between about 200 nm to about 450 nm is more than about 3 W. In a further embodiment, relatively high peak power light sources such as amplitude modulation (AM) modulated diodes (or AM modulated diodes) or fiber light sources are used with the LSP lamps described herein to increase the coupling efficiency of the driver to the plasma or lamp working region.

Further description provided herein generally relates to IR pump light shaping that may be used for generating an optimal plasma shape for the best coupling with an illumination subsystem. In particular, to optimize the collection of the generated light, the pump light source is preferably shaped to an optimal form. This shape is not necessarily the smallest possible light source size and depends on the illumination subsystem.

In one embodiment, an NA of the focusing optics is selected such that a size of the plasma is reduced along a direction to which the excitation light is focused to the plasma by the focusing optics. For example, a system that includes an LSP lamp and that may be configured according to any of the embodiments described herein may be configured to provide relatively high NA illumination (e.g., using either a relatively high NA lens or a relatively high NA partial elliptical reflector) of a specimen for inspection or another application described herein. Relatively high NA illumination of the plasma may be used, not for the reduction of the pumping light beam size, but for achieving the shortest depth of focus to reduce plasma size along the pumping beam.

In one embodiment, the laser includes a distributed light source. For example, a distributed light source may be used to excite the plasma in an LSP lamp. One example of a distributed light source is a laser diodes bar. The distributed light source allows the use of a relatively large focus spot together with relatively short focal length. Effectively, the distributed light source can be used to form an image of the desired pupil pattern for illumination of the specimen. For example, illumination for edge contrast (EC) mode inspection may be provided using a ring ("bagel") plasma shape if the plasma is located in a pupil or image conjugate plane. For a relatively high power pumping laser, this shape can be difficult to achieve unless a distributed light source is used as the excitation light source.

In one embodiment, the focusing optics include at least one optical element configured to focus the excitation light to the plasma and configured to collect the light generated by the plasma. For example, one configuration of the system that can be used to provide such shaping includes common optics for light pumping and DUV/UV/Vis generated light collection, and such common optics may include a focusing partial elliptical reflector or parabolic reflector to achieve relatively high NA. Such configurations are described further below.

Figure 5:
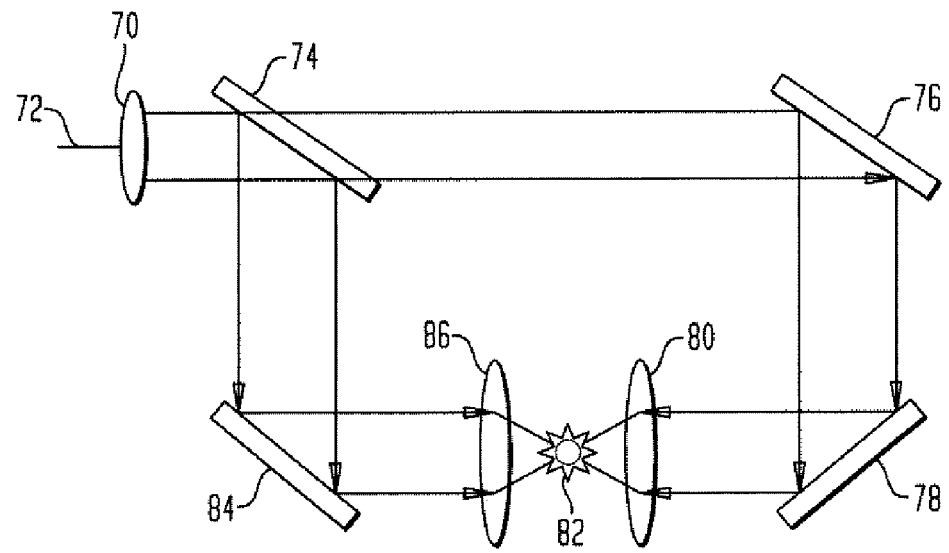
FIG. 5 is a schematic diagram illustrating a side view of an embodiment of focusing optics configured to shape a plasma by focusing excitation light to the plasma in two substantially opposite directions.

In one embodiment, the focusing optics are configured to focus the excitation light to the plasma in two substantially opposite directions. For example, FIG. 5 illustrates one embodiment of focusing optics configured for shaping the plasma by pumping in the forward and backward directions. As shown in FIG. 5, the focusing optics include beam expander 70 configured to expand beam 72 of light from a light source such as a laser (not shown in FIG. 5). Beam expander 70 may include any suitable optical element known in the art. The light source may include any of the light sources described herein configured to generate any of the excitation light described herein. As shown in FIG. 5, light from beam expander 70 is directed to beam splitter 74, which may include any suitable beam splitter known in the art. For example, beam splitter 74 may include a 50-50 beam splitter.

As shown in FIG. 5, beam splitter 74 is configured such that one portion of the light passes through beam splitter 74 and is directed to reflective optical element 76, which may include a flat mirror or another suitable reflective optical element. Light reflected by reflective optical element 76 is directed to reflective optical element 78, which may also include a flat mirror or another suitable reflective optical element. Light reflected by reflective optical element 78 is directed to refractive optical element 80, which may be configured as a focusing lens, and which may include any of the refractive optical elements described herein. Refractive optical element 80 is configured to focus the light from reflective optical element 78 to plasma 82. The plasma may be further configured as described herein.

As further shown in FIG. 5, beam splitter 74 is configured such that another portion of the light from beam expander 70 is reflected from beam splitter 74 and is directed to reflective optical element 84, which may include a flat mirror or another suitable reflective optical element. Light reflected by reflective optical element 84 is directed to refractive optical element 86, which may be configured as a focusing lens, and which may include any of the refractive optical elements described herein. Refractive optical element 86 is configured to focus light from reflective optical element 84 to plasma 82.

As shown in FIG. 5, light from refractive optical elements 80 and 86 is directed to plasma 82 simultaneously at substantially opposite directions. In this manner, light from refractive optical elements 80 and 86 can pump the plasma in both the forward and backward directions. In addition, light from refractive optical elements 80 and 86 can shape the plasma by pumping the plasma in the forward and backward directions. Furthermore, in some embodiments, refractive optical elements 80 and 86 may be relatively high NA lenses (e.g., such that the relatively high NA excitation light has a relatively short depth of focus along the direction of the pumping beams thereby reducing plasma size along the directions of the pumping beams). The focusing optics shown in FIG. 5 may be further configured as described herein. In addition, the focusing optics shown in FIG. 5 may be included in any of the system embodiments described herein.

Figure 6:
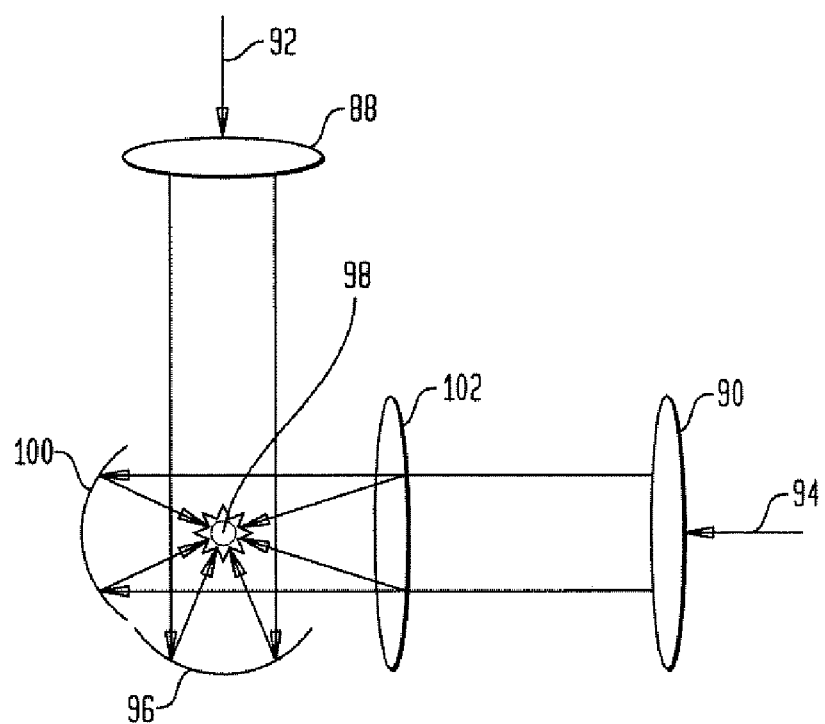
FIG. 6 is a schematic diagram illustrating a side view of an embodiment of focusing optics that include refractive and reflective optical elements configured to focus excitation light to a plasma.

In another embodiment, the focusing optics include at least one reflective optical element and at least one refractive optical element. In one such embodiment, the at least one reflective optical element and the at least one refractive optical element are configured to focus the excitation light to the plasma simultaneously. For example, FIG. 6 illustrates one embodiment of focusing optics configured for using combined refractive and reflective optics to "double focus" excitation light such as an IR pump beam. As shown in FIG. 6, the focusing optics includes beam expanders 88 and 90 configured to expand the cross-sectional areas of beams 92 and 94, respectively. The beam expanders may include any suitable beam expanders known in the art. Beams 92 and 94 may be generated by any of the excitation light sources described herein. In addition, beams 92 and 94 may be generated by the same excitation light source or different excitation light sources (e.g., the same or different lasers).

Light from beam expander 88 is directed to spherical reflector 96. Spherical reflector 96 may include any suitable reflective optical element known in the art and may be further configured as described herein. As shown in FIG. 6, spherical reflector 96 is configured to focus light from beam expander 88 to plasma 98. Plasma 98 may be configured according to any of the embodiments described herein. In a similar manner, light from beam expander 90 is directed to spherical reflector 100. Spherical reflector 100 may include any suitable reflective optical element known in the art and may be further configured as described herein. As shown in FIG. 6, spherical reflector 100 is configured to focus light from beam expander 90 to plasma 98.

In some embodiments, the focusing optics are configured to focus the excitation light to the plasma in two substantially perpendicular directions simultaneously. For example, as shown in FIG. 6, spherical reflectors 96 and 100 are configured to focus light to plasma 98 simultaneously at substantially perpendicular directions. The focusing optics shown in FIG. 6 may also include refractive optical element 102 configured to focus light to plasma 98. Refractive optical element 102 may include any of the refractive optical elements described herein. As shown in FIG. 6, refractive optical element 102 and spherical reflector 96 may be configured to focus light to plasma 98 simultaneously at substantially perpendicular directions. In addition, as shown in FIG. 6, refractive optical element 102 and spherical reflector 100 may be configured to focus light to plasma 98 simultaneously at substantially opposite directions.

In one embodiment, the focusing optics are configured to focus the excitation light to the plasma at different directions simultaneously to substantially the same focal spot. In another embodiment, the focusing optics are configured to focus the excitation light to the plasma at different directions simultaneously to offset focal spots. For example, two or more of the pump assemblies shown in FIG. 6 can be combined at substantially the same focal spot or slightly offset focal points to achieve desired plasma shaping. The focusing optics shown in FIG. 6 may be further configured as described herein. In addition, the focusing optics shown in FIG. 6 may be included in any of the system embodiments described herein.

Figure 7:
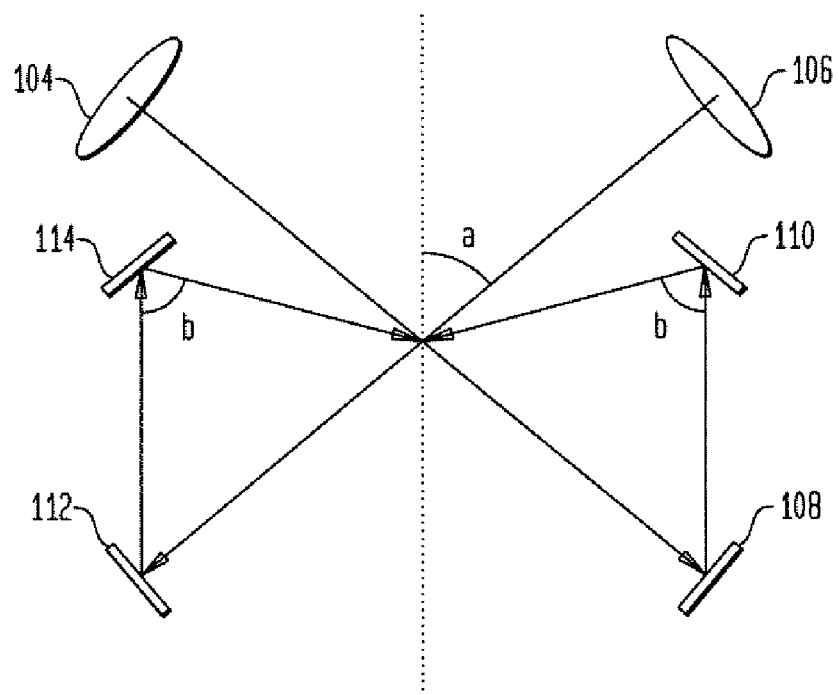
FIG. 7 is a schematic diagram illustrating a cross-sectional view of an embodiment of focusing optics configured to focus excitation light transmitted by a plasma back into the plasma.

In one embodiment, the focusing optics are configured to collect the excitation light that is not absorbed by the plasma and to focus the collected excitation light to the plasma. For example, FIG. 7 illustrates one embodiment of focusing optics for "re-pumping" 3 or more passes of the pump light into the plasma. The focusing optics shown in FIG. 7 include refractive optical elements 104 and 106. Refractive optical elements 104 and 106 are configured to focus excitation light from one or more excitation light sources (not shown in FIG. 7), which may include any of the excitation light sources described herein, to a plasma (not shown in FIG. 7), which may be configured as described herein. Refractive optical elements 104 and 106 may be further configured as described herein (e.g., refractive optical elements 104 and 106 may include relatively high NA lenses). At least some of the excitation light focused to the plasma by refractive optical elements 104 and 106 is preferably absorbed by the plasma, and some of the excitation light focused to the plasma by refractive optical elements 104 and 106 may not be absorbed by the plasma and will, therefore, transmit through the plasma.

The focusing optics may also include reflective optical elements 108, 110, 112, and 114. Excitation light focused to the plasma by refractive optical element 104 that transmits through the plasma may be collected by reflective optical element 108, which may be a flat mirror or any other suitable reflective optical element. Excitation light collected by reflective optical element 108 is directed to reflective optical element 110, which is configured to direct the excitation light from reflective optical element 108 back to the plasma. Reflective optical element 110 may also include a flat mirror or any other suitable reflective optical element. In this manner, excitation light that was initially not absorbed by the plasma may be "re-pumped" back into the plasma, which may increase the efficiency of the LSP light source.

In a similar manner, excitation light focused to the plasma by refractive optical element 106 that transmits through the plasma may be collected by reflective optical element 112, which may be a flat mirror or any other suitable reflective optical element. Excitation light collected by reflective optical element 112 is directed to reflective optical element 114, which is configured to direct the excitation light from reflective optical element 112 back to the plasma. Reflective optical element 114 may also include a flat mirror or any other suitable reflective optical element. In this manner, excitation light that was initially not absorbed by the plasma may be "re-pumped" back into the plasma, which may increase the efficiency of the LSP light source. The angle, a, at which the refractive optical elements shown in FIG. 7 focus excitation light to the plasma may or may not be the same as angle, b, at which the excitation light is re-pumped back into the plasma by the reflective optical elements shown in FIG. 7. The focusing optics shown in FIG. 7 may be further configured as described herein. In addition, the focusing optics shown in FIG. 7 may be included in any of the system embodiments described herein.

Figure 8:
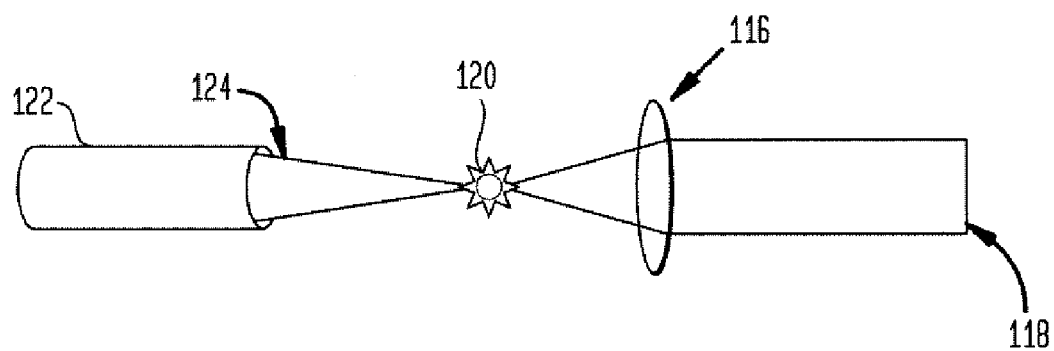
FIGS. 8-11 are schematic diagrams illustrating a cross-sectional view of various embodiments of a gas flow subsystem configured to direct a gas to a plasma.
Figure 9:
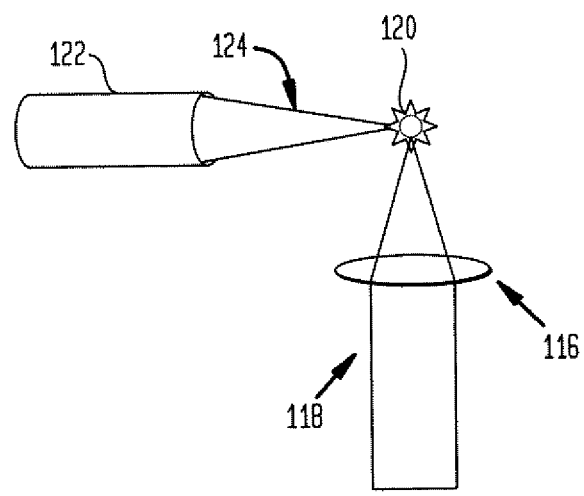

In one embodiment, the system includes a gas flow subsystem configured to direct a gas to the plasma. For example, a system configured to provide illumination as described herein may include a gas flow subsystem (or "jet system") for sustained arc shaping. FIGS. 8-9 illustrate various embodiments of a gas flow subsystem that is configured for sustained arc shaping. As shown in FIG. 8, one embodiment of a system that includes a gas flow subsystem may also include focusing optics which include refractive optical element 116 configured to focus excitation beam 118 from an excitation source (not shown in FIG. 8) to plasma 120. Refractive optical element 116 may be configured as described further herein (e.g., refractive optical element 116 may include a relatively high NA refractive optical element). In addition, refractive optical element 116 may be replaced with one or more refractive optical elements and or one or more reflective optical elements. The excitation source may include any of the excitation sources described herein. Excitation beam 118 may include, for example, an electron beam, an X-ray beam, a particle beam, or a laser beam. Plasma 120 may be further configured as described herein.

As further shown in FIG. 8, the gas flow subsystem includes nozzle 122 that may be coupled to one or more gas sources (not shown in FIG. 8). Nozzle 122 may be coupled to any suitable gas source(s). Nozzle 122 may have any suitable configuration such that gas jet 124 can be directed to plasma 120. In addition, nozzle 122 may be further configured as described herein. In one embodiment, the gas flow subsystem is configured to direct the gas to the plasma such that the gas directed to the plasma affects a shape of the plasma. For example, the gas jet may be directed to plasma 120 such that the gas jet assists in shaping the plasma and therefore can be used for sustained arc shaping.

In one embodiment, the gas flow subsystem is configured to direct a gas to the plasma at a direction substantially opposite to a direction at which the focusing optics focus the excitation light to the plasma. For example, as shown in FIG. 8, gas jet 124 may be directed to the plasma along a direction that is substantially opposite to the direction along which the excitation beam is directed to the plasma by refractive optical element 116. However, the gas jet may be directed to the plasma along a direction arranged at a different angle with respect to the direction along which the excitation beam is directed to the plasma. For example, in one embodiment, the gas flow subsystem is configured to direct a gas to the plasma at a direction substantially perpendicular to a direction at which the focusing optics focus the excitation light to the plasma. In one such example, as shown in FIG. 9, gas jet 124 is directed to plasma 120 along a direction that is substantially perpendicular to the direction along which excitation beam 118 is directed to the plasma by refractive optical element 116. The embodiment shown in FIG. 9 may be further configured as described above with respect to FIG. 8. In addition, the embodiments shown in FIGS. 8 and 9 may be further configured as described herein. Furthermore, the embodiments shown in FIGS. 8 and 9 may be included in any of the systems described further herein.

In one embodiment, the gas flow subsystem is configured to direct a gas to the plasma such that the gas directed to the plasma increases isolation of the plasma. For example, some embodiments of the system may be configured to use target shaping (localization in space) by the gas flow subsystem instead of or in addition to the excitation light shaping or pumping beam shaping to obtain a predetermined light source shape and for the light source isolation. Since the considered target (i.e., the plasma) in most cases is either a gas or liquid medium, using a gas jet is a natural shaping technique for such media.

Two main configurations can be used to overcome the pumping beam resolution limitation and avoid pumping beam and/or generated light scattering and/or absorption by the cold gas (i.e., the gas jet). One embodiment includes light pumping substantially opposite to the gas jet stream (e.g., as shown in FIG. 8). In this case, the plasma size may be limited by the gas jet size in two directions and by diffusion in the third direction. (The pumping beam spot size in this case can be reduced down to a few microns.) Another embodiment includes passing a gas jet through an RF standing wave knot (a gas jet directed substantially perpendicular to the wave front). The RF wave front is preferably relatively wide, and the gas jet may limit the plasma size. An additional embodiment includes an excitation beam such as an ion or electron beam directed substantially perpendicular to the gas jet stream (e.g., as shown in FIG. 9). Such an embodiment may be used to deliver the pumping beam relatively un-scattered to the desired location in the plasma. In another embodiment, the gas flow subsystem is configured to direct a gas to the plasma such that the gas increases propagation of the generated light through the plasma. For example, a further embodiment uses Hg in an electrodeless lamp for the light generation. Cold Hg vapor in the electrodeless lamp effectively absorbs substantially all of the light at a wavelength of about 250 nm. The use of a gas jet reduces, and may even avoid, propagation of the generated light through the cold Hg vapor. Similar effects can be observed for various targets.

Figure 10:
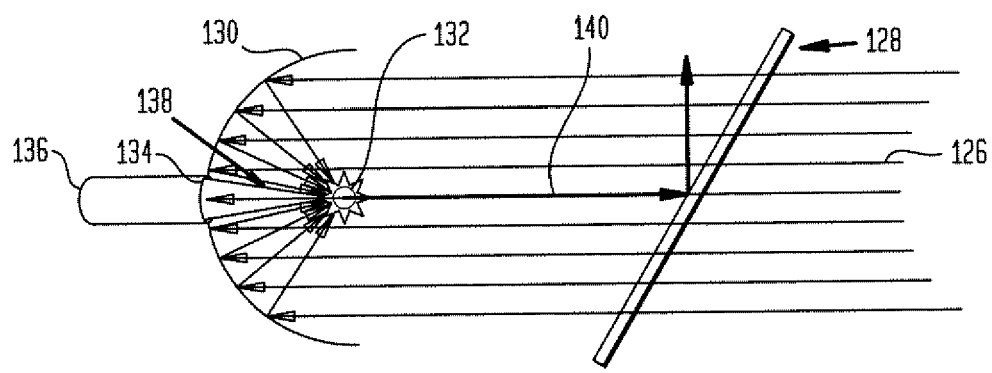
Figure 11:
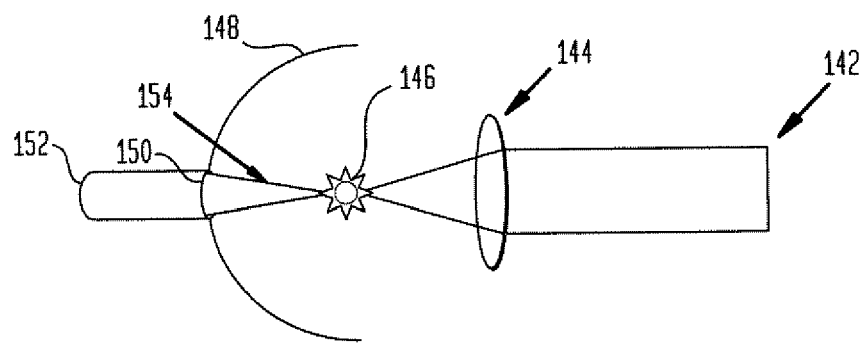

FIGS. 10-11 illustrate various embodiments of a nozzle design that may be used in gas flow subsystems configured to direct a gas to a plasma in an electrodeless lamp that generates DUV light. As shown in FIG. 10, excitation light 126 from an excitation source (not shown in FIG. 10) may be directed through cold mirror 128 (e.g., a dichroic mirror configured to reflect substantially the entire visible and ultraviolet light spectrum and to transmit infrared wavelengths). The excitation light may include any of the excitation light described herein such as a laser beam, which may be expanded as described herein. In addition, the excitation source may include any of the excitation sources described herein. Excitation light 126 that passes through cold mirror 128 is directed toward focusing optics that include reflective optical element 130, which is configured to focus the excitation light that passed through the cold mirror to plasma 132. Reflective optical element 130 may include a spherical mirror, an elliptical mirror, or any other suitable reflective optical element, all of which may be further configured as described herein. Plasma 132 may be further configured as described herein.

In one embodiment, the gas flow subsystem is configured to direct a gas to the plasma through an aperture in an optical element of the focusing optics. For example, as shown in FIG. 10, reflective optical element 130 may include aperture 134 configured such that nozzle 136 and/or gas jet 138 can pass through the aperture. In this manner, nozzle 136 may be configured to direct gas jet 138 through reflective optical element 130 to plasma 132. Nozzle 136 may be further configured as described herein. The gas jet may also be further configured as described herein. Light 140 generated by plasma 132 such as DUV light and/or any other light described herein may be directed by cold mirror 128 to other optical components (not shown in FIG. 10), which may include any of the optical components of any of the illumination subsystems described herein, such that the light can be directed to a specimen (not shown in FIG. 10), which may include any of the specimens described herein, for imaging applications or any other applications described herein. The embodiment shown in FIG. 10 may be further configured as described herein. In addition, the embodiment shown in FIG. 10 may be included in any of the systems described herein.

As shown in FIG. 11, excitation beam 142 from an excitation source (not shown in FIG. 11), which may include an electron beam, an X-ray beam, a particle beam, a laser beam, or any other excitation radiation, is directed to focusing optics that include refractive optical element 144. Refractive optical element 144 may be further configured as described herein. For example, the refractive optical element may include one or more lenses that are configured to focus the excitation beam to plasma 146. As further shown in FIG. 11, the focusing optics may also include reflective optical element 148. A portion of the excitation beam that passes through plasma 146 may be collected by reflective optical element 148, which may be configured to focus the portion of the excitation beam that passed through the plasma back to the plasma. Reflective optical element 148 may include a spherical mirror, an elliptical mirror, or any other suitable reflective optical element, all of which may be further configured as described herein.

Reflective optical element 148 may include aperture 150 configured such that nozzle 152 and/or gas jet 154 can pass through the aperture. In this manner, nozzle 152 may be configured to direct gas jet 154 through reflective optical element 148 to plasma 146. Nozzle 152 may be further configured as described herein. The gas jet may also be further configured as described herein. Light (not shown in FIG. 11) generated by plasma 146 such as DUV light and/or any other light described herein may be collected and directed to other optical components (not shown in FIG. 11), which may include any of the optical components of any of the illumination subsystems described herein, such that the light can be directed to a specimen (not shown in FIG. 11), which may include any of the specimens described herein, for imaging applications or any other applications described herein. The embodiment shown in FIG. 11 may be further configured as described herein. In addition, the embodiment shown in FIG. 11 may be included in any of the systems described herein.

Jet-based pumped plasmas have a number of features. For example, in one embodiment, the gas flow subsystem is configured to direct a gas to the plasma through a sonic or supersonic nozzle to reduce a volume of the plasma and to reduce absorption of the generated light by the gas. In one such example, a supersonic nozzle can be used for relatively high pressure or vacuum conditions. One benefit of such a configuration is that target gas or liquid density is relatively high at the jet and relatively low outside thereby limiting the light emitting volume and limiting self absorption of UV light by "cold gas." In another embodiment, the gas flow system includes a cylindrical-shaped nozzle. In an additional embodiment, the gas directed to the plasma increases uniformity of a density profile of the plasma. For example, another feature of a jet-based pumped plasma is that a cylindrical nozzle design can be optimized to generate a substantially uniform density profile for laser excited plasmas. In a further embodiment, the gas directed to the plasma creates an interaction media having a density suitable for interactions between the excitation light and the plasma. For example, an additional feature of a jet-based pumped plasma is that gas jets can be used to create a suitable density interaction media for laser plasma interactions. In some embodiments, the focusing optics are configured to direct the excitation light to one or more edges of the gas jet thereby affecting a shape of the gas jet. For example, a further feature of a jet-based pumped plasma is that a laser pulse can be focused with a spherical or axial lens onto the edge of the gas jet to generate a preformed shape. (See, for example, V. Malka et al., "Channel Formation in Long Laser Pulse Interaction with a Helium Gas Jet" Phys. Rev. Lett. 16, 2979, 1997, which discloses that plasma expansion is governed by a thermal wave during the laser pulse; K. Krushelnick, A. Ting, C. I. Moore, H. R. Burris, E. Esarey, P. Sprangle, and M. Baine, "Plasma Channel Formation and Guiding during High Intensity Short Pulse Laser Plasma Experiments" Phys. Rev. Lett. 78, 4047, 1997; and S. P. Nikitin, T. M. Antonsen, T. R. Clark, Y. Li, and H. M. Milcherg, "Guiding of intense femtosecond pulses in preformed plasma channels," Opt. Lett. 22, 1787, 1997, each of which is incorporated by reference as if fully set forth herein.)

In another embodiment, a pressure of the gas directed to the plasma is selected based on one or more predetermined characteristics of the plasma. For example, yet another feature of a jet-based pumped plasma is that controlling the gas flow using a sonic or a supersonic nozzle is preferable to provide the desired interaction plasma density profile. When creating a plasma using a gas jet, the desired density can be reached by varying or choosing the initial gas pressure. An additional feature of a jet-based pumped plasma is that changing the gas pressure can vary the initial neutral density. In an additional embodiment, the gas flow subsystem includes a nozzle through which the gas is directed to the plasma, and a diameter of the nozzle is selected based on one or more predetermined characteristics of the plasma. For example, a further feature of a jet-based pumped plasma is that changing the nozzle diameter can change the plasma length.

In one embodiment, the system is configured to apply an external magnetic field to the plasma to alter one or more characteristics of the plasma. For example, the system may use a magnetic field for pumping light absorption optimization and for plasma shaping. Many of the papers written about LSPLS suggest that IR absorption is mediated by free electrons in the plasma. IR absorption drops significantly as light frequency falls below the plasma frequency. Introduction of a magnetic field would change electron plasma frequency and respectively change the absorption. The target absorption can be adjusted to be higher or lower by adjusting the magnetic field. In addition, the IR absorption coefficient is proportional to the squared ratio of the pumping light frequency to plasma frequency. Therefore, the magnetic field effectively changes plasma frequency. Furthermore, if light absorption and light generation in the UV are dominated by atomic orbital transitions of charged or neutral plasma species, relatively high magnetic fields (e.g., greater than about 3000 Gauss) can be used to broaden the generated light thereby resulting in less self-absorbed radiation.

In some embodiments, an external magnetic field is used for plasma shaping. In such embodiments, one or more magnetic fields may be used to confine and modify the location of the energetic plasma electrons and hence the light emitting region. Such confining and modifying of the location of the energetic plasma electrons can be performed by changing the diffusion parameters, using magnetic wigglers, magnetic bottles, magnetic mirrors, shaping using wiggler magnet arrays (1D, 2D, or 3D), and the use of an external magnetic field to accelerate electrons like that in the undulator of a flee-electron laser for relatively strong focusing of electron trajectories.

In another embodiment, the system includes a gas flow subsystem configured to direct one or more feed materials to the plasma after generation of the plasma. For example, forced gas flow may be used in the electrodeless lamp. Forced gas flow in the electrodeless lamp is similar to the use of a gas jet for the plasma shaping, and forced gas flow can be used in combination with one or more gas jets for the plasma shaping. Forced gas flow can be used to generate a non-equilibrium plasma (e.g., to effectively reduce relaxation time or to reduce pumped gas temperature). For example, forced gas flow can be used for $H_2$ and $D_2$ pumping. In this case, the continuum UV irradiation is formed by the excited molecules and followed by dissociation of these molecules. The forced gas flow will deliver new molecules to be excited in the plasma zone.

In a further embodiment, ignition methods that can be used to initiate the plasma include light pulse, electrical, RF, or some combination thereof. For example, as described above, the system may include a pulsed light source, an RF coil, a voltage source external to the lamp, or some combination thereof configured to initiate the plasma.

In an additional embodiment, relatively high purity oases are used. As used herein, the term "relatively high purity gases" generally refers to gases with levels of impurities about 3 orders of magnitude lower than the usual levels of impurities in gases used in discharge lamp applications. Relatively high purity gases may be used for contamination protection since even relatively low levels of impurities can significantly affect windows and surfaces of other optical elements. In addition, relatively high purity gases may be used for efficiency optimization since the level(s) of impurities can affect the temperature in the plasma, especially electron temperature. Using relatively high purity gases may also include adding relatively small controlled amounts of impurities (e.g., oxygen) to the gases.

In one embodiment, the system includes a cleaning subsystem configured to remove photocontamination from one or more optical elements of the focusing optics, one or more optical elements of the system, or some combination thereof. For example, the embodiments described herein may be configured for photocontamination control and purged optics (e.g., of both UV and IR components). For example, both UV and pumping IR light may cause significant photocontamination. A photocontamination control environment is preferable for all (UV and IR) optics. The photocontamination control environment may be created using optics purging and providing a substantially exactly dosed amount of ozone for the cleaning. Ozone can be generated by either UV light generated by the plasma or by special ozone generation. Some oxygen can be added to the target gas as well.

In one embodiment, the plasma is generated from one or more feed materials that include a liquid. For example, the embodiments described herein may also be configured for the use of liquid targets. An important characteristic of the target is the density of the atoms (or ions). The use of a liquid target allows increases in, and even maximization, of the plasma density. In order to form a plasma and to transfer generated light from the plasma area, a jet configuration is preferably used.

Figure 12:
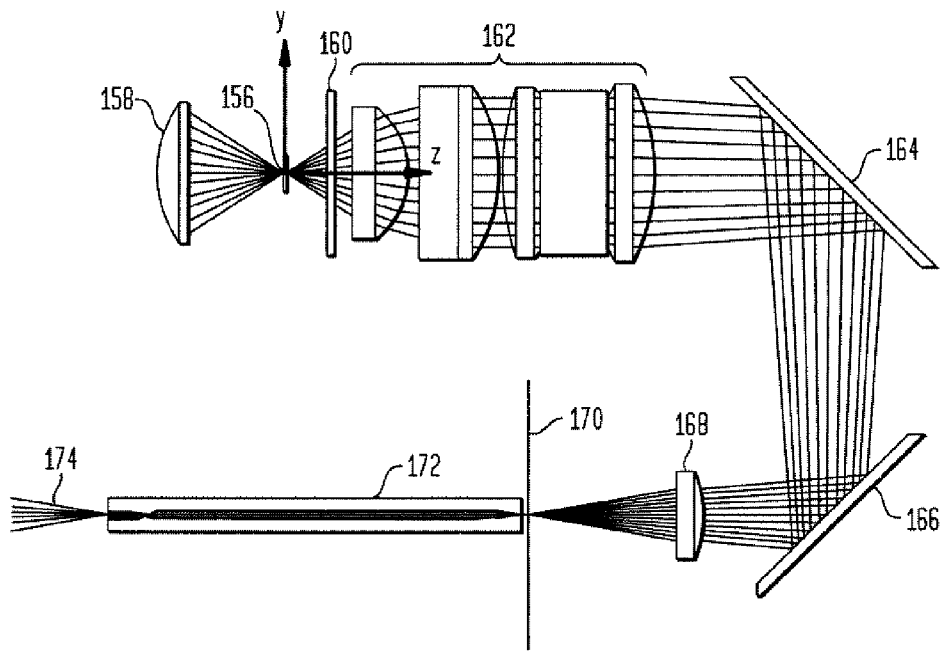
FIG. 12 is a schematic diagram illustrating a side view of one embodiment of focusing optics configured to focus excitation light to a plasma in an electrodeless lamp such that the plasma generates light and one embodiment of a portion of an illumination subsystem configured to illuminate a specimen during a process with the light generated by the plasma.
Figure 13:
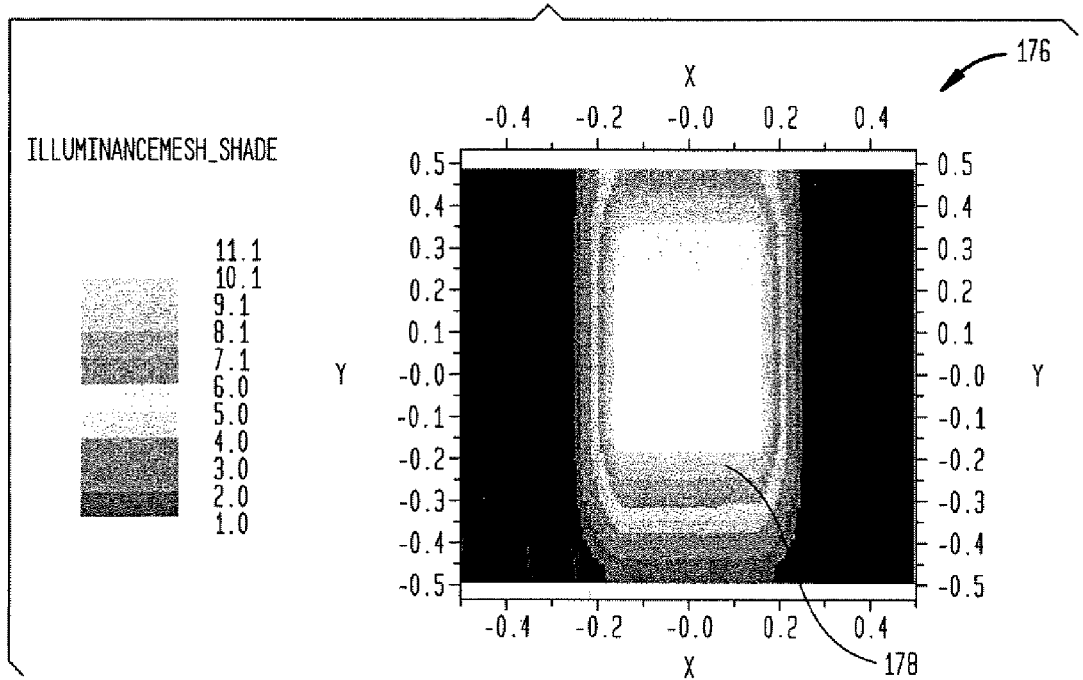
FIG. 13 is a plot illustrating illuminance as a function of x and y position within a source plane of the illumination subsystem shown in FIG. 12.

Further description provided herein generally relates to excitation light (e.g., IR beam) delivery configurations. In one embodiment, the system includes an illumination subsystem configured to illuminate the specimen during the process with the light generated by the plasma. In one such embodiment, the illumination subsystem includes a reflective optical element configured to collect the light generated by the plasma and to direct the collected light to one or more refractive optical elements of the illumination subsystem. For example, FIGS. 12 and 13 illustrate the mapping of light coupling in a (refractive) illumination subsystem used in the 2367 system that is commercially available from KLA-Tencor. As shown in FIG. 12, the illumination subsystem may include reflective optical element 158 configured to collect the light generated by plasma 156 and to direct the collected light to one or more refractive optical elements (e.g., condenser lens 162) of the illumination subsystem. In particular, as shown in FIG. 12, light from plasma 156, which may be configured according to any of the embodiments described herein, is collected by reflective optical element 158. Reflective optical element 158 may be a spherical mirror, an elliptical mirror, or any other suitable reflective optical element, and may be further configured as described herein. Light collected by reflective optical element 158 is focused through plasma 156 and this light along with other light from the plasma is directed in the z direction shown in FIG. 12. The light from the plasma may include UV light and/or any other light described herein.

The system may also include filter 160 through which the light from plasma 156 and reflective optical element 158 may pass. Filter 160 may include any suitable filter such as a spectral filter. The illumination subsystem may also include condenser lens 162, which as shown in FIG. 12 includes a number of refractive optical elements, which may include any suitable refractive optical elements known in the art. Light that passes through filter 160 may be directed to condenser lens 162, which is configured to direct the light to reflective optical element 164. Reflective optical element 164 may be a flat mirror or any other suitable reflective optical element known in the art. Reflective optical element 164 is configured to direct the light to reflective optical element 166, which may also be a flat mirror or any other suitable reflective optical element known in the art. Reflective optical element 166 is configured to direct the light to refractive optical element 168, which is configured to focus the light to source plane 170 positioned at or proximate to the entrance of homogenizer 172, which may be configured as described herein. Light 174 exiting homogenizer 172 may be directed to additional optical components of the illumination subsystem such that the light can be directed onto a specimen such as any of the specimens described herein. The embodiment shown in FIG. 12 may be included in any of the systems described herein. In addition, the embodiment shown in FIG. 12 may be further configured as described herein.

Simulation of the 2367 illumination subsystem shows that 90% of light can be coupled into the homogenizer if the plasma and its image from the backing mirror (reflective optical element 158) are contained within an area of about 3.8 mm×about 0.7 mm. For example, as shown in FIG. 13, plot 176 shows illuminance as a function of x and y positions within the source plane shown in FIG. 12. Plot 176 shown in FIG. 13 illustrates area 178 of the source plane with 90% light coupling into the homogenizer shown in FIG. 12. The goal is to "mold" the plasma inside such a region if possible via laser pumping or other means such as a magnetic field.

Figure 14:
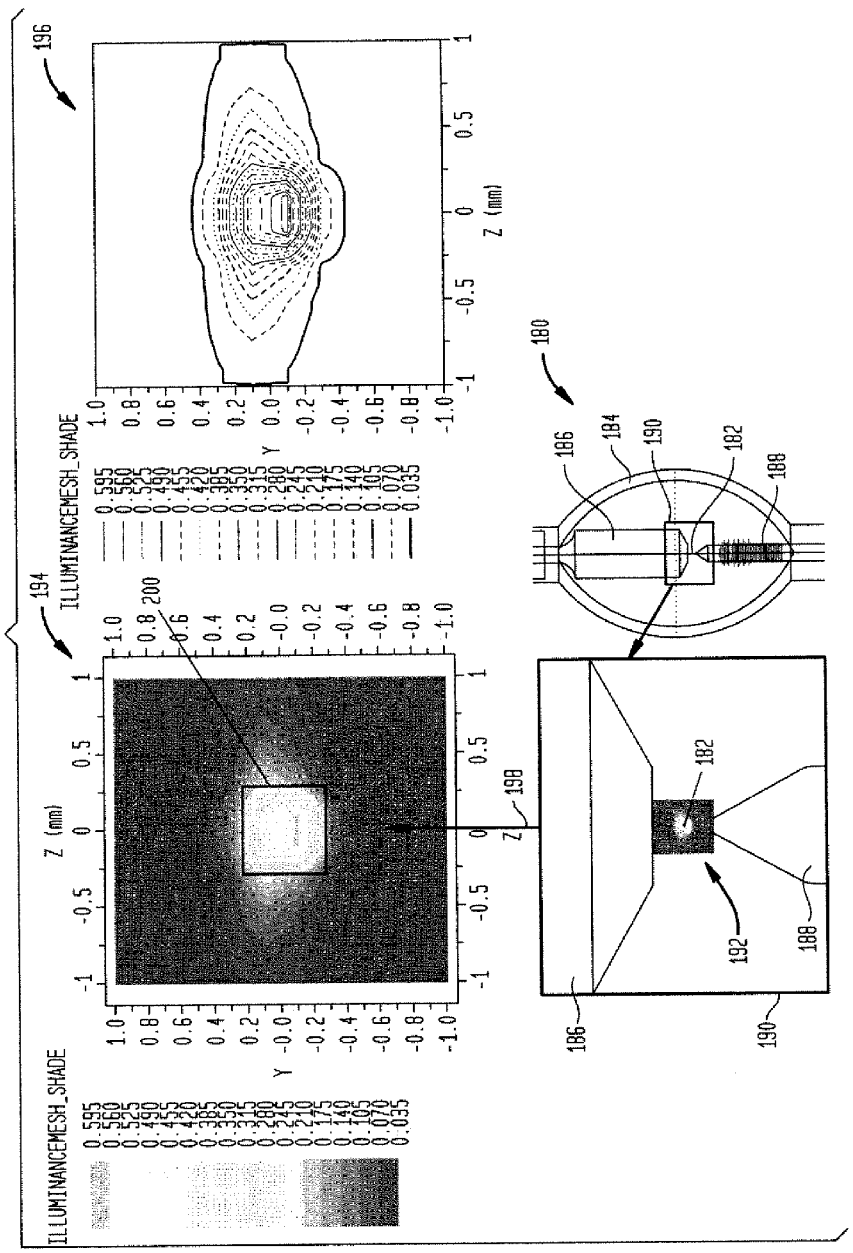
FIG. 14 is a schematic diagram illustrating a cross-sectional view of one embodiment of an electrodeless lamp and plots illustrating illuminance as a function of y and z positions that can be coupled from the lamp into an illumination subsystem.

FIG. 14 illustrates the mapping of light coupling in an (elliptical reflective) illumination subsystem of one system that is commercially available from KLA-Tencor. In particular, FIG. 14 illustrates mapping of $\eta(y, z)$ from a substantially uniform plasma source having a size of about 2 mm×about 2 mm. As shown in FIG. 14, LSP light source 180 may include plasma 182 disposed within lamp 184. Plasma 182 and lamp 184 may be further configured according to any of the embodiments described herein. Anode 186 and cathode 188 are also disposed within lamp 184. Anode 186 and cathode 188 may be further configured as described herein and may have any other suitable configuration. As shown in exploded view of portion 190 of LSP light source 180, gap 192 of about 2 mm may be between anode 186 and cathode 188, and plasma 182 may be disposed in gap 192. Therefore, the plasma source may have a size of about 2 mm by about 2 mm as described above. Plots 194 and 196 shown in FIG. 14 show the illuminance as a function of position in the y and z directions, and light from the plasma (e.g., UV light) is directed along direction 198 in the z direction. As shown in plot 194, area 200 is an area of reasonably good light coupling into the illumination subsystem. Area 200 has dimensions of about 0.6 mm×about 0.5 mm.

Figure 15:
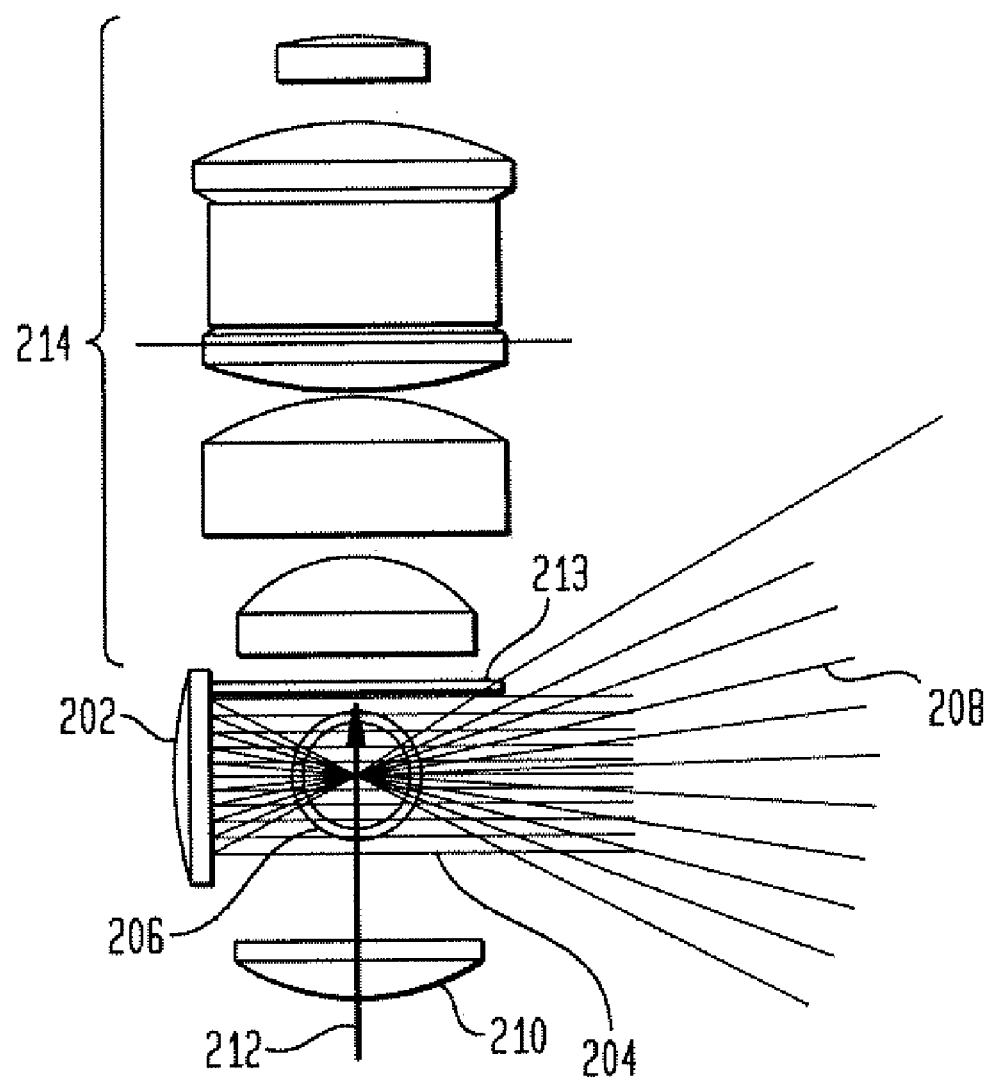
FIG. 15 is a schematic diagram illustrating a side view of an embodiment of focusing optics that include one reflective optical element configured to focus excitation light to a plasma and one embodiment of a portion of an illumination subsystem configured to illuminate a specimen during a process with light venerated by the plasma.

In one embodiment, the focusing optics include a reflective optical element configured to focus the excitation light to the plasma, and the excitation light includes an expanded laser beam. For example, FIG. 15 illustrates one embodiment of a simple approach based on the 2367 illumination subsystem design using one focusing mirror. The simplest way to focus an expanded laser beam to the lamp is to use a reflective mirror. For example, as shown in FIG. 15, the focusing optics include reflective optical element 202 configured to focus expanded laser beam 204 to plasma 206. Reflective optical element 202 may include any of the reflective optical elements described herein (e.g., a spherical mirror, an elliptical mirror, etc.). Expanded laser beam 204 may include any of the excitation light described herein produced by any of the lasers described herein. For example, expanded laser beam 204 may include an IR beam. Plasma 206 may be configured according to any of the embodiments described herein. The maximum NA for such focusing optics (e.g., the maximum NA at which light is directed to plasma 206) may be about 0.5. which may be limited by space. In the system shown in FIG. 15, the returned beam may not be recycled. For example, light 208 that passes through plasma 206 may not be recycled back to the plasma. Such a configuration may be suitable, for example, if plasma absorption is relatively strong such that there is no need to recycle the excitation light.

The portion of the illumination subsystem shown in FIG. 15 includes reflective optical element 210, filter 213, and condenser lens 214. As further shown in FIG. 15, light emitted by plasma 206 (e.g., UV light) may be collected by reflective optical element 210, which may be configured as described herein. For example, reflective optical element 210 may be a spherical mirror, an elliptical mirror, etc. and may function as a backing mirror for the plasma. Light from the plasma collected by reflective optical element 210 and light emitted from plasma in direction 212 may be directed to filter 213, which may include any suitable filter such as a spectral filter configured to alter the wavelength(s) of the light from the plasma that illuminate the specimen (not shown in FIG. 15). Light that exits filter 213 is directed to condenser lens 214, which includes a set of refractive optical elements as shown in FIG. 15. Condenser lens 214 and the refractive optical elements included in the condenser lens may be further configured as described herein. The embodiment shown in FIG. 15 may be further configured as described herein. In addition, the embodiment shown in FIG. 15 may be included in any of the system embodiments described herein.

Figure 16:
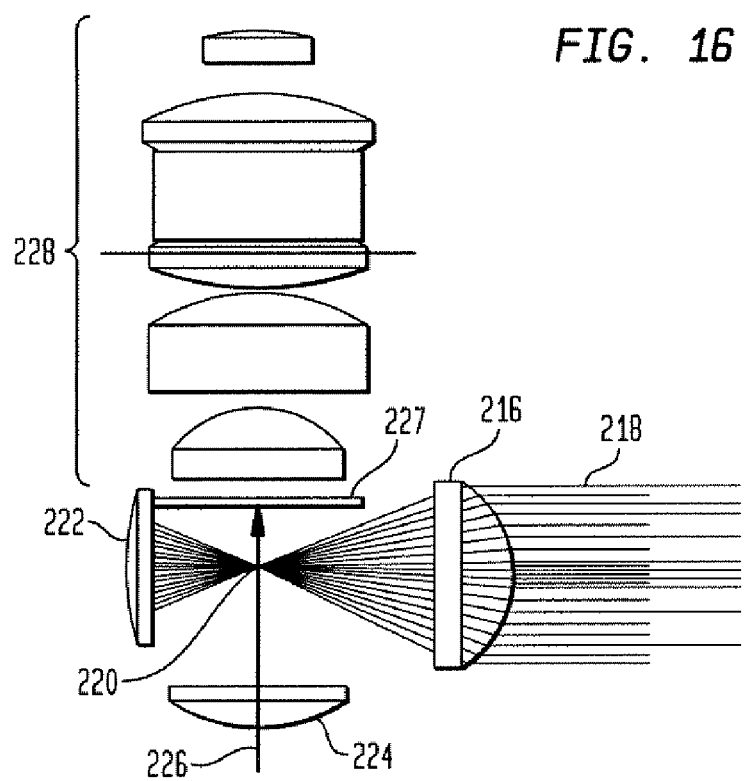
FIG. 16 is a schematic diagram illustrating a side view of an embodiment of focusing optics that include a refractive optical element and a reflective optical element, which in combination are configured to focus excitation light to a plasma, and an embodiment of a portion of an illumination subsystem configured to illuminate a specimen during a process with light generated by the plasma.

FIG. 16 illustrates one embodiment of focusing optics that include a focusing lens/mirror combination. If plasma absorption is not strong, it may be desirable to double pass the excitation light (e g., an IR beam) through the plasma with a lens-mirror combination. For example, as shown in FIG. 16, the focusing optics may include refractive optical element 216. Refractive optical element 216 is configured to focus excitation light 218 to plasma 220. Refractive optical element 216 may be further configured as described herein. Excitation light 218 may include any of the excitation light described herein (e.g., an IR beam) and may be generated by any of the lasers described herein. The focusing optics also include reflective optical element 222. Excitation light focused to plasma 220 by refractive optical element 216 that is not absorbed by the plasma may be collected by reflective optical element 222, which may include any of the reflective optical elements described herein (e.g., a spherical mirror, an elliptical mirror, etc.). Reflective optical element 222 may be configured to collect the excitation light that was not absorbed by the plasma and to focus the collected light back to plasma 220. Therefore, the focusing optics shown in FIG. 16 are configured to pass the excitation light through the plasma twice using the combination of refractive optical element 216 and reflective optical element 222. The maximum NA at which the excitation light may be directed to the plasma by the focusing optics shown in FIG. 16 may be about 0.5, which may be limited by space.

The portion of the illumination subsystem shown in FIG. 16 includes reflective optical element 224, filter 227, and condenser lens 228. As further shown in FIG. 16, light generated by plasma 220 (e.g., UV light) may be collected by reflective optical element 224, which may be configured as described herein. For example, reflective optical element 224 may be a spherical mirror, an elliptical mirror, etc. and may function as a backing mirror for the plasma. Light generated by the plasma collected by reflective optical element 224 and light generated by the plasma in direction 226 may be directed to filter 227, which may include any suitable filter such as a spectral filter configured to alter the wavelength(s) of the light generated by the plasma that are directed to other optical elements of the illumination subsystem. Light that exits filter 227 is directed to condenser lens 228, which includes a set of refractive optical elements as shown in FIG. 16. Condenser lens 228 and the refractive optical elements included in the condenser lens may be further configured as described herein. The embodiment shown in FIG. 16 may be further configured as described herein. In addition, the embodiment shown in FIG. 16 may be included in any of the system embodiments described herein.

Figure 17:
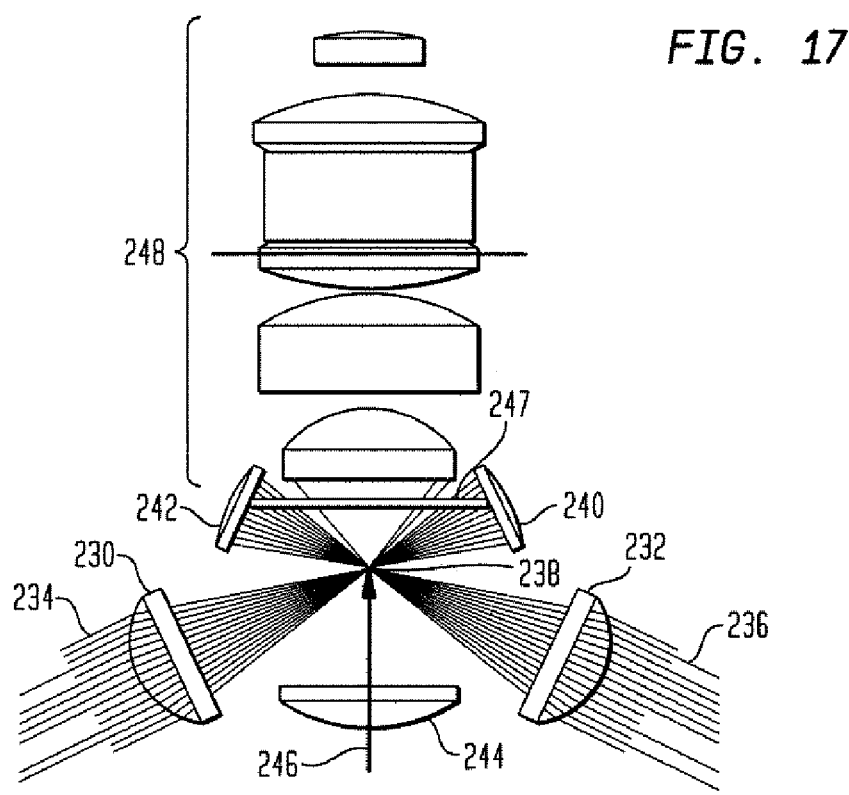
FIG. 17 is a schematic diagram illustrating a side view of an embodiment of focusing optics configured to focus excitation light to a plasma at different directions that cross at or near the plasma and an embodiment of a portion of an illumination subsystem configured to illuminate a specimen during a process with light generated by the plasma.

In one embodiment, the focusing optics are configured to focus the excitation light to the plasma at different directions simultaneously. For example, FIG. 17 illustrates one embodiment of focusing optics configured for cross-beam pumping that can be used with the condenser lens described above. As shown in FIG. 17, the focusing optics may include refractive optical elements 230 and 232, which are configured to focus excitation light 234 and 236, respectively, to plasma 238. Refractive optical elements 230 and 232 may be further configured as described herein. Excitation light 234 and 236 may include any of the excitation light described herein such as IR beams. In addition, the excitation light may be generated by the same laser (e.g., by a single laser configured to direct excitation light to a beam splitter coupled to appropriate light directing components) or by different lasers (e.g., by different lasers each of which is configured to direct light to one of refractive optical elements 230 and 232). As shown in FIG. 17, refractive optical elements 230 and 232 are configured to direct the excitation light to the plasma simultaneously such that the paths of the excitation light from the two refractive optical elements cross in the space at or near the plasma (hence the terms "cross-beam pumping" and "cross-illumination").

The focusing optics may also include reflective optical elements 240 and 242. Excitation light focused to plasma 238 by refractive optical element 230 that is not absorbed by the plasma may be collected by reflective optical element 240, which may include any of the reflective optical elements described herein (e.g., a spherical mirror, an elliptical mirror, etc.). Reflective optical element 240 may be configured to collect the excitation light that was not absorbed by the plasma and to focus that light back to plasma 238. Therefore, the focusing optics shown in FIG. 17 are configured to pass excitation light 234 through the plasma twice using the combination of refractive optical element 230 and reflective optical element 240.

In a similar manner, excitation light focused to plasma 238 by refractive optical element 232 that is not absorbed by the plasma may be collected by reflective optical element 242, which may include any of the reflective optical elements described herein (e.g., a spherical mirror, an elliptical mirror, etc.). Reflective optical element 242 may be configured to collect the excitation light that was not absorbed by the plasma and to focus that light back to plasma 238. Therefore, the focusing optics shown in FIG. 17 are configured to pass excitation light 236 through the plasma twice using the combination of refractive optical element 232 and reflective optical element 242. As shown in FIG. 17, refractive optical elements 230 and 232 are configured to focus the excitation light to the plasma such that the paths of the excitation light from the two refractive optical elements cross in the space at or near the plasma, and reflective optical elements 240 and 242 are also configured to focus the excitation light collected by the reflective optical elements such that the paths of the excitation light from the two reflective optical elements cross in the space at or near the plasma. Therefore, both the excitation light beams and the recycled excitation light beams may be focused to the plasma for cross-beam pumping or cross-illumination.

It is possible to create a more favorable plasma shape with cross-beam illumination such as that shown in FIG. 17. The combination of refractive optical element 230 and reflective optical element 240 and the combination of refractive optical element 232 and reflective optical element 242 (e.g., condenser/mirror pairs) can be configured to have substantially the same or different focal points depending on whether it is desired to have a smaller, brighter plasma volume (e.g., which can be created with substantially the same focal points) or a bigger, shaped plasma volume (e.g., which can be created with different focal points).

The portion of the illumination subsystem shown in FIG. 17 includes reflective optical element 244, filter 247, and condenser lens 248. As further shown in FIG. 17, light generated by plasma 238 (e.g., UV light) may be collected by reflective optical element 244, which may be configured as described herein. For example, reflective optical element 244 may be a spherical mirror, an elliptical mirror, etc. and may function as a backing mirror for the plasma. Light generated by the plasma collected by reflective optical element 244 and light generated by the plasma in direction 246 may be directed to filter 247, which may include any suitable filter such as a spectral filter configured to alter the wavelength(s) of the light generated by the plasma that are directed to other optical elements of the illumination subsystem. Light that exits filter 247 is directed to condenser lens 248, which includes a set of refractive optical elements as shown in FIG. 17. Condenser lens 248 and the refractive optical elements included in the condenser lens may be further configured as described herein. The embodiment shown in FIG. 17 may be further configured as described herein. In addition, the embodiment shown in FIG. 17 may be included in any of the system embodiments described herein.

Figure 18:
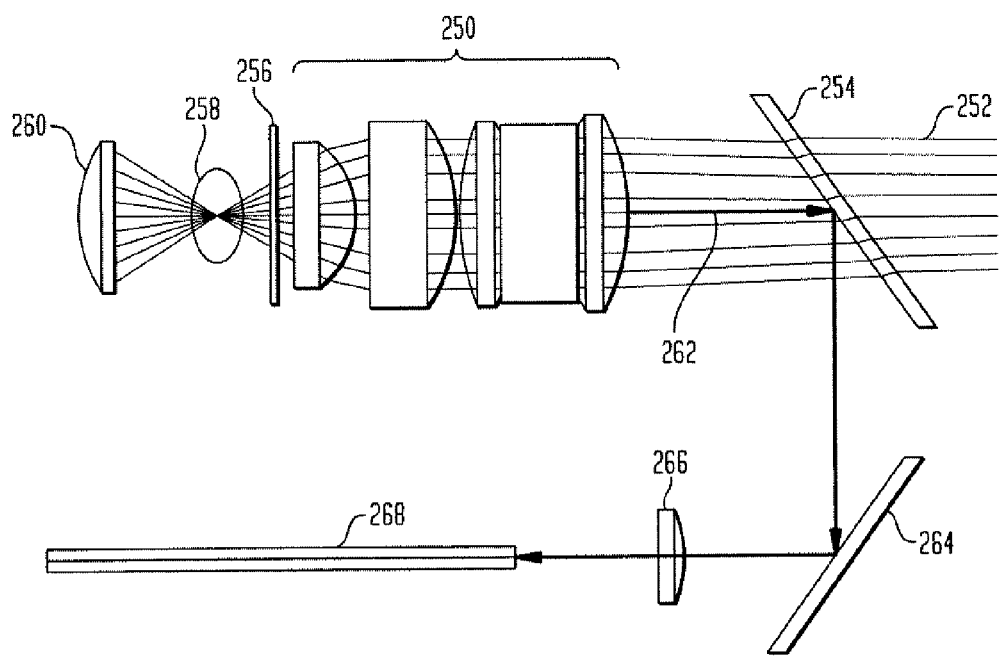
FIG. 18 is a schematic diagram illustrating a side view of an embodiment of focusing optics configured to focus excitation light to a plasma and an embodiment of a portion of an illumination subsystem that includes one or more refractive optical elements configured to focus the excitation light to the plasma.

In one embodiment, the system includes an illumination subsystem configured to illuminate the specimen during the process with the light generated by the plasma. In one such embodiment, the illumination subsystem includes one or more refractive optical elements configured to focus the excitation light to the plasma. For example, FIG. 18 illustrates one embodiment in which a pump beam is directed along the optical axis of the illumination subsystem configuration described above. This configuration may be used if the far-field radiation pattern of the laser-induced plasma is much higher along the pump direction. For example, as shown in FIG. 18, the illumination subsystem may include condenser lens 250, which may be configured as described herein. Excitation light 252 is directed from a laser (not shown in FIG. 18) and/or by one or more optical components such as those described herein through dichroic mirror 254 to condenser lens 250. Excitation light 252 may include any of the excitation light described herein such as IR light, and the laser may include any of the lasers described herein. The dichroic mirror may include any optical component that is substantially transparent to the excitation light (e.g., IR light) and reflects the light generated by the plasma (e.g., UV light).

As further shown in FIG. 18, the excitation light passes through condenser lens 250, and if the system includes filter 256, the excitation light that exits the condenser lens passes through the filter. The condenser lens focuses the excitation light to plasma 258. In this manner, the condenser lens of the illumination subsystem is configured to focus the excitation light to the plasma. In another such embodiment, a matching lens (not shown in FIG. 18) may be used to focus the excitation light (e.g., IR light) through the condenser lens. In a further embodiment, the coating currently used in the illumination subsystem may be re-designed (e.g., such that the excitation light can be focused by the condenser lens to the plasma). Furthermore, the illumination subsystem may be designed based on possible laser damage of the components of the illumination subsystem (e.g., to reduce and even prevent damage of the condenser lens by the excitation light).

Plasma 258 may be configured according to any of the embodiments described herein. If a portion of the excitation light passes through the plasma (is not absorbed by the plasma), that portion of the excitation light may be collected by reflective optical element 260, which may include any of the reflective optical elements described herein (e.g., a spherical mirror, an elliptical mirror, etc.) and may be further configured as described herein. The portion of the excitation light that is collected by reflective optical element 260 may be focused by the reflective optical element to plasma 258. In one such embodiment, the NA at which the excitation light is focused to the plasma may be about 0.65.

Light (e.g., UV light and/or any other light described herein) that is generated by plasma 258 may be collected by reflective optical element 260 and condenser lens 250. Reflective optical element 260 and condenser lens 250 may be configured to direct the light generated by the plasma along direction 262. The light that is generated by plasma 258 and directed along direction 262 may be reflected by dichroic mirror 254 to reflective optical element 264, which may include any suitable reflective optical element known in the art such as a flat mirror. Light from dichroic mirror 254 is reflected by reflective optical element 264 such that the light is directed to refractive optical element 266, which may include any refractive optical element (e.g., a focusing lens) described herein and may be further configured as described herein. Refractive optical element 266 is configured to focus the light to the entrance of homogenizer 268, which may include any of the homogenizers described herein (e.g., a light pipe) and may be further configured as described herein. The embodiment shown in FIG. 18 may be further configured as described herein. In addition, the embodiment shown in FIG. 18 may be included in any of the system embodiments described herein.

Figure 19:
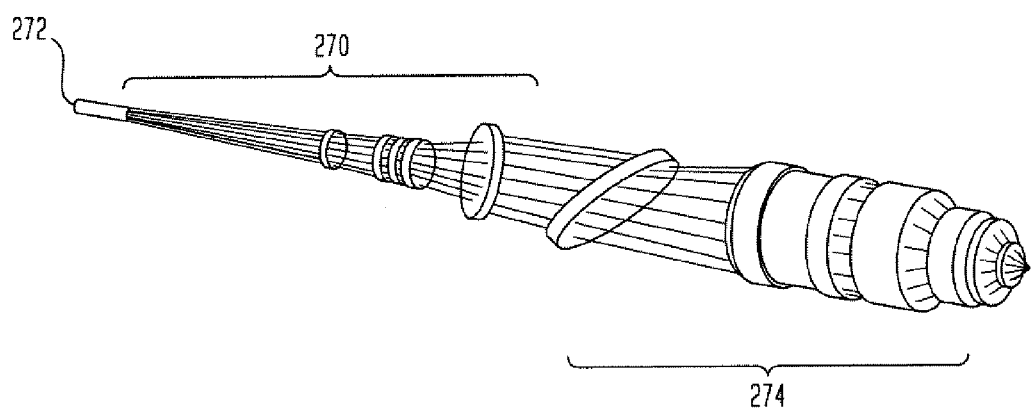
FIG. 19 is a schematic diagram illustrating a perspective view of an embodiment of a portion of an illumination subsystem that includes one or more refractive optical elements configured to focus excitation light to a plasma.

FIG. 19 illustrates one embodiment of a lens group that can be used to couple excitation light (e.g., IR light) to a plasma (and therefore a LSP light source or lamp) through the condenser lens described above. For example, coupling lens group 270 may be configured to couple light from laser 272, which may include any of the lasers described herein, to condenser lens 274. As shown in FIG. 19, the coupling lens group may include a number of refractive optical elements. Although one particular configuration of the coupling lens group is shown in FIG. 19, such a coupling lens group may have any suitable configuration, which may vary depending on, for example, the configuration of condenser lens 274. The coupling lens group may be used as a matching lens to focus the excitation light (e.g., IR light) through the condenser lens. Condenser lens 274 may be configured to focus the excitation light to a plasma as described herein (e.g., as described and shown in FIG. 18).

Figure 20:
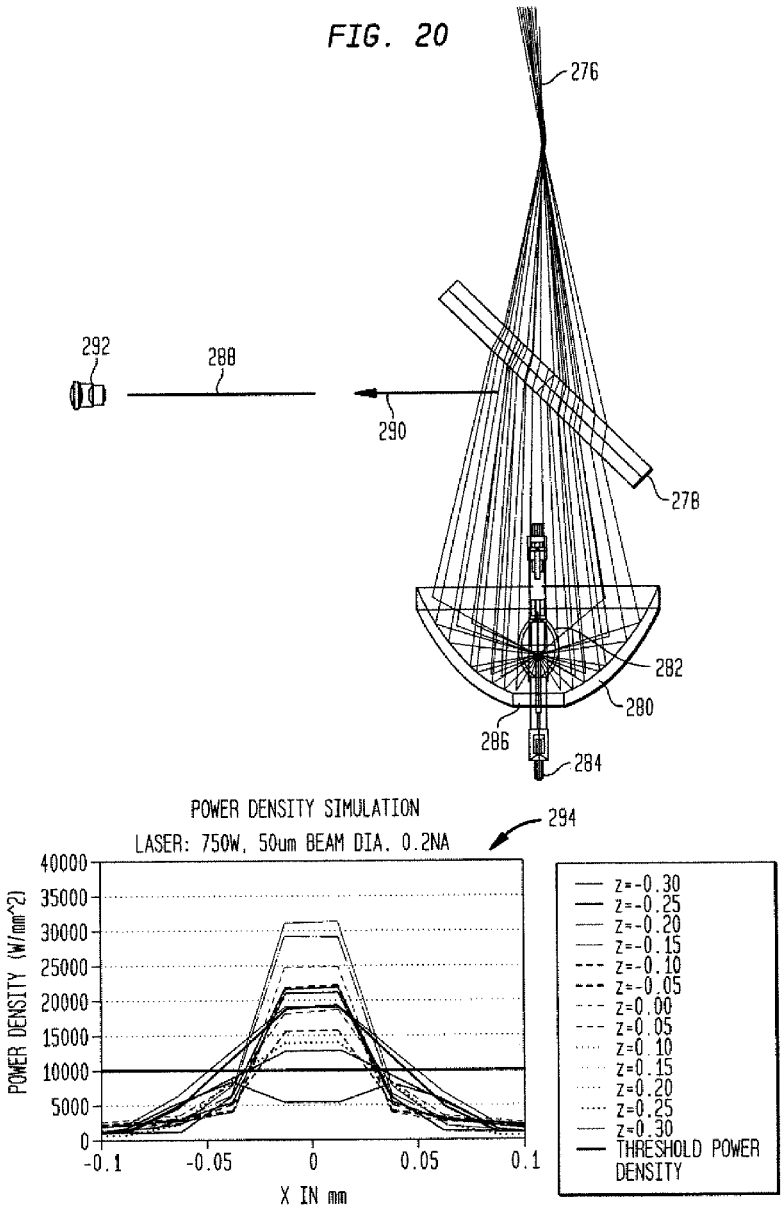
FIGS. 20-22 are schematic diagrams illustrating a cross-sectional view of various embodiments of focusing optics configured to focus excitation light to a plasma and a portion of an illumination subsystem configured to illuminate a specimen during a process with light generated by the plasma.

In one embodiment, the focusing optics include at least one optical element configured to focus the excitation light to the plasma and configured to collect the light generated by the plasma. In one such embodiment, the at least one optical element includes a reflective optical element. FIG. 20 illustrates one embodiment of focusing optics that include such an optical element that may be used to couple excitation light (e.g., IR light) to a lamp. For example, as shown in FIG. 20, excitation light 276 is directed to cold mirror 278. Excitation light 276 may include any of the excitation light described herein that is generated by any of the lasers described herein (e.g., an IR laser). Cold mirror 278 may include a dichroic mirror or any other optical element that is configured to substantially transmit the excitation light (e.g., IR light) and to substantially reflect the light generated by the plasma (e.g., UV light). The excitation light may be distorted as it passes through the cold mirror (e.g., due to refraction of the excitation light by the cold mirror). In some embodiments, a lens group (not shown in FIG. 20) such as coupling lens group 270 shown in FIG. 19 or any other suitable lens or lenses may be positioned in the path of the excitation light before the excitation light passes through the cold mirror. The lens group may be included in the focusing optics to improve coupling of the excitation light to the cold mirror.

The focusing optics include reflective optical element 280 that is configured to focus the excitation light to the plasma. The excitation light that passes through the cold mirror may be collected by reflective optical element 280, which may include any suitable reflective optical element (e.g., a spherical mirror, an elliptical mirror, or any other suitable reflective optical element) and may be further configured as described herein. LSP light source or lamp 282 is disposed in the reflective optical element. For example, LSP light source 282 may be disposed at one focal point of the reflective optical element such that the reflective optical element can focus the excitation light to the LSP light source. LSP light source 282 may be positioned at the focal point of the reflective optical element by mounting 284 that extends through aperture 286 in reflective optical element 280 and couples the LSP light source to another portion (not shown) of the system. Mounting 284 may include any suitable mounting known in the art. LSP light source 282 may be further configured as described herein.

Reflective optical element 280 is also configured to collect the light generated by the plasma. Light (e.g., UV light and/or any other light described herein) generated by LSP light source 282 is collected by reflective optical element 280 and is directed to cold mirror 278. Cold mirror 278 is configured to direct the generated light collected by reflective optical element 280 to homogenizer 288 by reflecting the generated collected light in direction 290. Homogenizer 288 may include a light pipe or any other suitable homogenizer and may be further configured as described herein. The light exiting homogenizer 288 may be directed to one or more other optical components of the illumination subsystem (e.g., such as optical component 292, which may include an objective lens or any other suitable optical component) such that the light can be directed to a specimen thereby illuminating the specimen. The embodiment shown in FIG. 20 may be further configured as described herein and may be included in any of the systems described herein.

Plot 294 shown in FIG. 20 is a power density simulation for the embodiment shown in FIG. 20. In particular, plot 294 illustrates power density as a function of position in the x direction for different values of z. The simulation was performed for an IR laser having a power of 750 W, a 50 µm beam diameter, and an NA of 0.2. As shown in plot 294, the maximum power density is achieved for a value of z=0.15.

Figure 21:
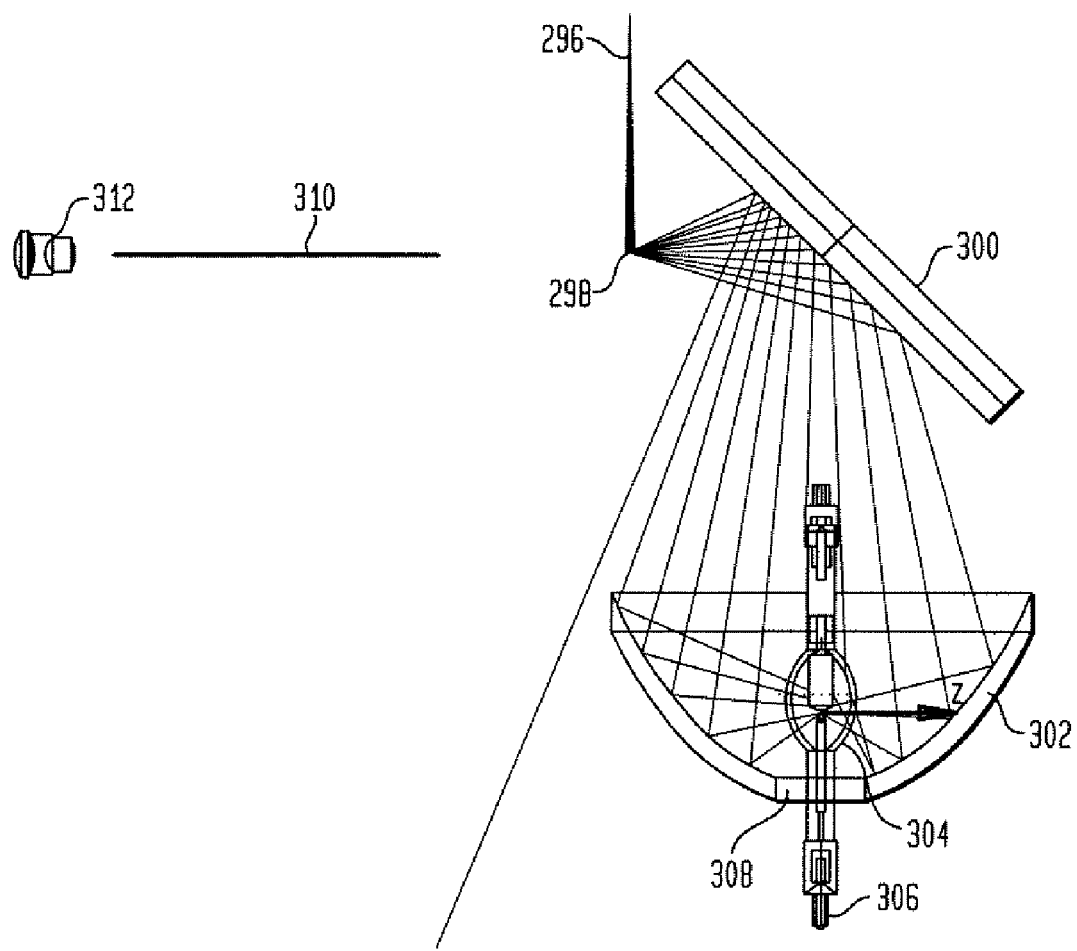
Figure 22:
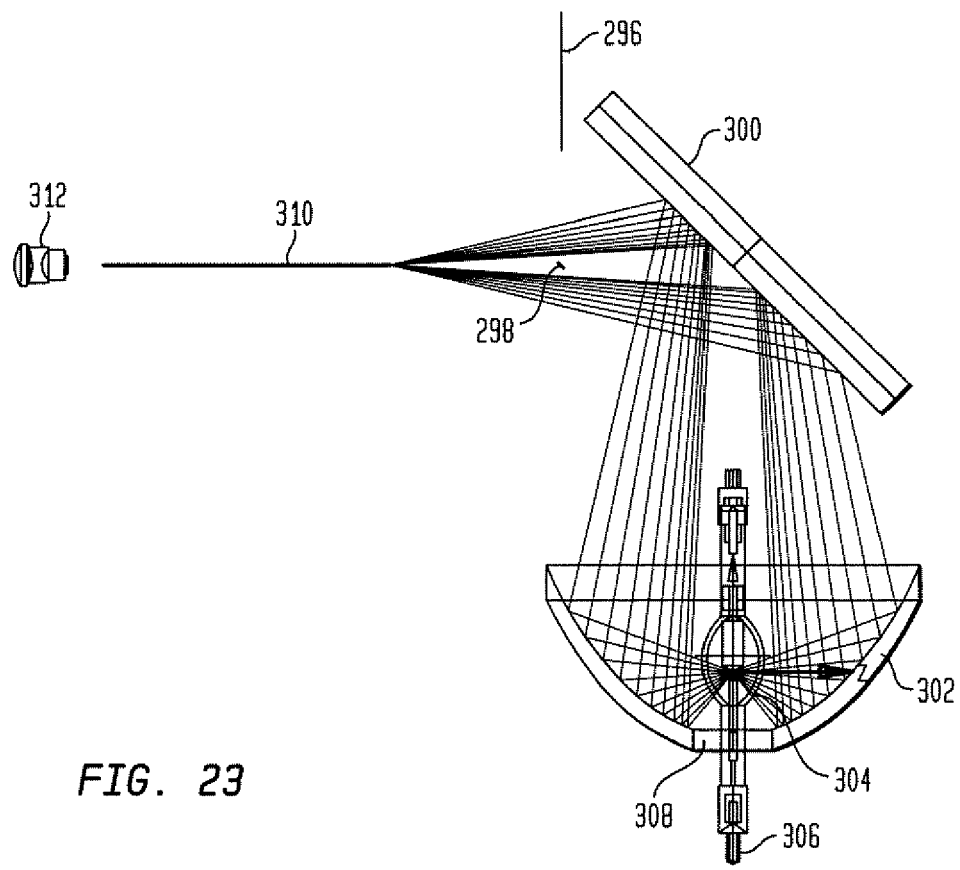

FIGS. 21-22 illustrate another embodiment of focusing optics that may be used to focus excitation light (e.g., IR light) to a lamp. FIG. 21 illustrates the excitation light beam path (e.g., the IR beam path), and FIG. 22 illustrates the generated light beam path (e.g., the UV beam path). This approach bypasses astigmatism from the cold mirror shown in FIG. 20.

For example, as shown in FIG. 21, excitation light 296 (e.g., an IR beam) from a laser (not shown in FIGS. 21 and 22) is directed to reflective optical element 298, which may be a flat mirror or any other suitable reflective optical element. Reflective optical element 298 is configured to direct the excitation light to reflective optical element 300, which may also be a flat mirror or any other suitable reflective optical element. Reflective optical element 300 is configured to direct the excitation light to reflective optical element 302, which may include any suitable reflective optical element (e.g., a spherical mirror, an elliptical mirror, or any other suitable reflective optical element) and may be further configured as described herein.

LSP light source or lamp 304 is disposed in reflective optical element 302. For example, LSP light source 304 may be disposed at one focal point of reflective optical element 302 such that the reflective optical element can focus the excitation light to a plasma (not shown in FIGS. 21 and 22) in the LSP light source. LSP light source 304 may be positioned at the focal point of reflective optical element 302 by mounting 306 that extends through aperture 308 in reflective optical element 302 and couples the LSP light source to another portion (not shown) of the system. Mounting 306 may include any suitable mounting known in the art. LSP light source 304 may be further configured as described herein.

As shown in FIG. 22, light (e.g., UV light and/or any other light described herein) generated by LSP light source 304 is collected by reflective optical element 302 and is directed to reflective optical element 300. Reflective optical element 300 is configured to reflect the generated light collected by reflective optical element 302 to homogenizer 310. Reflective optical element 298 may preferably be positioned inside the obscuration of the NA caused by insertion of lamp 204 into reflective optical element 302. Therefore, reflective optical element 298 may not cause further obscuration of the NA. Homogenizer 310 may include a light pipe or any other suitable homogenizer and may be further configured as described herein. The light exiting homogenizer 310 may be directed to one or more other optical components of the illumination subsystem (e.g., such as optical component 312, which may include an objective lens or any other suitable optical component) such that the light can be directed to a specimen thereby illuminating the specimen. The embodiment shown in FIGS. 21 and 22 may be further configured as described herein and may be included in any of the systems described herein.

Additional embodiments described herein generally relate to relatively efficient light collectors for illumination subsystems that use a combination of elliptical and spherical reflectors for optical inspection and/or any other processes described herein. The embodiments described further herein can be used with current illumination subsystems that utilize elliptical reflectors so that retrofit and upgrade of these illumination subsystems can be performed efficiently and cost effectively. In addition, the embodiments described further herein are configured to improve the light collection efficiency and the pupil-fill uniformity simultaneously. Furthermore, the embodiments described further herein can advantageously perform NA space folding which balances out the severe decrease of the high NA power due to shrinking plasma size, which is essential to improve the light collection efficiency. For example, the size of the plasmas described herein are much smaller than the size of currently used discharge arc lamps. The smaller size of the plasma causes much more non-uniformity in the pupil fill of illumination subsystems currently used with discharge arc lamps.

In some embodiments, the system includes an illumination subsystem configured to illuminate the specimen during the process with the light generated by the plasma. In one such embodiment, the illumination subsystem is configured to collect the light generated by the plasma across a solid angle of about $4\pi$. For example, the embodiments described herein can utilize the full $4\pi$ solid angle, which is the theoretical maximum.

Figure 23:
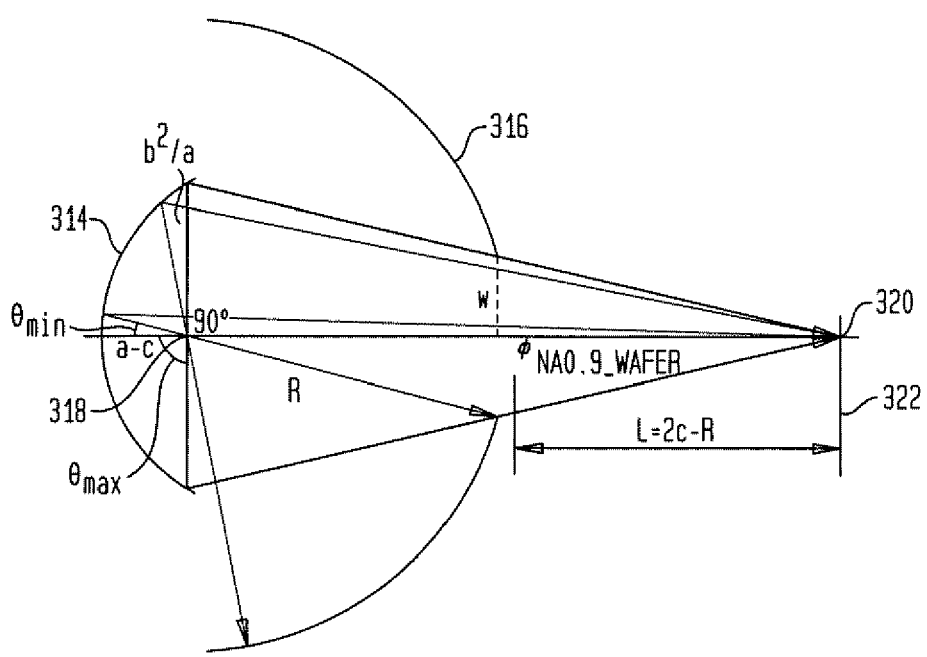
FIG. 23 is a schematic diagram illustrating a cross-sectional view of one embodiment of a portion of an illumination subsystem configured to illuminate a specimen during a process with light generated by a plasma.

In one embodiment, the illumination subsystem includes a partial elliptical reflector and a half spherical reflector. For example, as shown in FIG. 23, the illumination subsystem may include partial elliptical reflector 314 and half spherical reflector 316. Therefore, the illumination subsystem utilizes a partial elliptical reflector in combination with a half spherical reflector for collection of the light generated by the plasma. In one such embodiment, the plasma is positioned at one focal point of the partial elliptical reflector, and the half spherical reflector is substantially centered to the plasma. For example, a plasma (not shown in FIG. 23) may be positioned at focal point 318 of the partial elliptical reflector, and half spherical reflector 316 may be substantially centered to the plasma positioned at focal point 318. In this manner, the half spherical reflector is centered to one of the foci of the partial elliptical reflector at which the plasma will be located.

The partial elliptical reflector may be a partial elliptical reflector included in current illumination subsystems so that, as mentioned above, retrofit and upgrade of these illumination subsystems can be performed efficiently and cost effectively. As such, the partial elliptical reflector may or may not have the same configuration as currently used partial elliptical reflectors. For example, parameters of the partial elliptical reflector may or may not be:

a=about 235,000 mm, where a=the long axis of the partial elliptical reflector;

b=about 123,390 mm, where b=the short axis of the partial elliptical reflector;

c=about 200,000 mm, where $$c = \sqrt{a^2 - b^2};$$

e=about 0.851064, where e=eccentricity;

F1=about 35 mm;

F2=about 435 mm;

EPD=about 195.02 mm, where EPD is the entrance pupil diameter or the diameter of the largest opening of the partial elliptical reflector; and central obscuration diameter=about 42 mm, where the central obscuration diameter is the smaller opening in the partial elliptical reflector that allows elements that mount the electrodeless lamp at the first focal point of the partial elliptical reflector to pass through the partial elliptical reflector to one or more other elements of the system.

In addition, the collection angle of the partial elliptical reflector may be about 120 degrees (the collection angle for oversize collection or over-illumination), and the collection angle for an NA of about 0.9 at the specimen (e.g., wafer) may be about 111 degrees.

The parameters (e.g., R (the radius of the half spherical reflector), EPD, central obscuration diameter, etc.) of the half spherical reflector may be determined using the following equations:

$\sin \phi_{NA\ 0.9 wafer} = 0.24$ $$\tan\phi_{NA0.9wafer} = \frac{a^2 - c^2}{2ac} = \frac{1 - e^2}{2e}$$

$$\sin\phi_{NA0.12waferCMO_{obscuration}} = 0.032$$

$$\tan\phi_{NA0.12waferCMO\_obscuration} = \frac{y}{x + c}$$

$$\frac{x^2}{a^2} + \frac{y^2}{b^2} = 1$$

$$\tan\theta\min = \frac{y}{x - c}$$

$$\frac{x^2}{a^2} + \frac{y^2}{b^2} = 1$$

$$R = ra$$

$$\sin\theta_{min} = \frac{b^2}{aR}\left[1 - \frac{R\cos\theta_{min}}{2c}\right]$$

$$r = (1 - e^2)\frac{\cos\phi_{NA0.9wafer}}{\sin(\theta_{min} + \phi_{NA0.9wafer})}$$

$$w = ra \sin\theta_{min}$$

$$\theta_{max} = 180° - \theta_{min}$$

$$L = 2c - R$$

In another embodiment, the partial elliptical reflector and the half spherical reflector are configured to collect the light generated by the plasma. The half spherical reflector is configured to direct the light collected by the half spherical reflector to the partial elliptical reflector. The partial elliptical reflector is configured to direct the light from the half spherical reflector and the light collected by the partial elliptical reflector to another optical element of the illumination subsystem. For example, as shown in FIG. 23, partial elliptical reflector 314 is configured to direct the light from half spherical reflector 316 and the light collected by the partial elliptical reflector to focal point 320 of the partial elliptical reflector at which another optical element of the illumination subsystem may be positioned or downstream of which another optical element of the illumination subsystem may be positioned. Therefore, the position of focal point 320 may define the location of intermediate image plane 322 of the illumination subsystem. The pupil plane (not shown) of the illumination subsystem shown in FIG. 23 may be downstream of the image plane shown in FIG. 23 and may vary depending on the configuration of other optical elements included in the illumination subsystem.

In this manner, the light generated by the plasma in the solid angle from about 0 degrees to about 90 degrees will be collected by the partial elliptical reflector and focused to the second foci of the partial elliptical reflector. The light generated by the plasma in the solid angle from about 90 degrees up to about 180 degrees will be reflected by the half spherical mirror back through the first focal point of the partial elliptical reflector and will be recollected by the partial elliptical reflector, which is configured to focus the light reflected by the half spherical reflector to the second foci of the partial elliptical reflector. Therefore, using a half spherical reflector in combination with a partial elliptical reflector as described herein allows for collection of the light generated by the plasma across a much larger solid angle thereby increasing the collection efficiency of the illumination subsystem compared to illumination subsystems that include only the partial elliptical reflector. Increasing the collection efficiency of the illumination subsystem advantageously increases the brightness of the light generated by the plasma that can be used to illuminate the specimen. For example, the brightness of the light collected by an illumination subsystem including the partial elliptical reflector and half spherical reflector described herein may be about 1.3 times the brightness of the light collected by an illumination subsystem that includes only the partial elliptical reflector described herein.

In addition, an optical element of the illumination subsystem such as a homogenizer, collection optics, or a condenser lens, all of which may be configured as described further herein, may be positioned at the second foci of the partial elliptical reflector or positioned in the path of the light focused to the second foci such that the optical element can collect the light focused to the second foci of the partial elliptical reflector. In this manner, the illumination subsystem may illuminate a specimen as described further herein with the light from the plasma focused to the second foci of the partial elliptical reflector.

In some embodiments, the illumination subsystem described above is configured to direct the light to a pupil plane of the system such that the light has a substantially uniform intensity across the pupil plane. For example, the reflection from the half spherical reflector acts as a folding action in pupil space such that the final pupil fill includes the pupil fill due to the partial elliptical reflector, which decreases monotonically as NA increases, and the second pupil fill due to the combination of the half spherical reflector and the partial elliptical reflector, which increases monotonically. As a result, the final pupil fill is much more uniform than the pupil fill from the partial elliptical reflector alone.

For example, the pupil intensity at 0.9 NA normalized to the peak pupil intensity may be about 10% when using the partial elliptical reflector without the half spherical reflector described herein. In other words, the intensity of the light at the edge of the pupil may only be about 10% of the peak intensity in the pupil. Such relatively large variation in the intensity of the light at the pupil plane is at least partially due to the fact that the magnification of the partial elliptical reflector varies across the partial elliptical reflector. Such variation in the magnification of the partial elliptical reflector causes rays that are reflected from different points on the partial elliptical reflector to have different intensities at the second focal point of the partial elliptical reflector and therefore at the pupil plane of the illumination subsystem. In particular, light rays reflected at relatively small angles from the partial elliptical reflector are relatively bright at the pupil plane while light rays reflected at relatively large angles from the partial elliptical reflector are relatively dim. As such, using the partial elliptical reflector without the half spherical reflector as described herein produces substantial non-uniformity in intensity across the pupil plane of the illumination subsystem.

In contrast, the pupil intensity at 0.9 NA normalized to the peak pupil intensity may be greater than about 50% when using the partial elliptical reflector with the half spherical reflector as described herein. In other words, the intensity of the light at the edge of the pupil may be greater than about 50% of the peak intensity in the pupil. As such, using the partial elliptical reflector with the half spherical reflector as described herein results in much more uniformity in intensity across the pupil plane of the illumination subsystem compared to that achieved using only the partial elliptical reflector. Therefore, the embodiments described herein provide significant improvements in uniformity across the NA of the illumination subsystem and across apodization of the illumination subsystem.

The embodiments described herein also have built-in flexibility to adjust the pupil fill profile for certain inspection applications. For example, one or more parameters of both the partial elliptical reflector and the half spherical reflector can be altered to achieve the desired pupil fill profile for different inspection applications. In this manner, the illumination subsystem configurations described herein advantageously provide more variable parameters that can be selected and/or adjusted based on the pupil fill profile than currently used illumination subsystems.

The embodiment shown in FIG. 23 may be further configured as described herein. In addition, the embodiment shown in FIG. 23 may be included in any system embodiments described herein.

Another embodiment relates to a method for providing illumination of a specimen for a process performed on the specimen. The method includes focusing excitation light from a laser to an electrodeless lamp to generate a plasma in the electrodeless lamp such that the plasma generates light. Focusing the excitation light to the electrodeless lamp may be performed as described herein (e.g., using any of the embodiments of the focusing optics described herein). The excitation light may include any of the excitation light described herein. The laser may include any of the lasers described herein. The electrodeless lamp and the plasma may be further configured as described herein. The light generated by the plasma may include any of the light described herein.

The method also includes illuminating the specimen with the generated light during the process. Illuminating the specimen with the generated light may be performed as described further herein (e.g., using any of the embodiments of the illumination subsystems described herein). The specimen may include any of the specimens described herein. The process may include any of the processes described herein.

Each of the steps of the method described above may be performed as described further herein. In addition, the method described above may be performed by any of the system embodiments described herein. Furthermore, the method described above may include any other step(s) of any other method(s) described herein.

An additional embodiment relates to a method for determining one or more characteristics of a specimen. The method includes focusing excitation light from a laser to an electrodeless lamp to generate a plasma in the electrodeless lamp such that the plasma generates light. Focusing the excitation light from the laser to the electrodeless lamp may be performed according to any of the embodiments described herein (e.g., using any of the embodiments of the focusing optics described herein). The excitation light may include any of the excitation light described herein. The laser may include any of the lasers described herein. The electrodeless lamp and the plasma may be configured according to any of the embodiments described herein. The light generated by the plasma may include any of the light described herein.

The method also includes illuminating the specimen with the generated light. Illuminating the specimen with the generated light may be performed as described further herein (e.g., using an illumination subsystem configured as described further herein). The specimen may include any of the specimens described herein. In addition, the method includes generating output responsive to light from the specimen resulting from the illuminating step. Generating the output responsive to the light from the specimen may be performed as described further herein (e.g., using a detection subsystem configured as described further herein). The light from the specimen may include any of the light described herein (e.g., light scattered from the specimen, light reflected by the specimen, light diffracted from the specimen, or some combination thereof). The method further includes determining the one or more characteristics of the specimen using the output. Determining the one or more characteristics may be performed as described further herein (e.g., using a processor as described further herein). The one or more characteristics may include any of the characteristics described herein.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. For example, after the method determines the one or more characteristics of the specimen, the method may include storing the determined characteristic(s) in a storage medium. Furthermore, the results may be stored "permanently," "semi-permanently," temporarily, or for some period of time. For example, the storage medium may be random access memory (RAM), and the results may not necessarily persist indefinitely in the storage medium. In a similar manner, any of the embodiments of the systems described herein may be configured to store any of the results described herein in a storage medium as described above. Storing the results may be performed by any of the processors described herein.

Each of the steps of the method described above may be performed as described further herein. In addition, the method described above may be performed by any of the system embodiments described herein. Furthermore, the method described above may include any other step(s) of any other method(s) described herein.

Further modifications and alternative embodiments of various aspects of the invention may be apparent to those skilled in the art in view of this description. For example, methods and systems for providing illumination of a specimen for a process performed on the specimen are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to provide illumination of a specimen for a process performed on the specimen, comprising:
a laser configured to generate excitation light; and
focusing optics configured to focus the excitation light to a plasma in an electrodeless lamp such that the plasma generates light, wherein the system is further configured such that the light illuminates the specimen during the process.

2. The system of claim 1, wherein the laser comprises a cw laser.

3. The system of claim 1, wherein the laser comprises a diode laser, a diode laser stack, a fiber laser, a fiber coupled diode laser, a carbon dioxide laser, an acoustically modulated diode, or a diode pumped fiber laser.

4. The system of claim 1, wherein a power of the laser is greater than about 100 W.

5. The system of claim 1, wherein an optical average cw power of the excitation light is about 100 W to about 1000 W.

6. The system of claim 1, further comprising an additional laser configured to generate additional excitation light, wherein the focusing optics are further configured to focus the additional excitation light to the plasma, and wherein a sum of the power of the laser and the additional laser is in a range of about 100 W cw to about 1000 W cw.

7. The system of claim 1, wherein a wavelength of the excitation light is less than about 10 μm.

8. The system of claim 1, wherein the focusing optics are further configured to focus the excitation light to the lamp to initiate the plasma.

9. The system of claim 1, further comprising a pulsed light source, a radio frequency coil, a voltage source external to the lamp, or some combination thereof configured to initiate the plasma.

10. The system of claim 1, wherein the plasma has a geometry shaped to substantially match collection optics of a detection subsystem of a system configured to inspect the specimen.

11. The system of claim 1, wherein an excitation volume of the electrodeless lamp is substantially matched to a field of view of collection optics of a detection subsystem of a system configured to inspect the specimen.

12. The system of claim 1, wherein the plasma has a cylindrical shape substantially matched to image onto the specimen in the system.

13. The system of claim 1, wherein the focusing optics are further configured to focus the excitation light to a cylindrical-shaped region within the electrodeless lamp, and wherein the cylindrical-shaped region has a diameter of about 0.5 mm to about 1 mm and a thickness of about 100 μm to about 200 μm.

14. The system of claim 1, further comprising at least one additional laser configured to generate additional excitation light, wherein the focusing optics are further configured to focus the excitation light and the additional excitation light to the plasma simultaneously such that the excitation light and the additional excitation light overlap within a cylindrical-shaped region within the electrodeless lamp, and wherein the cylindrical-shaped region has a diameter of about 0.5 mm to about 1 mm and a thickness of about 100 μm to about 200 μm.

15. The system of claim 1, wherein the laser comprises a frequency doubled laser, and wherein a wavelength of the excitation light is about 0.4 μm to about 0.7 μm.

16. The system of claim 1, wherein the light generated by the plasma comprises deep ultraviolet light.

17. The system of claim 1, wherein the light generated by the plasma comprises broadband light.

18. The system of claim 1, wherein the light generated by the plasma has a single line spectra.

19. The system of claim 1, wherein the light generated by the plasma comprises light in a spectral region from about 180 nm to about 450 nm.

20. The system of claim 1, wherein the light generated by the plasma comprises light in a spectral region from about 200 nm to about 450 nm.

21. The system of claim 1, wherein the plasma is generated using a rare earth gas and a mercury gas, and wherein the light generated by the plasma comprises light in a spectral region from about 230 nm to about 480 nm.

22. The system of claim 1, wherein the light generated by the plasma comprises excimer radiation, and wherein the electrodeless lamp comprises about 1 atm or more of background rare gas and about 1 atm or less of a halide containing gas.

23. The system of claim 1, wherein the plasma has a diameter of about 0.5 mm to about 1 mm.

24. The system of claim 1, wherein the light generated by the plasma has a diameter of about 100 μm to about 2 mm.

25. The system of claim 1, wherein the electrodeless lamp is at a pressure of above about 1 atm at a working temperature of the electrodeless lamp, and wherein the light generated by the plasma comprises light in a spectral region from about 200 nm to about 400 nm.

26. The system of claim 1, wherein the light generated by the plasma has a brightness of about 10 W/mm$^2$-sr to about 50 W/mm$^2$-sr in a spectral region from about 200 nm to about 400 nm.

27. The system of claim 1, wherein the light generated by the plasma has a brightness of about 2 W/mm$^2$-sr to about 50 W/mm$^2$-sr in an integral region of the electromagnetic spectrum from about 200 nm to about 400 nm.

28. The system of claim 1, wherein the light generated by the plasma has an average power of at least about 3 W within any band in a spectral region from about 200 nm to about 450 nm.

29. The system of claim 1, wherein a temperature of the plasma is about 10,000 K to about 30,000 K.

30. The system of claim 1, , wherein a temperature of the plasma is held substantially constant by the excitation light.

31. The system of claim 1, wherein the electrodeless lamp further comprises a fill gas, and wherein the fill gas comprises argon, krypton, xenon, fluorine, chlorine, chlorine dimers, fluorine dimers, a homogeneous diatomic gas, nitrogen trifluoride, sulfur hexafluoride, nitric oxide, mercury, a halide containing gas, mercury halides, diatomic halides, halides, a rare gas, rare earths, transition metals, lanthanide metals, or some combination thereof.

32. The system of claim 1, wherein the electrodeless lamp further comprises a fill gas at a gas pressure such that an opacity of the plasma does not prohibit a majority of the light generated by the plasma from exiting the lamp.

33. The system of claim 1, wherein the plasma does not produce an average plasma opacity over a plasma axis length of greater than about 1 e-folding from one end of the electrodeless lamp to another end of the electrodeless lamp.

34. The system of claim 1, wherein the electrodeless lamp further comprises a fill gas, and wherein an opacity of the fill gas at a working temperature and pressure of the electrodeless lamp is less than or equal to about 10% reabsorption of light emitted from a center of the lamp within a spectral region from about 200 nm to about 450 nm.

35. The system of claim 1, wherein a fill pressure of gases in the electrodeless lamp is about 4 atm or higher.

36. The system of claim 1, wherein a fill pressure of the electrodeless lamp is about 5 atm to about 20 atm at room temperature.

37. The system of claim 1, wherein a gas pressure within the electrodeless lamp is about 1 atm to about 50 atm.

38. The system of claim 1, wherein the plasma comprises one or more species that fluoresce in a region between about 180 nm and about 350 nm to a ground electronic state.

39. The system of claim 1, wherein the plasma comprises one or more species that fluoresce in a region between about 180 nm and about 350 nm to a ground electronic state, and wherein the one or more species comprise mercury that emits resonance lines at 2537 Å, neutral barium that emits resonance lines at 2409 Å, neutral cobalt that emits resonance lines at 2402 Å, neutral magnesium that emits resonance lines at 2025 Å, neutral nickel that emits resonance lines at 2026 Å, neutral scandium that emits resonance lines at 2000 Å, neutral nickel terminating on a 879 $cm^{-1}$ electronic metastable state, or some combination thereof.

40. The system of claim 1, wherein the plasma comprises one or more species that fluoresce in a region between about 180 nm and about 350 nm to a ground electronic state, and wherein atoms or molecules that form the one or more species are present in the electrodeless lamp prior to generation of the plasma in a quantity or quantities that limit the vapor pressure of the atoms or molecules in the electrodeless lamp such that substantially all of the atoms or molecules are vaporized before the lamp reaches operating temperature.

41. The system of claim 1, wherein the plasma comprises one or more species that fluoresce in a region between about 180 nm and about 350 nm to a ground electronic state, and wherein the one or more species comprise atoms formed by decomposition of feed molecules in the electrodeless lamp.

42. The system of claim 1, wherein the plasma comprises one or more species that fluoresce in a region between about 180 nm and about 350 nm to electronic metastable states within about 0.5 eV of a ground electronic state.

43. The system of claim 1, wherein the plasma comprises one or more species that fluoresce in a region between about 180 nm and about 350 nm to electronic metastable states within about 0.5 eV of a ground electronic state, and wherein the one or more species comprise mercury that emits resonance lines at 2537 Å, neutral barium that emits resonance lines at 2409 Å, neutral cobalt that emits resonance lines at 2402 Å, neutral magnesium that emits resonance lines at 2025 Å, neutral nickel that emits resonance lines at 2026 Å, neutral scandium that emits resonance lines at 2000 Å, neutral nickel terminating on a 879 $cm^{-1}$ electronic metastable state, or some combination thereof.

44. The system of claim 1, wherein the plasma comprises one or more species that fluoresce in a region between about 180 nm and about 350 nm to electronic metastable states within about 0.5 eV of a ground electronic state, and wherein atoms or molecules that form the one or more species are present in the electrodeless lamp prior to generation of the plasma in a quantity or quantities that limit the vapor pressure of the atoms or molecules in the electrodeless lamp such that substantially all of the atoms or molecules are vaporized before the lamp reaches operating temperature.

45. The system of claim 1, wherein the plasma comprises one or more species that fluoresce in a region between about 180 nm and about 350 nm to electronic metastable states within about 0.5 eV of a ground electronic state, and wherein the one or more species comprise atoms formed by decomposition of feed molecules in the electrodeless lamp.

46. The system of claim 1, wherein the electrodeless lamp further comprises one or more operating gases that have atomic transitions from electronically excited states to a ground electronic state of one or more corresponding neutral atoms or a state within about 1 eV or about 2 eV of the ground electronic state.

47. The system of claim 1, wherein the electrodeless lamp further comprises feed molecules of which about 1% or greater are dissociated at an operating temperature proximate a center of the plasma.

48. The system of claim 1, wherein the electrodeless lamp further comprises feed molecules of which about 1% or greater are dissociated at an operating temperature of about 600 K to about 25,000 K.

49. The system of claim 1, wherein the electrodeless lamp further comprises feed molecules of which about 1% or greater are dissociated at an operating temperature proximate a center of the plasma, and wherein the feed molecules comprise iodine, chlorine, bromine, sulfur, nitrogen. oxygen, a diatomic gas, one or more homonuclear diatomic feed materials capable of recombining to form only their corresponding molecular species, one or more rare gases, or some combination thereof.

50. The system of claim 1, wherein the electrodeless lamp further comprises diatomic hydrogen, and wherein the light generated by the plasma has a wavelength of about 121 nm.

51. The system of claim 1, wherein the electrodeless lamp further comprises diatomic hydrogen, and wherein the light generated by the plasma has a wavelength of about 121 nm, about 937 nm, about 949 nm, about 972 nm, about 1025 nm, or some combination thereof.

52. The system of claim 1, wherein the electrodeless lamp further comprises a background rare gas and a gas containing a halide, wherein a pressure of the background rare gas is at least about 1 atm, and wherein a pressure of the gas containing the halide is less than or equal to about 1 atm.

53. The system of claim 1, wherein the electrodeless lamp further comprises one of an internal lens and a curved reflector.

54. The system of claim 1, wherein the focusing optics comprise a lens configured to focus the excitation light to a spot size and radiance sufficient to sustain the plasma.

55. The system of claim 1, wherein the focusing optics comprise a lens configured to focus the excitation light to a spot size and radiance sufficient to sustain the plasma, and wherein the lens has a numerical aperture of at least about 0.3.

56. The system of claim 1, wherein the focusing optics comprise a lens configured to focus the excitation light to the plasma such that the plasma has a predetermined shape, and wherein the lens has a numerical aperture of at least about 0.3.

57. The system of claim 1, further comprising at least one heat source located proximate to the electrodeless lamp and configured to maintain atoms in the plasma in a vapor phase.

58. The system of claim 1, further comprising an illumination subsystem configured to illuminate the specimen during the process with the light generated by the plasma, and wherein the illumination subsystem comprises a condenser lens configured to collect the light generated by the plasma.

59. The system of claim 1, further comprising an illumination subsystem configured to illuminate the specimen during the process with the light generated by the plasma, wherein the illumination subsystem comprises an elliptical reflector configured to collect the light generated by the plasma, and wherein the plasma is located at one focal point of the elliptical reflector.

60. The system of claim 1, wherein the specimen comprises a wafer.

61. The system of claim 1, wherein the specimen comprises a patterned wafer.

62. The system of claim 1, wherein the specimen comprises a reticle.

63. The system of claim 1, wherein a numerical aperture of the focusing optics is selected such that a size of the plasma is reduced along a direction to which the excitation light is focused to the plasma by the focusing optics.

64. The system of claim 1, wherein the laser comprises a distributed light source.

65. The system of claim 1, wherein the focusing optics comprise at least one optical element configured to focus the excitation light to the plasma and configured to collect the light generated by the plasma.

66. The system of claim 1, wherein the focusing optics are further configured to focus the excitation light to the plasma in two substantially opposite directions simultaneously.

67. The system of claim 1, wherein the focusing optics comprise at least one reflective optical element and at least one refractive optical element, and wherein the at least one reflective optical element and the at least one refractive optical element are configured to focus the excitation light to the plasma simultaneously.

68. The system of claim 1, wherein the focusing optics are further configured to focus the excitation light to the plasma in two substantially perpendicular directions simultaneously.

69. The system of claim 1, wherein the focusing optics are further configured to focus the excitation light to the plasma at different directions simultaneously to substantially the same focal spot.

70. The system of claim 1, wherein the focusing optics are further configured to focus the excitation light to the plasma at different directions simultaneously to offset focal spots.

71. The system of claim 1, wherein the focusing optics are further configured to collect the excitation light that is not absorbed by the plasma and to focus the collected excitation light to the plasma.

72. The system of claim 1, further comprising a gas flow subsystem configured to direct a gas to the plasma such that the gas directed to the plasma affects a shape of the plasma.

73. The system of claim 1, further comprising a gas flow subsystem configured to direct a gas to the plasma such that the gas directed to the plasma increases isolation of the plasma.

74. The system of claim 1, further comprising a gas flow subsystem configured to direct a gas to the plasma at a direction substantially opposite to a direction at which the focusing optics focus the excitation light to the plasma.

75. The system of claim 1, further comprising a gas flow subsystem configured to direct a gas to the plasma at a direction substantially perpendicular to a direction at which the focusing optics focus the excitation light to the plasma.

76. The system of claim 1, further comprising a gas flow subsystem configured to direct a gas to the plasma such that the gas increases propagation of the generated light through the plasma.

77. The system of claim 1, further comprising a gas flow subsystem configured to direct a gas to the plasma through an aperture in an optical element of the focusing optics.

78. The system of claim 1, further comprising a gas flow subsystem configured to direct a gas to the plasma through a sonic or supersonic nozzle to reduce a volume of the plasma and to reduce absorption of the generated light by the gas.

79. The system of claim 1, further comprising a gas flow subsystem configured to direct a gas to the plasma, wherein the gas flow subsystem comprises a cylindrical-shaped nozzle.

80. The system of claim 1, further comprising a gas flow subsystem configured to direct a gas to the plasma, wherein the gas directed to the plasma increases uniformity of a density profile of the plasma.

81. The system of claim 1, further comprising a gas flow subsystem configured to direct a gas to the plasma, wherein the gas directed to the plasma creates an interaction media having a density suitable for interactions between the excitation light and the plasma.

82. The system of claim 1 further comprising a gas flow subsystem configured to direct a gas jet to the plasma, wherein the focusing optics are further configured to direct the excitation light to one or more edges of the gas jet thereby affecting a shape of the gas jet.

83. The system of claim 1, further comprising a gas flow subsystem configured to direct a gas to the plasma, wherein a pressure of the gas directed to the plasma is selected based on one or more predetermined characteristics of the plasma.

84. The system of claim 1, further comprising a gas flow subsystem configured to direct a gas to the plasma, wherein the gas flow subsystem comprises a nozzle through which the gas is directed to the plasma, and wherein a diameter of the nozzle is selected based on one or more predetermined characteristics of the plasma.

85. The system of claim 1, wherein the system is further configured to apply an external magnetic field to the plasma to alter one or more characteristics of the plasma.

86. The system of claim 1, further comprising a gas flow subsystem configured to direct one or more feed materials to the plasma after generation of the plasma.

87. The system of claim 1, further comprising a cleaning subsystem configured to remove photocontamination from one or more optical elements of the focusing optics, one or more optical elements of the system, or some combination thereof.

88. The system of claim 1, wherein the plasma is generated from one or more feed materials comprising a liquid.

89. The system of claim 1, further comprising an illumination subsystem configured to illuminate the specimen during the process with the light generated by the plasma, wherein the illumination subsystem comprises a reflective optical element configured to collect the light generated by the plasma and to direct the collected light to one or more refractive optical elements of the illumination subsystem.

90. The system of claim 1, wherein the focusing optics comprise a reflective optical element configured to focus the excitation light to the plasma, and wherein the excitation light comprises an expanded laser beam.

91. The system of claim 1, wherein the focusing optics are further configured to focus the excitation light to the plasma at different directions simultaneously.

92. The system of claim 1, further comprising an illumination subsystem configured to illuminate the specimen during the process with the light generated by the plasma, wherein the illumination subsystem comprises one or more refractive optical elements configured to focus the excitation light to the plasma.

93. The system of claim 1, wherein the focusing optics comprise at least one optical element configured to focus the excitation light to the plasma and configured to collect the light generated by the plasma, and wherein the at least one optical element comprises a reflective optical element.

94. The system of claim 1, further comprising an illumination subsystem configured to illuminate the specimen during the process with the light generated by the plasma, wherein the illumination subsystem is further configured to collect the light generated by the plasma across a solid an-le of about 4 π.

95. The system of claim 1, further comprising an illumination subsystem configured to illuminate the specimen during the process with the light generated by the plasma, wherein the illumination subsystem is further configured to direct the light to a pupil plane of the system such that the light has a substantially uniform intensity across the pupil plane.

96. The system of claim 1, further comprising an illumination subsystem configured to illuminate the specimen during the process with the light generated by the plasma, wherein the illumination subsystem comprises a partial elliptical reflector and a half spherical reflector.

97. The system of claim 1, further comprising an illumination subsystem configured to illuminate the specimen during the process with the light generated by the plasma, wherein the illumination subsystem comprises a partial elliptical reflector and a half spherical reflector, wherein the plasma is positioned at one focal point of the partial elliptical reflector, and wherein the half spherical reflector is substantially centered to the plasma.

98. The system of claim 1, further comprising an illumination subsystem configured to illuminate the specimen during the process with the light generated by the plasma, wherein the illumination subsystem comprises a partial elliptical reflector and a half spherical reflector, wherein the partial elliptical reflector and the half spherical reflector are configured to collect the light generated by the plasma, wherein the half spherical reflector is configured to direct the light collected by the half spherical reflector to the partial elliptical reflector, and wherein the partial elliptical reflector is configured to direct the light from the half spherical reflector and the light collected by the partial elliptical reflector to another optical element of the illumination subsystem.

99. A method for providing illumination of a specimen for a process performed on the specimen, comprising:
focusing excitation light from a laser to an electrodeless lamp to generate a plasma in the electrodeless lamp such that the plasma generates light; and
illuminating the specimen with the generated light during the process.

100. A method for determining one or more characteristics of a specimen, comprising:
focusing excitation light from a laser to an electrodeless lamp to generate a plasma in the electrodeless lamp such that the plasma generates light;
illuminating the specimen with the generated light;
generating output responsive to light from the specimen resulting from said illuminating; and
determining the one or more characteristics of the specimen using the output.

101. A system configured to determine one or more characteristics of a specimen, comprising:
a laser configured to generate excitation light;
focusing optics configured to focus the excitation light to a plasma in an electrodeless lamp such that the plasma generates light;
an illumination subsystem configured to illuminate the specimen with the light generated by the plasma; and
a detection subsystem configured to generate output responsive to light from the specimen due to illumination of the specimen, wherein the output can be used to determine the one or more characteristics of the specimen.

102. The system of claim 101, wherein the system is further configured as a bright field inspection system.

103. The system of claim 101, wherein the system is further configured as a dark field inspection system.

104. The system of claim 101, wherein the system is further configured as a defect review system.

105. The system of claim 101, wherein the system is further configured as a metrology system.

106. The system of claim 101, wherein the one or more characteristics comprise one or more dimensions of one or more patterned features formed on the specimen.

107. The system of claim 101, wherein the one or more characteristics comprise a shape of one or more patterned features formed on the specimen.

108. The system of claim 101, wherein the specimen comprises a wafer.

109. The system of claim 101, wherein the specimen comprises a patterned wafer.

110. The system of claim 101, wherein the specimen comprises a reticle.

111. A system configured to generate an image of a specimen, comprising:
a laser configured to generate excitation light;
focusing optics configured to focus the excitation light to a plasma in an electrodeless lamp such that the plasma generates light;
an illumination subsystem configured to illuminate the specimen with the light generated by the plasma; and
a detection subsystem configured to generate output responsive to electrons emitted by the specimen due to illumination of the specimen with the light generated by the plasma, wherein the output comprises the image of the specimen.

112. The system of claim 111, wherein the light generated by the plasma comprises deep ultraviolet light.

113. The system of claim 111, wherein the specimen comprises a surface formed of a semiconductive material.

114. The system of claim 111, wherein the light generated by the plasma comprises broadband light such that the system can image a selectable set of work functions of the specimen.

115. A system configured to perform a lithography process on a specimen, comprising:
a laser configured to generate excitation light;
focusing optics configured to focus the excitation light to a plasma in an electrodeless lamp such that the plasma generates light; and
an illumination subsystem configured to image the light generated by the plasma onto the specimen in a predetermined pattern such that the predetermined pattern can be transferred to the specimen.

116. The system of claim 115, wherein the light generated by the plasma comprises i-line light.

* * * * *